US012099064B2

(12) United States Patent
Zhai et al.

(10) Patent No.: US 12,099,064 B2
(45) Date of Patent: *Sep. 24, 2024

(54) ANTI-HYPUSINE ANTIBODIES AND USES THEREOF

(71) Applicant: Genentech, Inc., South San Francisco, CA (US)

(72) Inventors: Qianting Zhai, South San Francisco, CA (US); Paul J. Carter, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 950 days.

This patent is subject to a terminal disclaimer.

(21) Appl. No.: 16/951,802

(22) Filed: Nov. 18, 2020

(65) Prior Publication Data

US 2021/0072250 A1     Mar. 11, 2021

Related U.S. Application Data

(63) Continuation of application No. 15/907,152, filed on Feb. 27, 2018, now Pat. No. 10,877,042, which is a continuation of application No. PCT/US2016/049127, filed on Aug. 26, 2016.

(60) Provisional application No. 62/211,642, filed on Aug. 28, 2015.

(51) Int. Cl.
| | |
|---|---|
| *G01N 33/68* | (2006.01) |
| *C07K 16/18* | (2006.01) |
| *C07K 16/44* | (2006.01) |
| *G01N 33/52* | (2006.01) |

(Continued)

(52) U.S. Cl.
CPC ......... *G01N 33/6812* (2013.01); *C07K 16/18* (2013.01); *C07K 16/44* (2013.01); *G01N 33/521* (2013.01); *G01N 33/5308* (2013.01); *G01N 33/533* (2013.01); *G01N 33/6872* (2013.01);

(Continued)

(58) Field of Classification Search
None
See application file for complete search history.

(56) References Cited

U.S. PATENT DOCUMENTS

| | | | |
|---|---|---|---|
| 5,973,113 | A | 10/1999 | Bergeron |
| 10,877,042 | B2 | 12/2020 | Zhai et al. |
| 2011/0177089 | A1 | 7/2011 | Sekoi et al. |

(Continued)

FOREIGN PATENT DOCUMENTS

| | | |
|---|---|---|
| CN | 101386842 A | 3/2009 |
| CN | 111565752 A | 8/2020 |

(Continued)

OTHER PUBLICATIONS

Carvajal-Gamez et al. (2010, e-pub. Jan. 7, 2010). "Identification of Two Novel Trichomonas vaginalis eif-5a Genes," Infection, Genetics and Evolution 10(2):284-291.

(Continued)

*Primary Examiner* — Juliet C Switzer
*Assistant Examiner* — Alexander Alexandrovic Volkov
(74) *Attorney, Agent, or Firm* — MORRISON & FOERSTER LLP

(57) ABSTRACT

The invention provides anti-hypusine antibodies and their use in detecting and isolating polypeptides containing hypusine and/or deoxyhypusine, as well as compositions and kits comprising the anti-hypusine antibodies.

23 Claims, 18 Drawing Sheets

Specification includes a Sequence Listing.

(51) Int. Cl.
*G01N 33/53* (2006.01)
*G01N 33/533* (2006.01)

(52) U.S. Cl.
CPC ...... *C07K 2317/34* (2013.01); *G01N 2800/50* (2013.01)

(56) References Cited

U.S. PATENT DOCUMENTS

2015/0119476 A1 4/2015 Mirmira
2018/0328938 A1 11/2018 Zhai et al.

FOREIGN PATENT DOCUMENTS

| WO | 1999026963 A1 | 6/1999 | |
|---|---|---|---|
| WO | WO-2004024087 A2 * | 3/2004 | ......... C07K 14/4702 |
| WO | 2004024087 A3 | 11/2005 | |
| WO | 2019100005 A1 | 5/2019 | |

OTHER PUBLICATIONS

Cracchiolo et al. (2004, e-pub. May 19, 2004). "Eukaryotic Initiation Factor 5A-1 (eIF5A-1) as a Diagnostic Marker for Aberrant Proliferation in Intraepithelial Neoplasia of the Vulva," Gynecologic Oncology 94(1):217-222.
International Preliminary Report on Patentability issued on Mar. 6, 2018, for Application No. PCT/US2016/049127, filed on Aug. 26, 2016, 7 pages.
International Search Report mailed on Nov. 11, 2016, for Application No. PCT/US2016/049127, filed on Aug. 26, 2016, 5 pages.
Nishiki et al. (2013). "Characterization of a Novel Polyclonal Anti-Hypusine Antibody," SpringerPlus 2:421, 5 pages.
Written Opinion mailed on Nov. 11, 2016, for Application No. PCT/US2016/049127, filed on Aug. 26, 2016, 6 pages.
Yuan et al. (2009). "Structure and Function of Eukaryotic Initiation Factor 5A: Recent Progress in Research." Bulletin of The Academy of Military Medical Sciences 33(3):267-271. in Chinese with English Abstract.
Zhai et al. (2016, e-pub. Jan. 14, 2016). "Structural Analysis and Optimization of Context-Independent Anti-Hypusine Antibodies," Journal of Molecular Biology 428(3):603-617, 15 pages.

* cited by examiner

FIG. 1A

Light chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| Hpu24 | A | A | V | L | T | Q | T | P | S | P | V | S | A | A | V | G | G | T | V | T | I | S | C | Q | S | S | E | T | V | Y | R | G | D | W | L | S | W | F | Q | K |
| Hpu24.B | A | A | V | L | T | Q | T | P | S | P | V | S | A | A | V | G | G | T | V | T | I | S | C | R | S | S | Q | R | V | Y | L | G | D | W | L | S | W | F | Q | K |

CDR L1 - Contact: positions 30–36
CDR L1 - Kabat: positions 24–34

| Kabat number | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|
| Hpu24 | P | G | Q | P | P | K | L | L | I | Y | D | A | S | Y | L | A | S | G | V | S | S | R | F | S | G | S | G | S | G | T | H | F | T | L | T | I | S | G | V | Q |
| Hpu24.B | P | G | Q | P | P | K | L | L | I | Y | D | A | S | F | R | G | D | G | V | S | S | R | F | S | G | S | G | S | G | T | H | F | T | L | T | I | S | G | V | Q |

CDR L2 - Contact: positions 46–54
CDR L2 - Kabat: positions 50–56

| Kabat number | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|
| Hpu24 | C | D | D | A | A | T | Y | Y | C | L | G | G | Y | Y | D | F | G | G | G | T | E | V | V | V | K | | | |
| Hpu24.B | C | D | D | A | D | T | Y | Y | C | L | G | G | Y | Y | D | F | G | G | G | T | E | V | V | V | K | | | |

CDR L3 - Contact: positions 89–96
CDR L3 - Kabat: positions 89–97

FIG. 1B

Heavy chain variable region

```
Kabat number  1  2  3  4  5  6  7  8  9  10 11 12 13 14 15 16 17 18 19 20 21 22 23 24 25 26 27 28 29 30 31 32 33 34 35 36 37 38 39 40
Hpu24         Q  E  Q  L  K  E  S  G  G  R  L  V  A  P  G  T  P  L  T  C  T  V  S  G  F  D  I  S  D  Y  A  M  I  W  V  R  Q  A  P  G
Hpu24.B       Q  E  Q  L  K  E  S  G  G  R  L  V  A  P  G  T  P  L  T  C  T  V  S  G  F  D  I  S  D  Y  A  M  I  W  V  R  Q  A  P  G
                                                                                        └─────── CDR H1 - Contact ───────┘
                                                                                              └─ CDR H1 - Kabat ─┘

Kabat number  43 44 45 46 47 48 49 50 51 52 53 54 55 56 57 58 59 60 61 62 63 64 65 66 67 68 69 70 71 72 73 74 75 76 77 78 79 80 81 82 83
Hpu24         K  G  L  E  W  I  G  I  I  Y  G  G  S  N  K  L  A  Y  A  K  W  A  K  G  R  F  T  I  S  R  T  S  T  T  V  D  L  K  I  T  S  P
Hpu24.B       K  G  L  E  W  I  G  I  I  Y  G  V  I  N  D  L  A  Y  A  K  W  A  K  G  R  F  T  I  S  R  T  S  T  T  V  D  L  K  I  T  S  P
                                        └──── CDR H2 - Contact ────┘
                                           └──────── CDR H2 - Kabat ────────┘

Kabat number  86 87 88 89 90 91 92 93 94 95 96 97 98 99 100 101 102 103 104 105 106 107 108 109 110 111 112 113
Hpu24         T  T  E  D  T  A  T  Y  F  C  A  R  G  Y   G   S   M   D   G   Y   D   R   L   N   L   W  G  Q  G  T  L  V  T  V  S  S
Hpu24.B       T  T  E  D  T  A  T  Y  F  C  A  R  G  Y   G   S   M   D   G   Y   D   R   L   N   L   W  G  Q  G  T  L  V  T  V  S  S
                                          └──── CDR H3 - Contact ────┘
                                             └──── CDR H3 - Kabat ────┘
```

FIG. 1D

Heavy chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Hpu98 | Q | S | V | E | E | S | G | G | R | L | V | T | P | G | T | P | L | T | L | T | C | T | V | S | G | F | A | S | L | S | T | Y | T | M | N | W | V | R | Q | A | P | G |
| Hpu98.61 | Q | S | V | E | E | S | G | G | R | L | V | T | P | G | T | P | L | T | L | T | C | T | V | S | G | F | A | S | L | S | Y | H | C | M | N | W | V | R | Q | A | P | G |
| Hpu91 | Q | S | V | E | E | S | G | G | R | L | V | T | P | G | T | P | L | T | L | T | C | T | V | S | A | F | S | L | S | T | Y | T | I | N | W | V | R | Q | A | P | G |

CDR H1 - Contact
CDR H1 - Kabat

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|
| Hpu98 | K | G | L | E | W | I | G | D | I | Y | T | D | G | N | T | Y | Y | A | N | W | A | K | G | R | F | T | I | S | K | T | S | T | T | V | D | L | K | I | T | S | P |
| Hpu98.61 | K | G | L | E | W | I | G | D | I | Y | T | D | G | N | T | Y | Y | A | N | W | A | K | G | R | F | T | I | S | K | T | S | T | T | V | D | L | K | I | T | S | P |
| Hpu91 | K | G | L | E | W | I | G | D | I | W | S | D | G | N | T | Y | Y | A | N | W | A | K | G | R | F | T | I | S | K | T | S | T | T | V | D | L | K | I | T | S | P |

CDR H2 - Contact
CDR H2 - Kabat

| Kabat number | 82b | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|
| Hpu98 | T | T | E | D | T | A | T | Y | F | C | A | R | D | S | W | D | A | S | S | Y | Y | G | L | D | L | W | G | Q | G | T | L | V | T | V | S | S |
| Hpu98.61 | T | T | E | D | T | A | T | Y | F | C | A | R | D | S | W | D | A | S | S | Y | Y | G | L | D | L | W | G | Q | G | T | L | V | T | V | S | S |
| Hpu91 | T | T | E | D | T | A | T | Y | F | C | A | R | D | S | W | D | T | Y | Y | Y | G | L | D | L | W | G | Q | G | T | L | V | T | V | S | S | |

CDR H3 - Contact
CDR H3 - Kabat

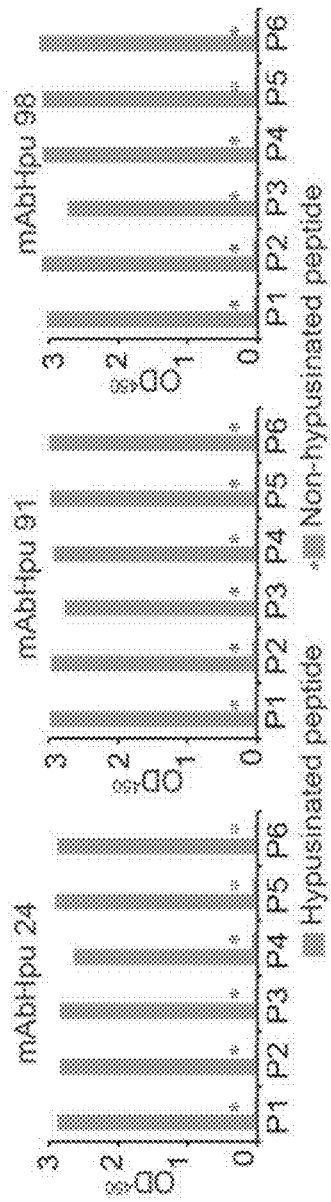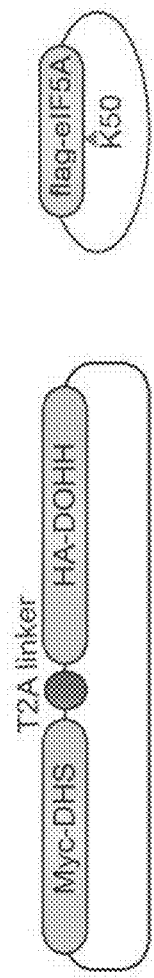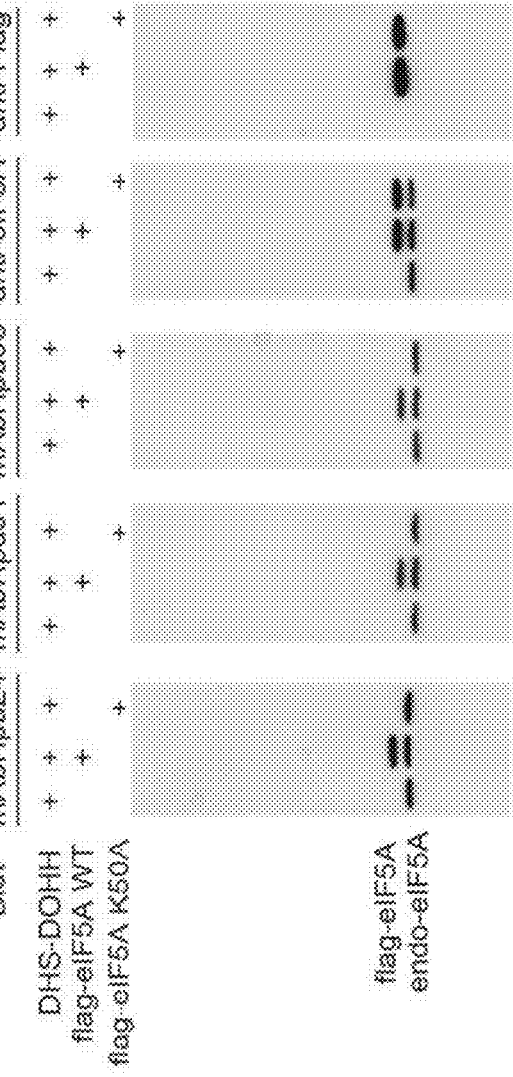
FIG. 2A
FIG. 2B
FIG. 2C

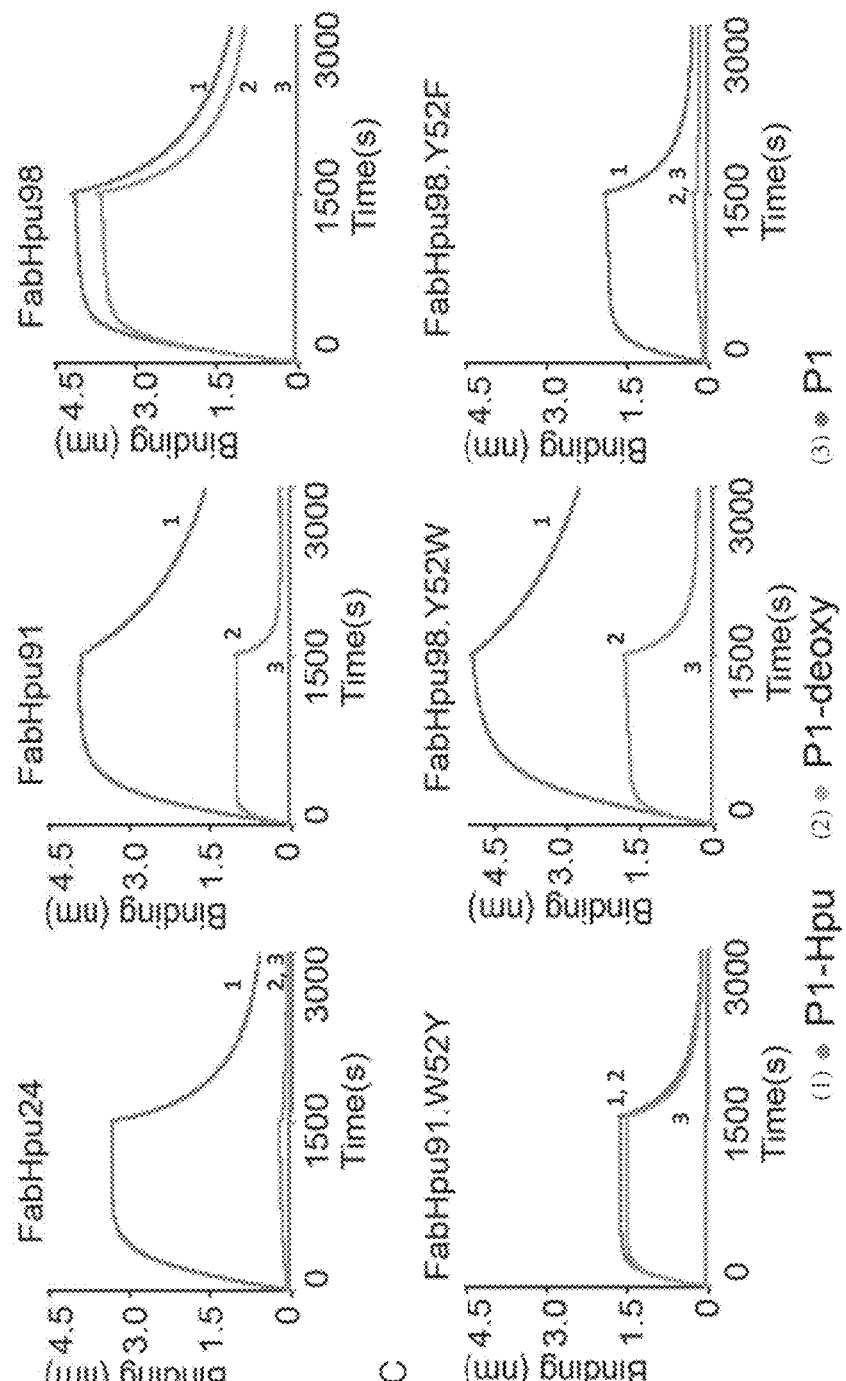
FIG. 3A
FIG. 3B
FIG. 3C

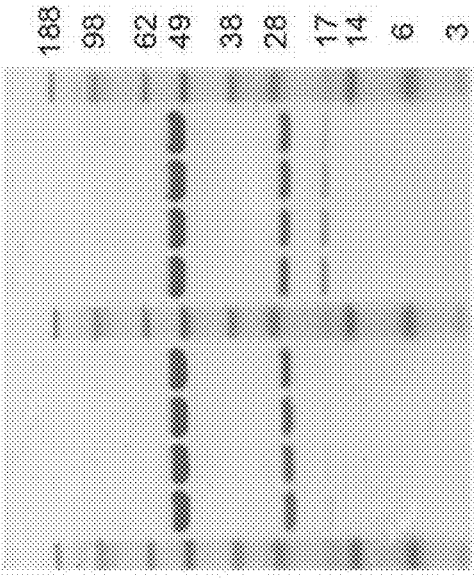
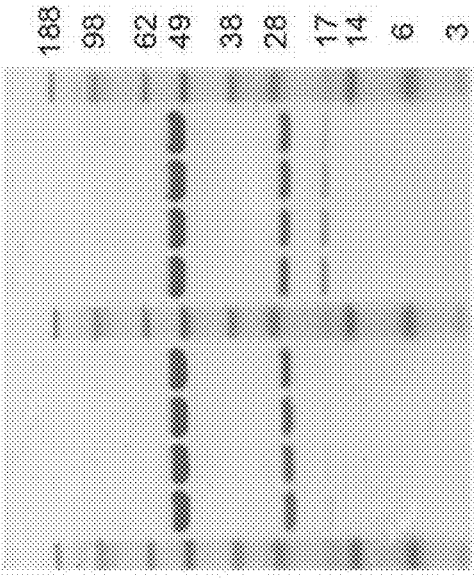
FIG. 7A
FIG. 7B

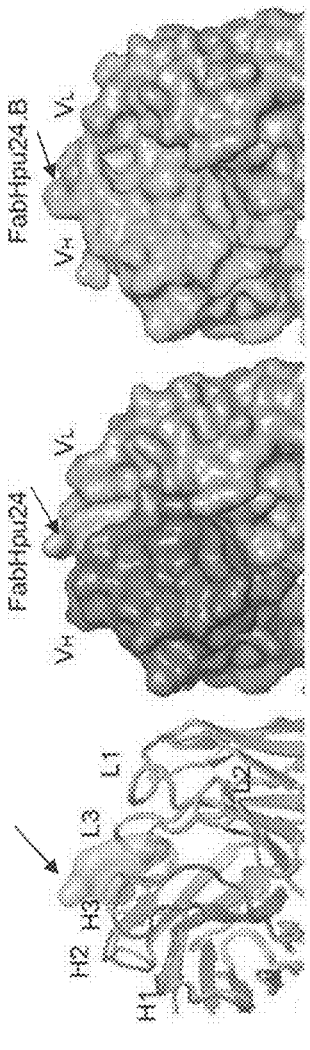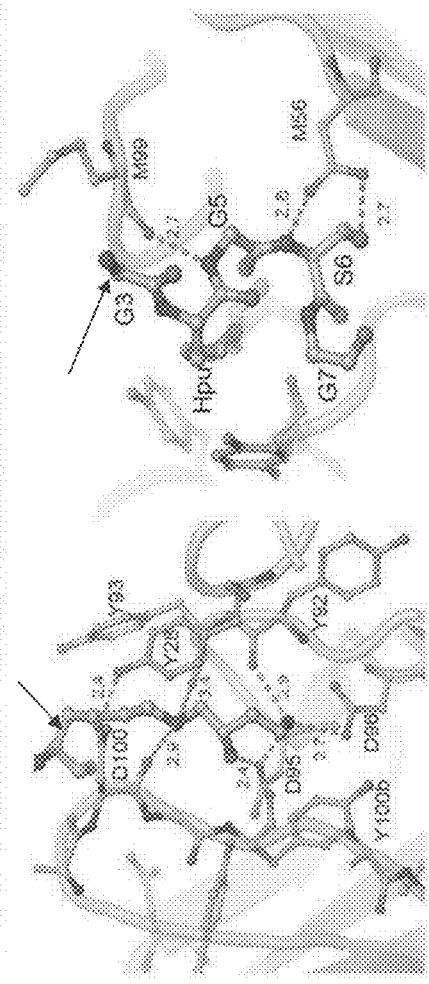
FIG. 12A
FIG. 12B
FIG. 12C
FIG. 12D

SEQUENCE LISTING

<160> NUMBER OF SEQ ID NOS: 72

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Gln Ser Ser Glu Thr Val Tyr Arg Gly Asp Trp Leu Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Arg Ser Arg Gln Arg Val Tyr Leu Gly Asp Trp Leu Ser
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Gln Ala Ser Glu Asp Ile Lys Arg Tyr Leu Ala
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Asp Ala Ser Tyr Leu Ala Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Asp Ala Ser Phe Arg Gly Asp

```
<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Ala Ala Ser Lys Leu Ala Ser
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Leu Gly Gly Tyr Tyr Asp Asp Ala Asp Asp Thr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Gln Gln Gly Tyr Thr Ser Ser Asn Val Asn Asn Ala
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Asp Tyr Ala Met Ile
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Thr Tyr Thr Ile Asn
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Thr Tyr Thr Met Asn
1               5
```

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

His Cys Thr Met Asn
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Ile Ile Tyr Gly Gly Ser Asn Lys Leu Ala Tyr Ala Lys Trp Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Ile Ile Tyr Gly Val Ile Asn Asp Leu Ala Tyr Ala Lys Trp Ala
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: Synthetic Construct

<400> SEQUENCE: 15

Asp Ile Trp Ser Asp Gly Asn Thr Tyr Tyr Ala Asn Trp Ala
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic Construct

<400> SEQUENCE: 16

Asp Ile Tyr Thr Asp Gly Asn Thr Tyr Tyr Ala Asn Trp Ala
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct

<400> SEQUENCE: 17

Gly Tyr Gly Ser Met Asp Gly Tyr Asp Arg Leu Asn Leu
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Asp Ser Trp Asp Thr Ser Ile Tyr Tyr Gly Leu Asp Leu
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic Construct

<400> SEQUENCE: 19

Asp Ser Trp Asp Ala Ser Ser Tyr Tyr Gly Leu Asp Leu
1               5                   10

<210> SEQ ID NO 20
<211> LENGTH: 111
<212> TYPE: PRT
<213> ORGANISM: Artificial Sequence
<220> FEATURE:
<223> OTHER INFORMATION: Synthetic Construct

<400> SEQUENCE: 20

Ala Ala Val Leu Thr Gln Thr Pro Ser Pro Val Ser Ala Ala Val Gly
1               5                   10                  15

Gly Thr Val Thr Ile Ser Cys Gln Ser Glu Thr Val Tyr Arg Gly
            20                  25                  30

Asp Trp Leu Ser Trp Phe Gln Lys Lys Pro Gly Gln Pro Pro Lys Leu
        35                  40                  45

Leu Ile Tyr Asp Ala Ser Tyr Leu Ala Ser Gly Val Ser Ser Arg Phe
    50                  55                  60

Ser Gly Ser Gly Ser Gly Thr His Phe Thr Leu Thr Ile Ser Gly Val
65                  70                  75                  80

Gln Cys Asp Asp Ala Ala Thr Tyr Tyr Cys Leu Gly Gly Tyr Tyr Asp
                85                  90                  95

Asp Ala Asp Asp Thr Phe Gly Gly Gly Thr Glu Val Val Lys
            100                 105                 110

<210> SEQ ID NO 21
<211> LENGTH: 111
<212> TYPE: PRT
<213> ORGANISM: Artificial Sequence
<220> FEATURE:
<223> OTHER INFORMATION: Synthetic Construct

<400> SEQUENCE: 21

Ala Ala Val Leu Thr Gln Thr Pro Ser Pro Val Ser Ala Ala Val Gly
1               5                   10                  15

Gly Thr Val Thr Ile Ser Cys Arg Ser Arg Gln Arg Val Tyr Leu Gly
            20                  25                  30

Asp Trp Leu Ser Trp Phe Gln Lys Lys Pro Gly Gln Pro Pro Lys Leu
        35                  40                  45

Leu Ile Tyr Asp Ala Ser Phe Arg Gly Asp Gly Val Ser Ser Arg Phe
    50                  55                  60

```
Ser Gly Ser Gly Ser Gly Thr His Phe Thr Leu Thr Ile Ser Gly Val
65                  70                  75                  80

Gln Cys Asp Asp Ala Ala Thr Tyr Tyr Cys Leu Gly Gly Tyr Tyr Asp
                85                  90                  95

Asp Ala Asp Asp Thr Phe Gly Gly Gly Thr Glu Val Val Val Lys
                100                 105                 110

<210> SEQ ID NO 22
<211> LENGTH: 110
<212> TYPE: PRT
<213> ORGANISM: Artificial Sequence
<220> FEATURE:
<223> OTHER INFORMATION: Synthetic Construct

<400> SEQUENCE: 22

Ala Ile Lys Met Thr Gln Thr Pro Ser Ser Val Ser Ala Ala Val Gly
1               5                   10                  15

Gly Thr Val Thr Ile Asn Cys Gln Ala Ser Glu Asp Ile Lys Arg Tyr
                20                  25                  30

Leu Ala Trp Tyr Gln Gln Lys Pro Gly Gln Pro Pro Lys Leu Leu Ile
            35                  40                  45

Tyr Ala Ala Ser Lys Leu Ala Ser Gly Val Ser Ser Arg Phe Thr Gly
        50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Gln Gly Tyr Thr Ser Thr Asn
                85                  90                  95

Val Asn Asn Ala Phe Gly Gly Gly Thr Glu Val Val Val Lys
                100                 105                 110

<210> SEQ ID NO 23
<211> LENGTH: 110
<212> TYPE: PRT
<213> ORGANISM: Artificial Sequence
<220> FEATURE:
<223> OTHER INFORMATION: Synthetic Construct

<400> SEQUENCE: 23

Ala Ile Lys Met Thr Gln Thr Pro Ser Ser Val Ser Ala Ala Val Gly
1               5                   10                  15

Gly Thr Val Thr Ile Asn Cys Gln Ala Ser Glu Asp Ile Lys Arg Tyr
                20                  25                  30

Leu Ala Trp Tyr Gln Gln Lys Pro Gly Gln Pro Pro Lys Leu Leu Ile
            35                  40                  45

Tyr Ala Ala Ser Lys Leu Ala Ser Gly Val Ser Ser Arg Phe Lys Gly
        50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Gln Gly Tyr Thr Ser Ser Asn
                85                  90                  95

Val Asn Asn Ala Phe Gly Gly Gly Thr Glu Val Val Val Lys
                100                 105                 110

<210> SEQ ID NO 24
<211> LENGTH: 120
<212> TYPE: PRT
<213> ORGANISM: Artificial Sequence
<220> FEATURE:
<223> OTHER INFORMATION: Synthetic Construct
```

-continued

```
<400> SEQUENCE: 24

Gln Glu Gln Leu Lys Glu Ser Gly Gly Arg Leu Val Ala Pro Gly Thr
1               5                   10                  15

Pro Leu Thr Leu Thr Cys Thr Val Ser Gly Phe Asp Ile Ser Asp Tyr
            20                  25                  30

Ala Met Ile Trp Val Arg Gln Ala Pro Gly Lys Gly Leu Glu Trp Ile
        35                  40                  45

Gly Ile Ile Tyr Gly Gly Ser Asn Lys Leu Ala Tyr Ala Lys Trp Ala
    50                  55                  60

Lys Gly Arg Phe Thr Ile Ser Arg Thr Ser Thr Val Asp Leu Lys
65                  70                  75                  80

Ile Thr Ser Pro Thr Thr Glu Asp Thr Ala Thr Tyr Phe Cys Ala Arg
                85                  90                  95

Gly Tyr Gly Ser Met Asp Gly Tyr Asp Arg Leu Asn Leu Trp Gly Gln
            100                 105                 110

Gly Thr Leu Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Synthetic Construct

<400> SEQUENCE: 25

Gln Glu Gln Leu Lys Glu Ser Gly Gly Arg Leu Val Ala Pro Gly Thr
1               5                   10                  15

Pro Leu Thr Leu Thr Cys Thr Val Ser Gly Phe Asp Ile Ser Asp Tyr
            20                  25                  30

Ala Met Ile Trp Val Arg Gln Ala Pro Gly Lys Gly Leu Glu Trp Ile
        35                  40                  45

Gly Ile Ile Tyr Gly Val Ile Asn Asp Leu Ala Tyr Ala Lys Trp Ala
    50                  55                  60

Lys Gly Arg Phe Thr Ile Ser Arg Thr Ser Thr Val Asp Leu Lys
65                  70                  75                  80

Ile Thr Ser Pro Thr Thr Glu Asp Thr Ala Thr Tyr Phe Cys Ala Arg
                85                  90                  95

Gly Tyr Gly Ser Met Asp Gly Tyr Asp Arg Leu Asn Leu Trp Gly Gln
            100                 105                 110

Gly Thr Leu Val Thr Val Ser Ser
        115                 120

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

Gln Ser Val Glu Glu Ser Gly Gly Arg Leu Val Thr Pro Gly Thr Pro
1               5                   10                  15

Leu Thr Leu Thr Cys Thr Val Ser Ala Phe Ser Leu Ser Thr Tyr Thr
            20                  25                  30

Ile Asn Trp Val Arg Gln Ala Pro Gly Lys Gly Leu Glu Trp Ile Gly
        35                  40                  45
```

```
Asp Ile Trp Ser Asp Gly Asn Thr Tyr Tyr Ala Asn Trp Ala Lys Gly
        50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Asp Ser
                 85                  90                  95

Trp Asp Thr Ser Ile Tyr Tyr Gly Leu Asp Leu Trp Gly Gln Gly Thr
                100                 105                 110

Leu Val Thr Val Ser Ser
        115
```

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct

<400> SEQUENCE: 27

```
Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Thr Tyr Thr
                20                  25                  30

Met Asn Trp Val Arg Gln Ala Pro Gly Lys Gly Leu Glu Trp Ile Gly
            35                  40                  45

Asp Ile Tyr Thr Asp Gly Asn Thr Tyr Tyr Ala Asn Trp Ala Lys Gly
        50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Asp Ser
                 85                  90                  95

Trp Asp Ala Ser Ser Tyr Tyr Gly Leu Asp Leu Trp Gly Gln Gly Thr
                100                 105                 110

Leu Val Thr Val Ser Ser
        115
```

<210> SEQ ID NO 28
<211> LENGTH: 118
<212> TYPE: PRT
<213> ORGANISM: Artificial Sequence
<220> FEATURE:
<223> OTHER INFORMATION: Synthetic Construct

<400> SEQUENCE: 28

```
Gln Ser Val Glu Glu Ser Gly Gly Arg Leu Val Thr Pro Gly Thr Pro
 1               5                  10                  15

Leu Thr Leu Thr Cys Thr Val Ser Ala Cys Ser Leu Tyr His Cys Thr
                20                  25                  30

Met Asn Trp Val Arg Gln Ala Pro Gly Lys Gly Leu Glu Trp Ile Gly
            35                  40                  45

Asp Ile Tyr Thr Asp Gly Asn Thr Tyr Tyr Ala Asn Trp Ala Lys Gly
        50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Asp Ser
                 85                  90                  95

Trp Asp Ala Ser Ser Tyr Tyr Gly Leu Asp Leu Trp Gly Gln Gly Thr
                100                 105                 110
```

Leu Val Thr Val Ser Ser
        115

<210> SEQ ID NO 29
<211> LENGTH: 215
<212> TYPE: PRT
<213> ORGANISM: Artificial Sequence
<220> FEATURE:
<223> OTHER INFORMATION: Synthetic Construct

<400> SEQUENCE: 29

Ala Ala Val Leu Thr Gln Thr Pro Ser Pro Val Ser Ala Ala Val Gly
1               5                   10                  15

Gly Thr Val Thr Ile Ser Cys Gln Ser Ser Glu Thr Val Tyr Arg Gly
            20                  25                  30

Asp Trp Leu Ser Trp Phe Gln Lys Lys Pro Gly Gln Pro Pro Lys Leu
        35                  40                  45

Leu Ile Tyr Asp Ala Ser Tyr Leu Ala Ser Gly Val Ser Ser Arg Phe
    50                  55                  60

Ser Gly Ser Gly Ser Gly Thr His Phe Thr Leu Thr Ile Ser Gly Val
65                  70                  75                  80

Gln Cys Asp Asp Ala Ala Thr Tyr Tyr Cys Leu Gly Tyr Tyr Asp
                85                  90                  95

Asp Ala Asp Thr Phe Gly Gly Thr Glu Val Val Lys Gly
            100                 105                 110

Asp Pro Val Ala Pro Thr Val Leu Ile Phe Pro Pro Ala Ala Asp Gln
        115                 120                 125

Val Ala Thr Gly Thr Val Thr Ile Val Cys Val Ala Asn Lys Tyr Phe
130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Asn Arg Gly Asp Cys
    210                 215

<210> SEQ ID NO 30
<211> LENGTH: 215
<212> TYPE: PRT
<213> ORGANISM: Artificial Sequence
<220> FEATURE:
<223> OTHER INFORMATION: Synthetic Construct

<400> SEQUENCE: 30

Ala Ala Val Leu Thr Gln Thr Pro Ser Pro Val Ser Ala Ala Val Gly
1               5                   10                  15

Gly Thr Val Thr Ile Ser Cys Arg Ser Arg Gln Arg Val Tyr Leu Gly
            20                  25                  30

Asp Trp Leu Ser Trp Phe Gln Lys Lys Pro Gly Gln Pro Pro Lys Leu
        35                  40                  45

Leu Ile Tyr Asp Ala Ser Phe Arg Gly Asp Gly Val Ser Ser Arg Phe
    50                  55                  60

Ser Gly Ser Gly Ser Gly Thr His Phe Thr Leu Thr Ile Ser Gly Val

```
                65                  70                  75                  80
Gln Cys Asp Asp Ala Ala Thr Tyr Tyr Cys Leu Gly Gly Tyr Tyr Asp
                    85                  90                  95

Asp Ala Asp Asp Thr Phe Gly Gly Gly Thr Glu Val Val Lys Gly
                100                 105                 110

Asp Pro Val Ala Pro Thr Val Leu Ile Phe Pro Pro Ala Ala Asp Gln
                115                 120                 125

Val Ala Thr Gly Thr Val Thr Ile Val Cys Val Ala Asn Lys Tyr Phe
130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
                180                 185                 190

Lys Glu Tyr Thr Cys Lys Val Thr Gln Gly Thr Thr Ser Val Val Gln
                195                 200                 205

Ser Phe Asn Arg Gly Asp Cys
210                 215

<210> SEQ ID NO 31
<211> LENGTH: 214
<212> TYPE: PRT
<213> ORGANISM: Artificial Sequence
<220> FEATURE:
<223> OTHER INFORMATION: Synthetic Construct

<400> SEQUENCE: 31

Ala Ile Lys Met Thr Gln Thr Pro Ser Ser Val Ser Ala Ala Val Gly
1               5                   10                  15

Gly Thr Val Thr Ile Asn Cys Gln Ala Ser Glu Asp Ile Lys Arg Tyr
                20                  25                  30

Leu Ala Trp Tyr Gln Gln Lys Pro Gly Gln Pro Pro Lys Leu Leu Ile
            35                  40                  45

Tyr Ala Ala Ser Lys Leu Ala Ser Gly Val Ser Ser Arg Phe Thr Gly
        50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Gln Gly Tyr Thr Ser Thr Asn
                85                  90                  95

Val Asn Asn Ala Phe Gly Gly Gly Thr Glu Val Val Lys Gly Asp
                100                 105                 110

Pro Val Ala Pro Thr Val Leu Ile Phe Pro Pro Ala Ala Asp Gln Val
                115                 120                 125

Ala Thr Gly Thr Val Thr Ile Val Cys Val Ala Asn Lys Tyr Phe Pro
130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
                180                 185                 190

Glu Tyr Thr Cys Lys Val Thr Gln Gly Thr Thr Ser Val Val Gln Ser
            195                 200                 205

Phe Asn Arg Gly Asp Cys
```

```
<210> SEQ ID NO 32
<211> LENGTH: 214
<212> TYPE: PRT
<213> ORGANISM: Artificial Sequence
<220> FEATURE:
<223> OTHER INFORMATION: Synthetic Construct

<400> SEQUENCE: 32
```

Ala Ile Lys Met Thr Gln Thr Pro Ser Ser Val Ser Ala Ala Val Gly
 1               5                  10                  15

Gly Thr Val Thr Ile Asn Cys Gln Ala Ser Glu Asp Ile Lys Arg Tyr
             20                  25                  30

Leu Ala Trp Tyr Gln Gln Lys Pro Gly Gln Pro Pro Lys Leu Leu Ile
         35                  40                  45

Tyr Ala Ala Ser Lys Leu Ala Ser Gly Val Ser Ser Arg Phe Lys Gly
 50                  55                  60

Ser Gly Ser Gly Thr Glu Tyr Thr Leu Thr Ile Ser Gly Val Gln Cys
 65                  70                  75                  80

Asp Asp Ala Ala Thr Tyr Tyr Cys Gln Gln Gly Tyr Thr Ser Ser Asn
                 85                  90                  95

Val Asn Asn Ala Phe Gly Gly Gly Thr Glu Val Val Val Lys Gly Asp
            100                 105                 110

Pro Val Ala Pro Thr Val Leu Ile Phe Pro Pro Ala Ala Asp Gln Val
        115                 120                 125

Ala Thr Gly Thr Val Thr Ile Val Cys Val Ala Asn Lys Tyr Phe Pro
130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Asn Arg Gly Asp Cys
    210

```
<210> SEQ ID NO 33
<211> LENGTH: 224
<212> TYPE: PRT
<213> ORGANISM: Artificial Sequence
<220> FEATURE:
<223> OTHER INFORMATION: Synthetic Construct

<400> SEQUENCE: 33
```

Gln Glu Gln Leu Lys Glu Ser Gly Gly Arg Leu Val Ala Pro Gly Thr
 1               5                  10                  15

Pro Leu Thr Leu Thr Cys Thr Val Ser Gly Phe Asp Ile Ser Asp Tyr
             20                  25                  30

Ala Met Ile Trp Val Arg Gln Ala Pro Gly Lys Gly Leu Glu Trp Ile
         35                  40                  45

Gly Ile Ile Tyr Gly Gly Ser Asn Lys Leu Ala Tyr Ala Lys Trp Ala
 50                  55                  60

Lys Gly Arg Phe Thr Ile Ser Arg Thr Ser Thr Thr Val Asp Leu Lys
 65                  70                  75                  80

Ile Thr Ser Pro Thr Thr Glu Asp Thr Ala Thr Tyr Phe Cys Ala Arg
                85                  90                  95

Gly Tyr Gly Ser Met Asp Gly Tyr Asp Arg Leu Asn Leu Trp Gly Gln
            100                 105                 110

Gly Thr Leu Val Thr Val Ser Ser Gly Gln Pro Lys Gly Pro Ser Val
        115                 120                 125

Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Ala Thr Asn
        195                 200                 205

Thr Lys Val Asp Lys Thr Val Ala Pro Ser Thr Cys Ser Lys Pro Thr
    210                 215                 220

<210> SEQ ID NO 34
<211> LENGTH: 224
<212> TYPE: PRT
<213> ORGANISM: Artificial Sequence
<220> FEATURE:
<223> OTHER INFORMATION: Synthetic Construct

<400> SEQUENCE: 34

Gln Glu Gln Leu Lys Glu Ser Gly Gly Arg Leu Val Ala Pro Gly Thr
1               5                   10                  15

Pro Leu Thr Leu Thr Cys Thr Val Ser Gly Phe Asp Ile Ser Asp Tyr
            20                  25                  30

Ala Met Ile Trp Val Arg Gln Ala Pro Gly Lys Gly Leu Glu Trp Ile
        35                  40                  45

Gly Ile Ile Tyr Gly Val Ile Asn Asp Leu Ala Tyr Ala Lys Trp Ala
    50                  55                  60

Lys Gly Arg Phe Thr Ile Ser Arg Thr Ser Thr Thr Val Asp Leu Lys
65                  70                  75                  80

Ile Thr Ser Pro Thr Thr Glu Asp Thr Ala Thr Tyr Phe Cys Ala Arg
                85                  90                  95

Gly Tyr Gly Ser Met Asp Gly Tyr Asp Arg Leu Asn Leu Trp Gly Gln
            100                 105                 110

Gly Thr Leu Val Thr Val Ser Ser Gly Gln Pro Lys Gly Pro Ser Val
        115                 120                 125

Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Ala Thr Asn
        195                 200                 205

Thr Lys Val Asp Lys Thr Val Ala Pro Ser Thr Cys Ser Lys Pro Thr
    210                 215                 220

```
<210> SEQ ID NO 35
<211> LENGTH: 222
<212> TYPE: PRT
<213> ORGANISM: Artificial Sequence
<220> FEATURE:
<223> OTHER INFORMATION: Synthetic Construct

<400> SEQUENCE: 35

Gln Ser Val Glu Glu Ser Gly Gly Arg Leu Val Thr Pro Gly Thr Pro
1               5                   10                  15

Leu Thr Leu Thr Cys Thr Val Ser Ala Phe Ser Leu Ser Thr Tyr Thr
            20                  25                  30

Ile Asn Trp Val Arg Gln Ala Pro Gly Lys Gly Leu Glu Trp Ile Gly
        35                  40                  45

Asp Ile Trp Ser Asp Gly Asn Thr Tyr Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Ser
                85                  90                  95

Trp Asp Thr Ser Ile Tyr Tyr Gly Leu Asp Leu Trp Gly Gln Gly Thr
            100                 105                 110

Leu Val Thr Val Ser Ser Gly Gln Pro Lys Gly Pro Ser Val Phe Pro
        115                 120                 125

Leu Ala Pro Cys Cys Gly Asp Thr Pro Ser Ser Thr Val Thr Leu Gly
    130                 135                 140

Cys Leu Val Lys Gly Tyr Leu Pro Glu Pro Val Thr Val Thr Trp Asn
145                 150                 155                 160

Ser Gly Thr Leu Thr Asn Gly Val Arg Thr Phe Pro Ser Val Arg Gln
                165                 170                 175

Ser Ser Gly Leu Tyr Ser Leu Ser Ser Val Val Ser Val Thr Ser Ser
            180                 185                 190

Ser Gln Pro Val Thr Cys Asn Val Ala His Pro Ala Thr Asn Thr Lys
        195                 200                 205

Val Asp Lys Thr Val Ala Pro Ser Thr Cys Ser Lys Pro Thr
    210                 215                 220

<210> SEQ ID NO 36
<211> LENGTH: 222
<212> TYPE: PRT
<213> ORGANISM: Artificial Sequence
<220> FEATURE:
<223> OTHER INFORMATION: Synthetic Construct

<400> SEQUENCE: 36

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Thr
            20                  25                  30

Met Asn Trp Val Arg Gln Ala Pro Gly Lys Gly Leu Glu Trp Ile Gly
        35                  40                  45

Asp Ile Tyr Thr Asp Gly Asn Thr Tyr Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Ser
                85                  90                  95
```

Trp Asp Ala Ser Ser Tyr Tyr Gly Leu Asp Leu Trp Gly Gln Gly Thr
            100                 105                 110

Leu Val Thr Val Ser Ser Gly Gln Pro Lys Gly Pro Ser Val Phe Pro
            115                 120                 125

Leu Ala Pro Cys Cys Gly Asp Thr Pro Ser Ser Thr Val Thr Leu Gly
            130                 135                 140

Cys Leu Val Lys Gly Tyr Leu Pro Glu Pro Val Thr Val Thr Trp Asn
145                 150                 155                 160

Ser Gly Thr Leu Thr Asn Gly Val Arg Thr Phe Pro Ser Val Arg Gln
                165                 170                 175

Ser Ser Gly Leu Tyr Ser Leu Ser Val Val Ser Val Thr Ser Ser
            180                 185                 190

Ser Gln Pro Val Thr Cys Asn Val Ala His Pro Ala Thr Asn Thr Lys
            195                 200                 205

Val Asp Lys Thr Val Ala Pro Ser Thr Cys Ser Lys Pro Thr
            210                 215                 220

<210> SEQ ID NO 37
<211> LENGTH: 222
<212> TYPE: PRT
<213> ORGANISM: Artificial Sequence
<220> FEATURE:
<223> OTHER INFORMATION: Synthetic Construct

<400> SEQUENCE: 37

Gln Ser Val Glu Glu Ser Gly Gly Arg Leu Val Thr Pro Gly Thr Pro
1               5                   10                  15

Leu Thr Leu Thr Cys Thr Val Ser Ala Cys Ser Leu Tyr His Cys Thr
            20                  25                  30

Met Asn Trp Val Arg Gln Ala Pro Gly Lys Gly Leu Glu Trp Ile Gly
            35                  40                  45

Asp Ile Tyr Thr Asp Gly Asn Thr Tyr Tyr Ala Asn Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Ser
                85                  90                  95

Trp Asp Ala Ser Ser Tyr Tyr Gly Leu Asp Leu Trp Gly Gln Gly Thr
            100                 105                 110

Leu Val Thr Val Ser Ser Gly Gln Pro Lys Gly Pro Ser Val Phe Pro
            115                 120                 125

Leu Ala Pro Cys Cys Gly Asp Thr Pro Ser Ser Thr Val Thr Leu Gly
            130                 135                 140

Cys Leu Val Lys Gly Tyr Leu Pro Glu Pro Val Thr Val Thr Trp Asn
145                 150                 155                 160

Ser Gly Thr Leu Thr Asn Gly Val Arg Thr Phe Pro Ser Val Arg Gln
                165                 170                 175

Ser Ser Gly Leu Tyr Ser Leu Ser Val Val Ser Val Thr Ser Ser
            180                 185                 190

Ser Gln Pro Val Thr Cys Asn Val Ala His Pro Ala Thr Asn Thr Lys
            195                 200                 205

Val Asp Lys Thr Val Ala Pro Ser Thr Cys Ser Lys Pro Thr
            210                 215                 220

<210> SEQ ID NO 38

```
<211> LENGTH: 23
<212> TYPE: PRT
<213> ORGANISM: Artificial Sequence
<220> FEATURE:
<223> OTHER INFORMATION: Synthetic Construct

<400> SEQUENCE: 38

Ala Ala Val Leu Thr Gln Thr Pro Ser Pro Val Ser Ala Ala Val Gly
1               5                   10                  15
Gly Thr Val Thr Ile Ser Cys
            20

<210> SEQ ID NO 39
<211> LENGTH: 23
<212> TYPE: PRT
<213> ORGANISM: Artificial Sequence
<220> FEATURE:
<223> OTHER INFORMATION: Synthetic Construct

<400> SEQUENCE: 39

Ala Ile Lys Met Thr Gln Thr Pro Ser Ser Val Ser Ala Ala Val Gly
1               5                   10                  15
Gly Thr Val Thr Ile Asn Cys
            20

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Trp Phe Gln Lys Lys Pro Gly Gln Pro Pro Lys Leu Leu Ile Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic Construct

<400> SEQUENCE: 41

Trp Tyr Gln Gln Lys Pro Gly Gln Pro Pro Lys Leu Leu Ile Tyr
1               5                   10                  15

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Gly Val Ser Ser Arg Phe Ser Gly Ser Gly Ser Gly Thr His Phe Thr
1               5                   10                  15
Leu Thr Ile Ser Gly Val Gln Cys Asp Asp Ala Ala Thr Tyr Tyr Cys
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct
```

<400> SEQUENCE: 43

Gly Val Ser Ser Arg Phe Thr Gly Ser Gly Ser Gly Thr Glu Tyr Thr
1               5                   10                  15

Leu Thr Ile Ser Gly Val Gln Cys Asp Asp Ala Ala Thr Tyr Tyr Cys
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Synthetic Construct

<400> SEQUENCE: 44

Gly Val Ser Ser Arg Phe Lys Gly Ser Gly Ser Gly Thr Glu Tyr Thr
1               5                   10                  15

Leu Thr Ile Ser Gly Val Gln Cys Asp Asp Ala Ala Thr Tyr Tyr Cys
            20                  25                  30

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Phe Gly Gly Gly Thr Glu Val Val Val Lys
1               5                   10

<210> SEQ ID NO 46
<211> LENGTH: 30
<212> TYPE: PRT
<213> ORGANISM: Artificial Sequence
<220> FEATURE:
<223> OTHER INFORMATION: Synthetic Construct

<400> SEQUENCE: 46

Gln Glu Gln Leu Lys Glu Ser Gly Gly Arg Leu Val Ala Pro Gly Thr
1               5                   10                  15

Pro Leu Thr Leu Thr Cys Thr Val Ser Gly Phe Asp Ile Ser
            20                  25                  30

<210> SEQ ID NO 47
<211> LENGTH: 29
<212> TYPE: PRT
<213> ORGANISM: Artificial Sequence
<220> FEATURE:
<223> OTHER INFORMATION: Synthetic Construct

<400> SEQUENCE: 47

Gln Ser Val Glu Glu Ser Gly Gly Arg Leu Val Thr Pro Gly Thr Pro
1               5                   10                  15

Leu Thr Leu Thr Cys Thr Val Ser Ala Phe Ser Leu Ser
            20                  25

<210> SEQ ID NO 48
<211> LENGTH: 29
<212> TYPE: PRT
<213> ORGANISM: Artificial Sequence
<220> FEATURE:
<223> OTHER INFORMATION: Synthetic Construct

<400> SEQUENCE: 48

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 49
<211> LENGTH: 29
<212> TYPE: PRT
<213> ORGANISM: Artificial Sequence
<220> FEATURE:
<223> OTHER INFORMATION: Synthetic Construct

<400> SEQUENCE: 49

Gln Ser Val Glu Glu Ser Gly Gly Arg Leu Val Thr Pro Gly Thr Pro
1               5                   10                  15

Leu Thr Leu Thr Cys Thr Val Ser Ala Cys Ser Leu Tyr
            20                  25

<210> SEQ ID NO 50
<211> LENGTH: 14
<212> TYPE: PRT
<213> ORGANISM: Artificial Sequence
<220> FEATURE:
<223> OTHER INFORMATION: Synthetic Construct

<400> SEQUENCE: 50

Trp Val Arg Gln Ala Pro Gly Lys Gly Leu Glu Trp Ile Gly
1               5                   10

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct

<400> SEQUENCE: 51

Lys Gly Arg Phe Thr Ile Ser Arg Thr Ser Thr Thr Val Asp Leu Lys
1               5                   10                  15

Ile Thr Ser Pro Thr Thr Glu Asp Thr Ala Thr Tyr Phe Cys Ala Arg
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic Construct

<400> SEQUENCE: 52

Lys Gly Arg Phe Thr Ile Ser Lys Thr Ser Thr Thr Val Asp Leu Lys
1               5                   10                  15

Ile Thr Ser Pro Thr Thr Glu Asp Thr Ala Thr Tyr Phe Cys Ala Arg
            20                  25                  30

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Trp Gly Gln Gly Thr Leu Val Thr Val Ser Ser

<210> SEQ ID NO 54
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Hypusine modified with (PEG)6-Cysteine
      at carboxy terminus

<400> SEQUENCE: 54

Xaa
1

<210> SEQ ID NO 55
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Hypusine
<220> FEATURE:
<221> NAME/KEY: VARIANT
<222> LOCATION: 7
<223> OTHER INFORMATION: Xaa = Glycine modified with (PEG)6-Cysteine
      at carboxy terminus

<400> SEQUENCE: 55

Gly Ser Gly Xaa Gly Ser Xaa
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Glycine modified with biotin-(PEG)6
      at amino terminus
<220> FEATURE:
<221> NAME/KEY: VARIANT
<222> LOCATION: 4
<223> OTHER INFORMATION: Xaa = Hypusine

<400> SEQUENCE: 56

Xaa Ser Gly Xaa Gly Ser Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Glycine modified with biotin-(PEG)6
      at amino terminus
<220> FEATURE:
<221> NAME/KEY: VARIANT
<222> LOCATION: 4

```
<223> OTHER INFORMATION: Xaa = Deoxyhypusine

<400> SEQUENCE: 57

Xaa Ser Gly Xaa Gly Ser Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Glycine modified with biotin-(PEG)6
      at amino terminus

<400> SEQUENCE: 58

Xaa Ser Gly Lys Gly Ser Gly
1               5

<210> SEQ ID NO 59
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Serine modified with biotin-(PEG)6
      at amino terminus
<220> FEATURE:
<221> NAME/KEY: VARIANT
<222> LOCATION: 7
<223> OTHER INFORMATION: Xaa = Hypusine

<400> SEQUENCE: 59

Xaa Thr Ser Lys Thr Gly Xaa His Gly His Ala Lys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Serine modified with biotin-(PEG)6
      at amino terminus
<220> FEATURE:
<221> NAME/KEY: VARIANT
<222> LOCATION: 7
<223> OTHER INFORMATION: Xaa = Deoxyhypusine

<400> SEQUENCE: 60

Xaa Thr Ser Lys Thr Gly Xaa His Gly His Ala Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

```
<223> OTHER INFORMATION: Xaa = Serine modified with biotin-(PEG)6
      at amino terminus

<400> SEQUENCE: 61

Xaa Thr Ser Lys Thr Gly Lys His Gly His Ala Lys
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Biotinylated glycine
<220> FEATURE:
<221> NAME/KEY: VARIANT
<222> LOCATION: 8
<223> OTHER INFORMATION: Xaa = Hypusine

<400> SEQUENCE: 62

Xaa Gly Asp Glu Glu Ala Leu Xaa Gln Leu Ala Glu Trp Val Ser
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Biotinylated glycine

<400> SEQUENCE: 63

Xaa Gly Asp Glu Glu Ala Leu Lys Gln Leu Ala Glu Trp Val Ser
1               5                   10                  15

<210> SEQ ID NO 64
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Biotinylated glycine
<220> FEATURE:
<221> NAME/KEY: VARIANT
<222> LOCATION: 7
<223> OTHER INFORMATION: Xaa = Hypusine
<220> FEATURE:
<221> NAME/KEY: VARIANT
<222> LOCATION: 12
<223> OTHER INFORMATION: Xaa = Hypusine
<220> FEATURE:
<221> NAME/KEY: VARIANT
<222> LOCATION: 17
<223> OTHER INFORMATION: Xaa = Hypusine

<400> SEQUENCE: 64

Xaa Gly Ala Ala Ala Ala Xaa Ala Ala Ala Ala Xaa Ala Ala Ala Ala
1               5                   10                  15

Xaa Ala

<210> SEQ ID NO 65
```

```
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Biotinylated glycine
<220> FEATURE:
<221> NAME/KEY: VARIANT
<222> LOCATION: 7
<223> OTHER INFORMATION: Xaa = Hypusine
<220> FEATURE:
<221> NAME/KEY: VARIANT
<222> LOCATION: 17
<223> OTHER INFORMATION: Xaa = Hypusine

<400> SEQUENCE: 65

Xaa Gly Ala Ala Ala Ala Xaa Ala Ala Ala Ala Lys Ala Ala Ala Ala
1               5                   10                  15

Xaa Ala

<210> SEQ ID NO 66
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Hypusine
<220> FEATURE:
<221> NAME/KEY: VARIANT
<222> LOCATION: 18
<223> OTHER INFORMATION: Xaa = Biotinylated glycine

<400> SEQUENCE: 66

Gly Trp Xaa Pro Met Ser Arg Ser Ser Gly Arg Val Tyr Tyr Phe Asn
1               5                   10                  15

Gly Xaa

<210> SEQ ID NO 67
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 18
<223> OTHER INFORMATION: Xaa = Biotinylated glycine

<400> SEQUENCE: 67

Gly Trp Lys Pro Met Ser Arg Ser Ser Gly Arg Val Tyr Tyr Phe Asn
1               5                   10                  15

Gly Xaa

<210> SEQ ID NO 68
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Biotinylated glycine
<220> FEATURE:
```

```
<221> NAME/KEY: VARIANT
<222> LOCATION: 8
<223> OTHER INFORMATION: Xaa = Hypusine

<400> SEQUENCE: 68

Xaa Gly Leu Leu Glu Leu Asp Xaa Trp Ala Ser Leu Trp
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Biotinylated glycine

<400> SEQUENCE: 69

Xaa Gly Leu Leu Glu Leu Asp Lys Trp Ala Ser Leu Trp
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Hypusine

<400> SEQUENCE: 70

Gly Ser Gly Xaa Gly Ser Gly
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Deoxyhypusine

<400> SEQUENCE: 71

Gly Ser Gly Xaa Gly Ser Gly
1               5

<210> SEQ ID NO 72
<211> LENGTH: 12
<212> TYPE: PRT
<213> ORGANISM: Artificial Sequence
<220> FEATURE:
<223> OTHER INFORMATION: Synthetic Construct

<400> SEQUENCE: 72

Gln Gln Gly Tyr Thr Ser Thr Asn Val Asn Asn Ala
1               5                   10
```

# ANTI-HYPUSINE ANTIBODIES AND USES THEREOF

CROSS-REFERENCE TO RELATED APPLICATIONS

This application is a continuation of International Application No. PCT/US2016/049127, filed Aug. 26, 2016, which claims the priority benefit of U.S. Provisional Patent Application No. 62/211,642, filed Aug. 28, 2015, the content of each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392034401SEQLIST.txt, date recorded: Jan. 22, 2018, size: 42 KB).

FIELD OF THE INVENTION

The present invention relates to methods and reagents for detecting and isolating polypeptides containing hypusine and/or deoxyhypusine.

BACKGROUND

The unusual amino acid, hypusine (Nε-(4-amino-2-hydroxybutyl)-lysine), is a post-translationally modified lysine. Eukaryotic translation initiation factor 5A (eIF5A) is currently the only naturally occurring protein that has been reported to contain hypusine (Cooper et al., *Cell.*, 29:791-797, 1982; Park et al., *PNAS*, 78:2869-2873, 1981). The modification of eIF5A with hypusine involves two enzymatic reactions. Firstly, deoxyhypusine synthase (DHS) transfers the butylamine moiety of spermidine to the ε-amino group of one specific lysine residue of eIF5A (residue K50 on human eIF5A), resulting in deoxyhypusine. Secondly, hypusine biosynthesis is completed by hydroxylation catalyzed by deoxyhypusine hydroxylase (DOHH) (Park et al., *PNAS*, 103:51-56, 2006). Hypusinated eIF5A appears to be the active form since most known functions of eIF5A, such as translational elongation, RNA binding, and ribosome association, are dependent upon hypusination (Jao, et al., *J. Cell. Biochem.*, 97:583-598, 2006; Saini et al., *Nature*, 459:118-121, 2009). The amino acid sequence of eIF5A, as well as DHS and DOHH, is highly conserved throughout eukaryotes, and deoxyhypusine/hypusine is absolutely required for cell proliferation in archaea and eukaryotes (Jansson et al., *J. Bacteriol.*, 182:1158-1161, 2000; Park et al., *Biol. Signals.*, 6:115-123). The lysine residue (K50) that is converted to hypusine and the primary sequences surrounding this modification site in eIF5A are highly conserved, underscoring the importance of this unusual protein modification throughout eukaryotic evolution. However, no other hypusinated proteins besides eIF5A have been reported in spite of extensive efforts to identify them (Cooper et al., *Cell.*, 29:791-797, 1982; Sievert et al., *Mol. Cell Proteomics*, 11:1289-1305, 2012).

Antibody-based affinity purification is widely used to enrich low abundance proteins for identification. This approach has been successfully used for global analysis of protein lysine acetylation (Kim et al., *Mol. Cell.*, 23:607-618, 2006; Zhang et al., *Mol. Cell Proteomics*, 8:215-225, 2009), arginine methylation (Ong et al., *Nat. Methods.*, 1:119-126, 2004), and tyrosine phosphorylation (Pandey et al., *PNAS*, 97:179-184, 2000; Rikova et al., *Cell*, 131:1190-1203, 2007). However, high-affinity post-translational modification (PTM) specific and sequence-independent antibodies are not easy to obtain for PTMs of interest, because of the small size of PTMs. In addition, there is no previously reported complex structure of a PTM specific context-independent antibody. Several anti-hypusine or anti-deoxyhypusine antibodies have been reported including polyclonal (Clement et al., *Eur. J. Biochem.*, 270:4254-4263, 2003; Cracchiolo et al., *Gynecol. Oncol.*, 94:217-222, 2004) and monoclonal antibodies (Bergeron et al., *J. Med. Chem.*, 41(20):3888-3900, 1998). However, these antibodies were raised against eIF5A peptides and characterized against binding to eIF5A. Hence they may not be well suited for identifying novel hypusinated proteins with different sequences flanking hypusine. Furthermore, the polyclonal antibodies are not readily available and the sequences of the monoclonal antibodies have not been reported. As a result, radiolabeled spermidine and GC7 (a DHS inhibitor) are still the most frequently used tools for eIF5A functional studies. There remains a need for developing high affinity anti-hypusine antibodies that bind hypusine on polypeptides independently of the amino acid sequences flanking hypusine. Discovery of such anti-hypusine antibodies may allow for the identification and isolation of novel hypusinated polypeptides.

All references cited herein, including patent applications, patent publications, and scientific literature, are herein incorporated by reference in their entirety, as if each individual reference were specifically and individually indicated to be incorporated by reference

SUMMARY OF THE INVENTION

Provided herein are anti-hypusine antibodies, compositions comprising thereof, and methods of using the same.

Provided herein are pan anti-hypusine antibodies that bind to the posttranslational modification (PTM), hypusine, with minimal dependence on flanking amino acid sequences. The antibodies may bind to hypusine and deoxyhypusine or selectively to hypusine but not to deoxyhypusine.

In one aspect, provided herein is an isolated antibody that specifically binds to hypusine in a polypeptide, wherein the antibody binds to hypusine-containing polypeptides with different amino acid sequences flanking hypusine. In some embodiments, the antibody does not bind to deoxyhypusine in a polypeptide. In some embodiments, the antibody binds to deoxyhypusine in a polypeptide. In any of the embodiments herein, the antibody may exhibit a binding affinity ($K_D$) of 900 nM or less against the polypeptide containing hypusine. In a further embodiment, the antibody exhibits (i) a binding affinity ($K_D$) of 300 nM or less against the polypeptide containing hypusine and (ii) a binding affinity ($K_D$) of 200 nM or less against the polypeptide containing deoxyhypusine. In any of the embodiments herein, the antibody described herein can be a monoclonal antibody. In any of the embodiments herein, the antibody described herein can be an antigen-binding fragment. In some of the embodiments herein, the antibody comprises a heavy chain variable region and a light chain variable region, wherein the heavy chain variable region comprises (i) HVR-H1 comprising the amino acid sequence of SEQ ID NO:9, (ii) HVR-H2 comprising the amino acid sequence of SEQ ID NO:13 or 14, and (iii) HVR-H3 comprising the amino acid sequence of SEQ ID NO:17; and/or wherein the light chain variable region comprises (i) HVR-L1 comprising the amino acid sequence of SEQ ID NO:1 or 2, (ii) HVR-L2 comprising the amino acid sequence of SEQ ID NO:4 or 5, and (iii) HVR-L3 comprising the amino acid sequence of SEQ ID NO:7. In a further embodiment, the heavy chain variable region comprises a sequence having at least 90% sequence identity to the amino acid sequence of SEQ ID NO:24 or 25; and/or the light chain variable region comprises a sequence having at least 90% sequence identity to the amino acid sequence of SEQ ID NO:20 or 21. In some of the embodiments herein, the antibody comprises a heavy chain variable region and a light chain variable region, wherein the heavy chain variable region comprises (i) HVR-H1 comprising the amino acid sequence of SEQ ID NO:11 or 12, (ii) HVR-H2 comprising the amino acid sequence of SEQ ID NO:16, and (iii) HVR-H3 comprising the amino acid sequence of SEQ ID NO:19; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:8. In a further embodiment, the heavy chain variable region comprises a sequence having at least 95% sequence identity to the amino acid sequence of SEQ ID NO: 27 or 28; and/or the light chain variable region comprises a sequence having at least 95% sequence identity to the amino acid sequence of SEQ ID NO:23. In some of the embodiments herein, the antibody comprises a heavy chain variable region and a light chain variable region, wherein the heavy chain variable region comprises (i) HVR-H1 comprising the amino acid sequence of SEQ ID NO:10, (ii) HVR-H2 comprising the amino acid sequence of SEQ ID NO:15, and (iii) HVR-H3 comprising the amino acid sequence of SEQ ID NO:18; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:72. In a further embodiment, the heavy chain variable region comprises a sequence having at least 95% sequence identity to the amino acid sequence of SEQ ID NO: 26; and/or the light chain variable region comprises a sequence having at least 95% sequence identity to the amino acid sequence of SEQ ID NO:22. In some embodiments, the antibody is linked to a detection agent.

In one aspect, provided herein is an isolated antibody that binds to hypusine in a polypeptide, wherein the antibody comprises a heavy chain variable region and a light chain variable region, wherein the heavy chain variable region comprises (i) HVR-H1 comprising the amino acid sequence of SEQ ID NO:9, (ii) HVR-H2 comprising the amino acid sequence of SEQ ID NO:13 or 14, and (iii) HVR-H3 comprising the amino acid sequence of SEQ ID NO:17; and/or wherein the light chain variable region comprises (i) HVR-L1 comprising the amino acid sequence of SEQ ID NO:1 or 2, (ii) HVR-L2 comprising the amino acid sequence of SEQ ID NO:4 or 5, and (iii) HVR-L3 comprising the amino acid sequence of SEQ ID NO:7. In a further embodiment, the heavy chain variable region comprises the amino acid sequence of SEQ ID NO:24 or 25; and/or the light chain variable region comprises the amino acid sequence of SEQ ID NO:20 or 21. In yet a further embodiment, the heavy chain comprises the amino acid sequence of SEQ ID NO:33 or 34; and/or the light chain comprises the amino acid sequence of SEQ ID NO:29 or 30. In some embodiments, the antibody is linked to a detection agent.

In another aspect, provided herein is an isolated antibody that specifically binds to hypusine in a polypeptide, wherein the antibody comprises a heavy chain variable region and a light chain variable region, wherein the heavy chain variable region comprises (i) HVR-H1 comprising the amino acid sequence of SEQ ID NO:11 or 12, (ii) HVR-H2 comprising the amino acid sequence of SEQ ID NO:16, and (iii) HVR-H3 comprising the amino acid sequence of SEQ ID NO:19; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:8. In a further embodiment, the heavy chain variable region comprises the amino acid sequence of SEQ ID NO:27 or 28; and/or the light chain variable region comprises the amino acid sequence of SEQ ID NO:23. In yet a further embodiment, the heavy chain comprises the amino acid sequence of SEQ ID NO:36 or 37; and/or the light chain comprises the amino acid sequence of SEQ ID NO:32. In some embodiments, the antibody is linked to a detection agent.

In yet another aspect, provided herein is an isolated antibody that specifically binds to hypusine in a polypeptide, wherein the antibody comprises a heavy chain variable region and a light chain variable region, wherein the heavy chain variable region comprises (i) HVR-H1 comprising the amino acid sequence of SEQ ID NO:10, (ii) HVR-H2 comprising the amino acid sequence of SEQ ID NO:15, and (iii) HVR-H3 comprising the amino acid sequence of SEQ ID NO:18; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:72. In a further embodiment, the heavy chain variable region comprises the amino acid sequence of SEQ ID NO:26; and/or the light chain variable region comprises the amino acid sequence of SEQ ID NO:22. In yet a further embodiment, the heavy chain comprises the amino acid sequence of SEQ ID NO:35; and/or the light chain comprises the amino acid sequence of SEQ ID NO:31. In some embodiments, the antibody is linked to a detection agent.

In another aspect, provided herein is an isolated nucleic acid comprising a sequence encoding any antibody described above and herein. In yet another aspect, provided herein is a vector comprising a nucleic acid described herein. In one embodiment, the vector is an expression vector. In yet another aspect, provided herein is a host cell comprising a nucleic acid described herein. In some embodiments, the host cell expresses and produces the antibody.

In another aspect, provided herein is a method of producing an antibody comprising culturing any host cell described herein and comprising a nucleic acid described herein under a condition that produces the antibody. In some embodiments, the method further comprises recovering the antibody produced by the host cell.

In one aspect, provided herein is a method for detecting a hypusine-containing polypeptide in a sample comprising the steps of: (a) contacting the sample with an antibody described above and herein; and (b) detecting the antibody bound to the polypeptide in the sample. In one embodiment, the antibody is linked to a detection agent. In one embodiment, the antibody bound to the polypeptide is detected by using a secondary agent. In a further embodiment, the detection agent is a chemiluminescent label, a chromophore, a fluorophore, a magnetic particle, a dye, a radiolabel, or an enzyme. In some of the embodiments of the methods herein, the detection is by one or more assays selected from the group consisting of enzyme-linked immunosorbent assay, radioimmunoassay, immunoprecipitation, chromatography, immunohistochemistry, immunofluorescence, surface plasmon resonance, fluorescence-activated cell sorting and mass spectrometry. In any of the embodiments herein, the sample can be a biological sample. In a further embodiment, the biological sample comprises a cell or tissue. In another further embodiment, the biological sample is a fluid.

In yet another aspect, provided herein is a method for isolating a hypusine-containing polypeptide in a sample comprising the steps of: (a) contacting the sample with an antibody described above and herein; (b) isolating the polypeptide bound to the antibody. In a further embodiment, the antibody is immobilized to a solid surface. In any of the embodiments herein, the sample can be a biological sample. In a further embodiment, the biological sample comprises a cell or tissue. In another further embodiment, the biological sample is a fluid.

In another aspect, provided herein is a composition comprising an antibody described above and herein.

In one aspect, provided herein is a kit comprising an antibody described above and herein or a composition thereof. In an embodiment, the kit further comprises one or more agents for use of the antibody in a method for detecting a hypusine-containing polypeptide in a sample. In another embodiment, the kit further comprising one or more agents for use of the antibody in a method for isolating a hypusine-containing polypeptide in a sample.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIGS. 1A-1D is a diagram showing the heavy chain and light chain variable domains of pan anti-hypusine antibodies. FIG. 1A) Light chain variable regions of mAbHpu24 (SEQ ID NO:20) and mAbHpu24.B (SEQ ID NO:21); FIG. 1B) Heavy chain variable regions of mAbHpu24 (SEQ ID NO:24) and mAbHpu24.B (SEQ ID NO:25); FIG. 1C) Light chain variable regions of mAbHpu98 (SEQ ID NO:23), mAbHpu98.61 (SEQ ID NO:23) and mAbHpu91 (SEQ ID NO:22); and FIG. 1D) Heavy chain variable regions of mAbHpu98 (SEQ ID NO:27), mAbHpu98.61 (SEQ ID NO:28) and mAbHpu91 (SEQ ID NO:26). Sequence differences between the parent antibody (mAbHpu24 or mAbHpu98) and the affinity-matured variant (mAbHpu24.B or mAbHpu98.61), are highlighted. Sequence differences between mAbHpu91 and closely related mAbHpu98 and mAbHpu98.61 antibodies are also highlighted.

FIGS. 2A-2C is a series of panels showing that mAbHpu24, mAbHpu91 and mAbHpu98 specifically recognize hypusine. FIG. 2A) Anti-hypusine antibodies bound to hypusinated peptides independent of flanking sequences as shown by ELISA of unpurified hybridoma supernatants. The sequences of peptides (P1 to P6) are provided in Table 1. Solid bar indicates data for anti-hypusine antibody binding to hypusinated peptide. Solid bar with asterisk (*) indicates data for anti-hypusine antibody binding to non-hypusinated peptide. FIG. 2B) Construct design for the overexpression of matured eIF5A in 293 cells using a fusion protein of enzymes DHS and DOHH required for hypusination. FIG. 2C) Anti-hypusine antibodies specifically bound to hypusine in the native intact protein eIF5A as shown by Western blot analysis.

FIGS. 3A-3C is a series of panels showing specificity characterization of pan anti-hypusine antibodies. FIG. 3A) Structures of hypusine and deoxyhypusine. FIG. 3B) FabHpu24 and FabHpu91 exclusively interacted with hypusine, while mAbHpu98 was able to bind both hypusine and deoxyhypusine. Binding analysis were undertaken using Octet RED instrument by immobilizing biotinylated P1 hypusine-containing peptide (shown as 1 or magenta), P1-deoxyhypusinated peptide (shown as 2 or orange) or the non-hypusinated peptide (shown as 3 or blue) on streptavidin biosensors and then dipping into 200 nM of anti-Hpu Fabs. FIG. 3C) FabHpu98 residue $V_H$Y52 was necessary for dual binding to deoxyhypusine and hypusine. P1-Hpu indicates P1 hypusine-containing peptide (shown as 1 or magenta), P1-deoxy indicates P1-deoxyhypusinated peptide (shown as 2 or orange) and P1 indicates non-hypusinated peptide (shown as 3 or blue).

FIG. 4A) Representative biosensor sensorgrams for FabHpu24 or FabHpu24.B binding to immobilized P1-Hpu peptide or P1-deoxyHpu peptide. FIG. 4B) Representative biosensor sensorgrams for FabHpu98 or FabHpu98.61 binding to immobilized P1-Hpu peptide or P1-deoxyHpu peptide. The Fab was injected in a range of concentrations: 200 nM (red), 66.7 nM (orange), 22 nM (green), 7.4 nM (blue), 2.4 nM (purple), and the fitted curves are shown (black).

FIGS. 7A-7B is a Coomassie blue stained gel showing that affinity-matured anti-hypusine antibodies give better recovery of hypusinated protein, eIF5A. FIG. 7A) Coomassie blue staining showing that more endogenous eIF5A was immunoprecipitated by mAbHpu24.B than mAbHpu24. FIG. 7B) Coomassie blue staining showing that more endogenous eIF5A was pulled down by mAbHpu98.61 than mAbHpu98.

FIG. 8A) Simulated annealing mFo-dFc omit map (displayed at 3.0× RMSD) showing the electron density of hypusine in complex with FabHpu24. FIG. 8B) simulated annealing mFo-dFc omit map (displayed at 3.0×RMSD) showing the electron density of hypusine in complex with FabHpu98. Arrow indicates hypusine containing peptide.

FIG. 9A) FabHpu24 Fab $V_L$ (salmon, right lobe) and $V_H$ (blue, left lobe) domains complexed to the hypusine-containing C1 peptide (yellow, indicated by straight arrow). FIG. 9B) $V_L$ (violet, left lobe) and $V_H$ (teal, right lobe) of FabHpu98 Fab complexed to the hypusine-containing C1 peptide (yellow, indicated by straight arrow).

FIG. 10A) Extensive hydrogen bond network of FabHpu24 with the hypusine-containing C1 peptide. Stereo views showing $V_H$ (blue, left lobe), $V_L$ (salmon, right lobe) and C1 peptide (yellow, indicated by arrow) with putative hydrogen bonds indicated by dashed lines (orange) with lengths in Ångströms as indicated. FIG. 10B) Extensive hydrogen bond network of FabHpu98 with peptide C1 with $V_H$ (magenta, left lobe), $V_L$ (teal, right lobe) and C1 peptide (yellow, indicated by arrow).

FIG. 11A) The isomorphous Fo-Fo difference map showing the position of the hydroxyl group of hypusine and shift of $V_H$ Y52 side chain, displayed at 5.0×rmsd. FIG. 11B) In FabHpu98: hypusine complex, the hydroxyl group of hypusine forms hydrogen bonds with both $V_L$ S94 and $V_H$ Y52. FIG. 11C) In FabHpu98: deoxyhypusine complex, $V_L$ S94 and $V_H$ Y52 form a hydrogen bond. Arrow indicates hypusine containing peptide.

FIGS. 12A-12D is a series of diagrams showing the structure of affinity-matured Fabs binding to hypusine. FIG. 12A) Comparison of FabHpu24 $V_L$ (salmon, right lobe) and $V_H$ (blue, left lobe) and FabHpu24.B $V_L$ (salmon, right lobe) and $V_H$ (green, left lobe) binding to C1 peptide (GSG-Hpu-GSG (SEQ ID NO: 70), yellow, indicated by arrow). Conformational change in CDR H2 and H3 increased contact area for hypusine interaction. FIG. 12B) Extensive hydrogen bond network of FabHpu24.B with the hypusine-containing peptide, C1. FIG. 12C) Comparison of FabHpu98 $V_L$ (violet, left section) and $V_H$ (cyan, right section) and FabHpu98.61 $V_L$ (violet, left section) and $V_H$ (green, right section) binding to C1 peptide (GSG-Hpu-GSG (SEQ ID NO: 70), indicated by arrow). FIG. 12D) T33 of FabHpu24.B makes additional H-bond with hypusine. Arrow indicates hypusine containing peptide.

DETAILED DESCRIPTION

I. Definitions

Figure 1C:
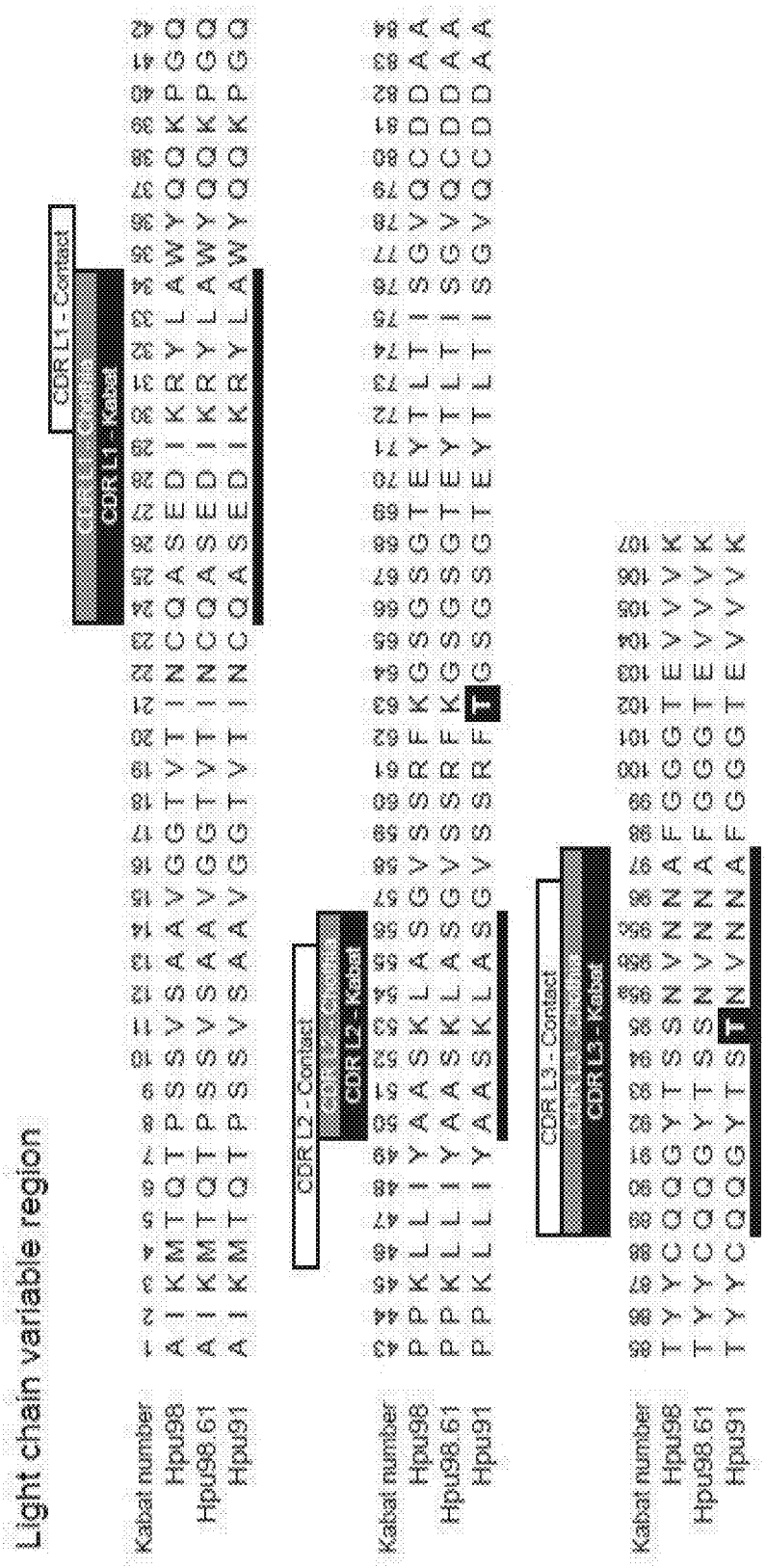
Figure 4A:
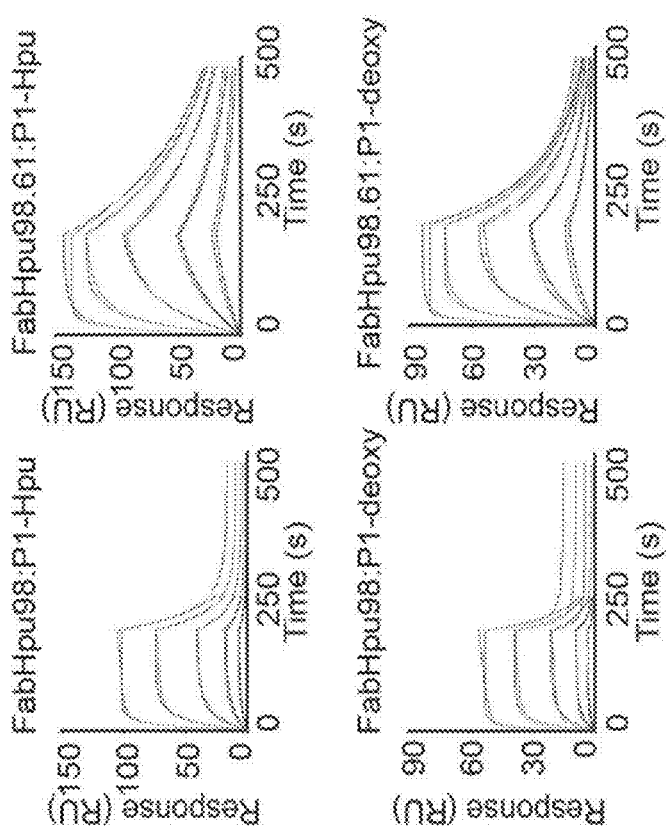
FIGS. 4A-4B is a series of graphs showing increased antigen binding by affinity-matured anti-hypusine antibodies.
Figure 4B:
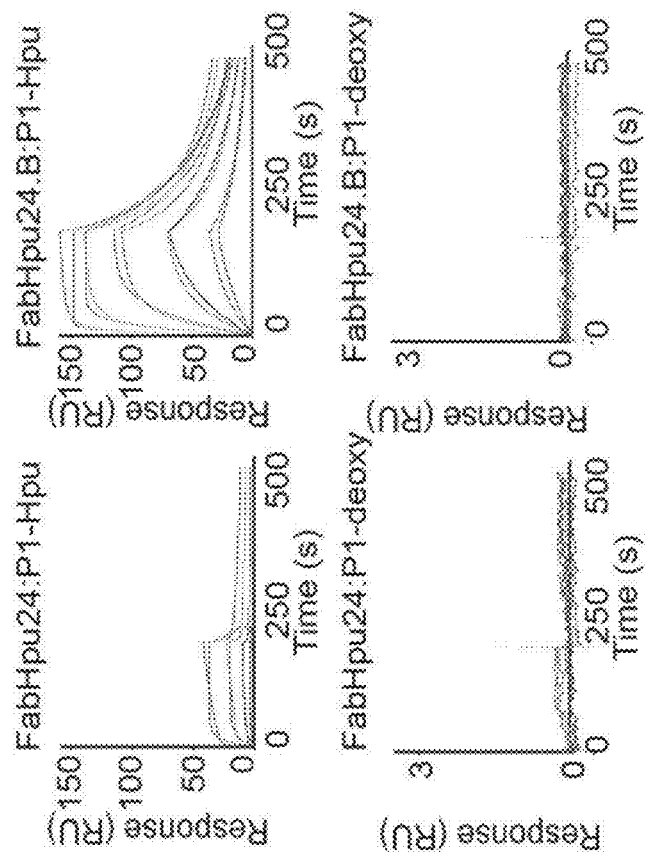
Figures 5A, 5B, 5C:
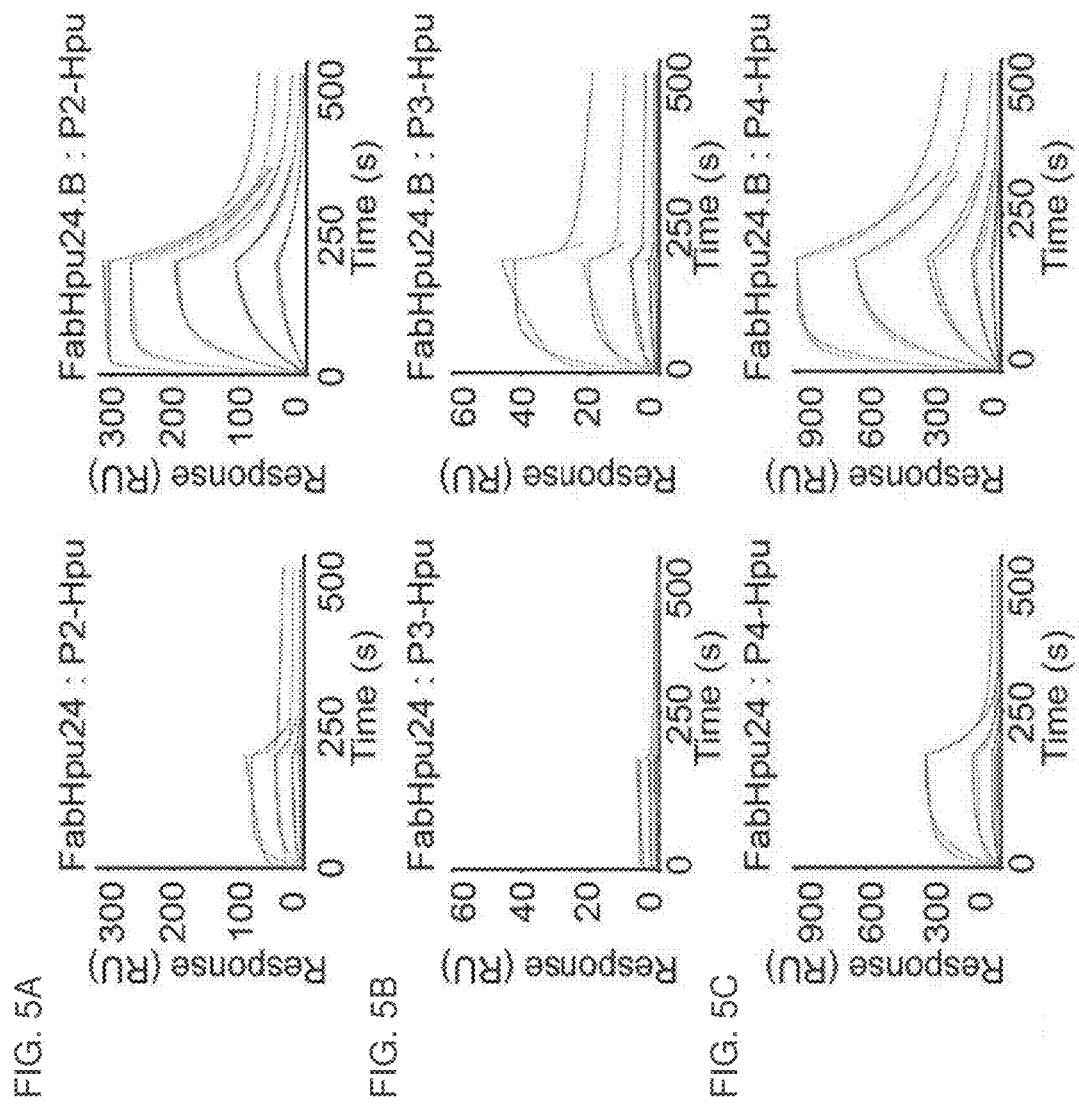
FIGS. 5A-5E is a series of graphs showing representative biosensor sensorgrams for FabHpu24 or FabHpu24.B binding to various hypusine-containing peptides. Representative biosensor sensorgrams for FabHpu24 or FabHpu24.B binding to immobilized FIG. 5A) P2-Hpu, FIG. 5B) P3-Hpu, FIG. 5C) P4-Hpu, FIG. 5D) P5-Hpu and FIG. 5E) P6-Hpu. The Fab was injected in a range of concentrations: 200 nM (red), 66.7 nM (orange), 22 nM (green), 7.4 nM (blue), 2.4 nM (purple), and the fitted curves are shown (black).
Figures 5D, 5E:
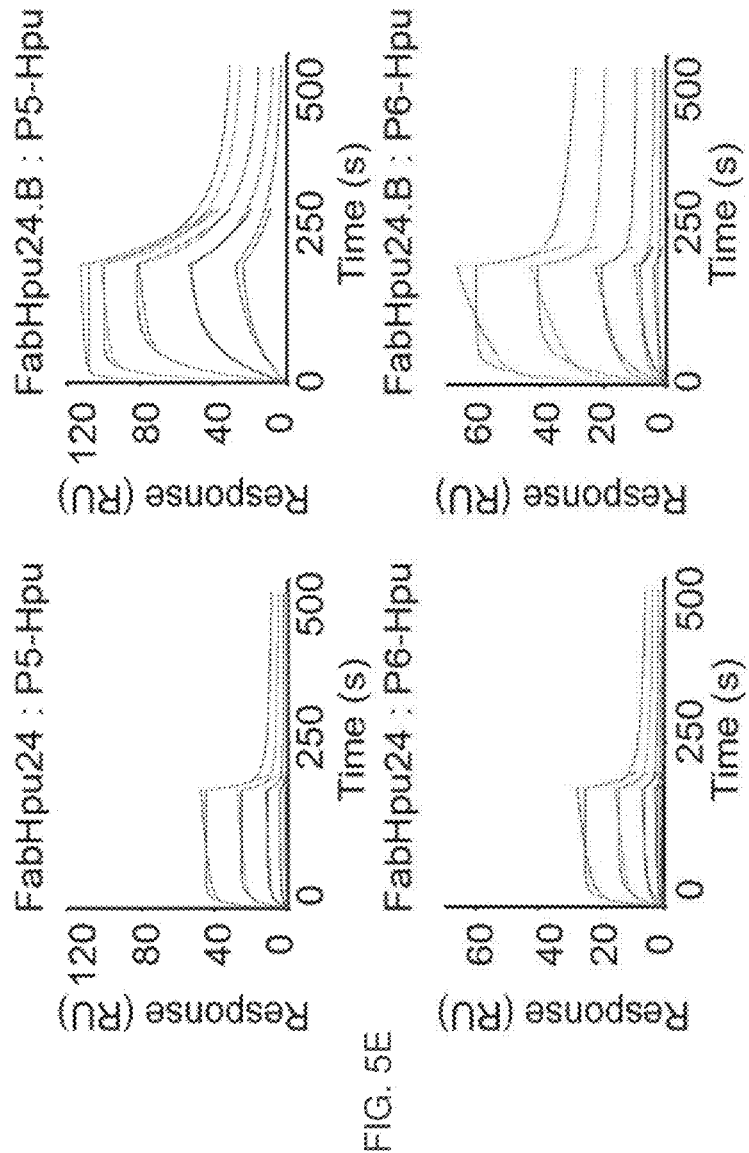
Figures 6A, 6B, 6C:
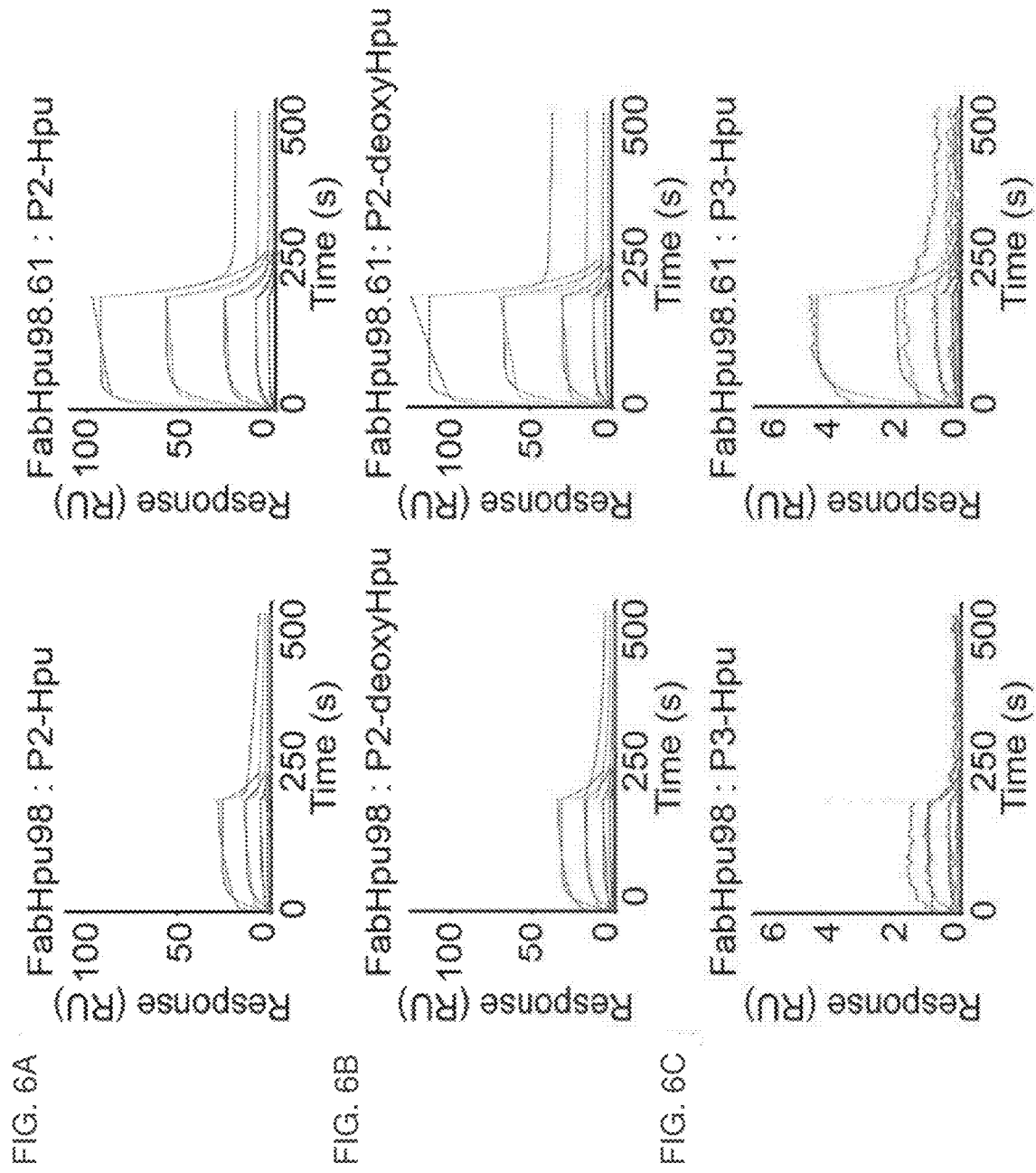
FIGS. 6A-6F is a series of graphs showing representative biosensor sensorgrams for FabHpu98 or FabHpu98.61 binding to various hypusine- or deoxyhypusine-containing peptides. Representative biosensor sensorgrams for FabHpu98 or FabHpu98.61 binding to immobilized FIG. 6A) P2-Hpu, FIG. 6B) P2-deoxyHpu, FIG. 6C) P3-Hpu, FIG. 6D) P4-Hpu, FIG. 6E) P5-Hpu and FIG. 6F) P6-Hpu. The Fab was injected in a range of concentrations: 200 nM (red), 66.7 nM (orange), 22 nM (green), 7.4 nM (blue), 2.4 nM (purple), and the fitted curves are shown (black).
Figures 6D, 6E, 6F:
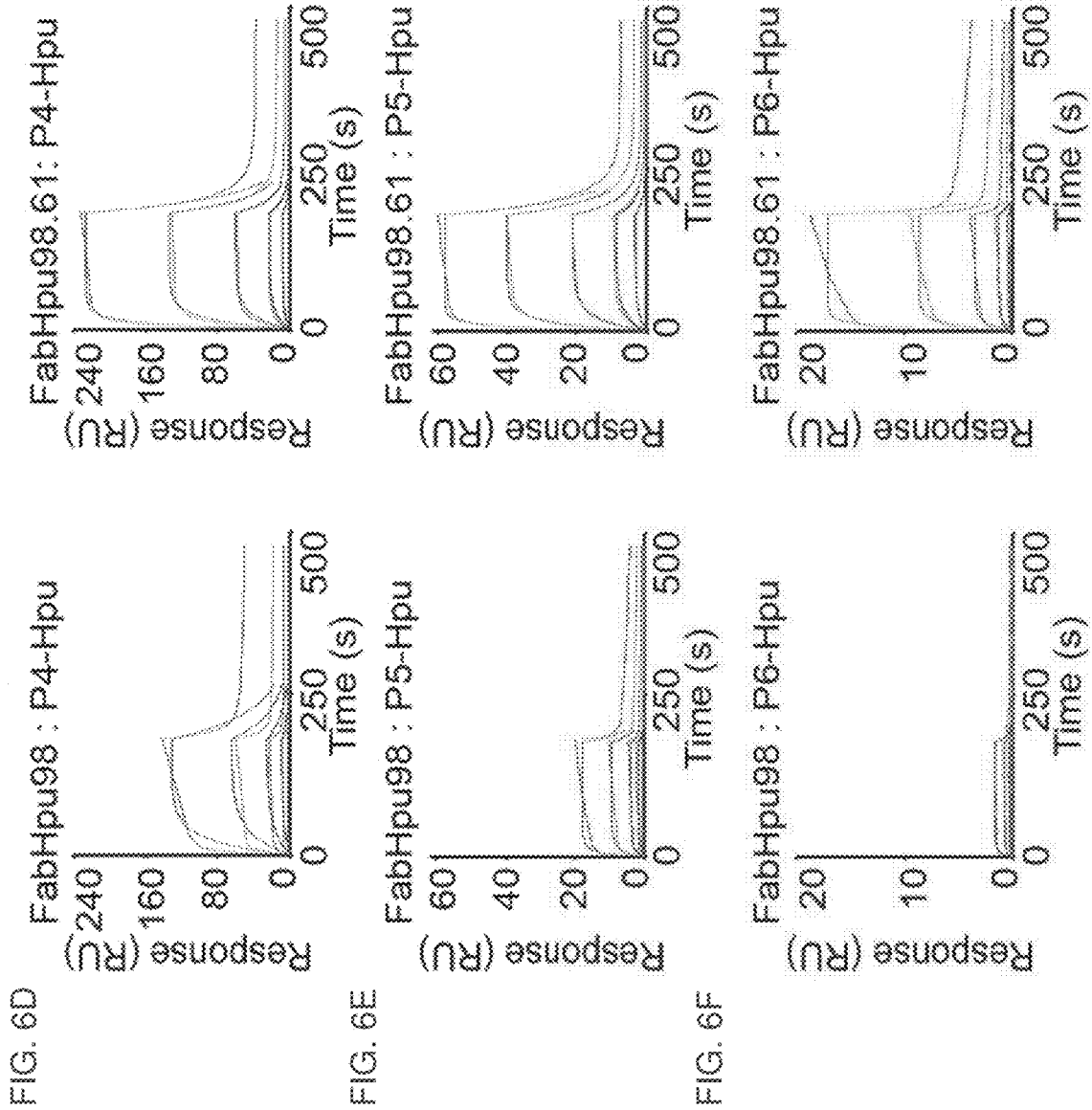

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

It is understood that aspects and embodiments of the invention described herein include "comprising," "consisting," and "consisting essentially of" aspects and embodiments.

The term "antibody" herein is used in the broadest sense and encompasses various antibody structures, including but not limited to monoclonal antibodies, polyclonal antibodies, multispecific antibodies (e.g., bispecific antibodies), humanized antibodies, human antibodies, chimeric antibodies and antibody fragments so long as they exhibit the desired antigen-binding activity.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-hypusine antibody" and "an antibody that binds to hypusine in a polypeptide" is used interchangeably to refer to an antibody that is capable of binding hypusine in a hypusine-containing polypeptide with sufficient affinity such that the antibody is useful as a detecting, diagnosing or isolating reagent for hypusine-containing polypeptides. In one embodiment, the extent of binding of an anti-hypusine antibody to a non-hypusinated polypeptide is less than about 10% of the binding of the anti-hypusine antibody to a hypusinated protein as measured, e.g., by a radioimmunoassay (RIA). In certain embodiments, an antibody that binds to hypusine in a hypusine-containing polypeptide has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In some embodiments, the anti-hypusine antibody also binds to deoxyhypusine in a polypeptide.

The terms "anti-deoxyhypusine antibody" and "an antibody that binds to deoxyhypusine in a polypeptide" is used interchangeably to refer to an antibody capable of binding deoxyhypusine in a deoxyhypusine-containing polypeptide with sufficient affinity such that the antibody is useful as a detecting, diagnosing or isolating reagent for deoxyhypusine-containing polypeptides. In some embodiments, the antibody that binds to deoxyhypusine also binds to hypusine in a polypeptide. In one embodiment, the extent of binding of an anti-deoxyhypusine antibody to a non-deoxyhypusinated polypeptide is less than about 10% of the binding of the antibody to a deoxyhypusinated polypeptide as measured, e.g., by a radioimmunoassay (RIA). In certain embodiments, an antibody that binds to deoxyhypusine in a deoxyhypusine-containing polypeptide has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In some embodiments, the anti-hypusine antibody binds to hypusine and deoxyhypusine on the same polypeptide (e.g., a polypeptide containing hypusine and deoxyhypusine). In some embodiments, the antibody binds to hypusine and deoxyhypusine on different polypeptides (e.g., a polypeptide containing hypusine and not deoxyhypusine and a polypeptide containing deoxyhypusine and not hypusine). In some embodiments, the anti-hypusine antibody does not bind to deoxyhypusine in a polypeptide.

Binding" or "specific binding" generally refers to binding between two molecules (such as between an antibody and one or more targets, an anti-hypusine antibody and hypusine or an anti-hypusine antibody and deoxyhypusine) with sufficient affinity. Preferably, the extent of binding of an antibody to an unrelated molecule is less than about 10% of the binding of the antibody to a target as measured, e.g., by a radioimmunoassay (RIA). In some embodiments, the antibody that binds to its target has a dissociation constant ($K_D$) of $\leq 1$ µM, $\leq 100$ nM, $\leq 10$ nM, $\leq 1$ nM, or $\leq 0.1$ nM.

The term "antibody binds to hypusine-containing polypeptide or deoxyhypusine-containing polypeptide with different amino acid sequences flanking hypusine" refers to antibodies which specifically recognize hypusine and/or deoxyhypusine in the context of variable surrounding peptide or protein sequences. Such antibodies bind to hypusine and/or deoxyhypusine in at least two polypeptides with different amino acid sequences flanking the hypusine or deoxyhypusine. In certain embodiments, such antibodies bind to hypusine and/or deoxyhypusine in a polypeptide with minimal dependence on the amino acid sequences surrounding hypusine and/or deoxyhypusine, e.g., the antibody binds to two or more polypeptides having different amino acid sequences surrounding hypusine and/or deoxyhypusine with less than a 25%, 20%, 15%, 10%, 7%, 5%, 2% or 1% change in affinity.

The terms "full length antibody," "intact antibody," and "whole antibody" are used herein interchangeably to refer to an antibody having a structure substantially similar to a native antibody structure or having heavy chains that contain an Fc region as defined herein.

An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

A "Fab" fragment contains a variable and constant domain of the light chain and a variable domain and the first constant domain (CH1) of the heavy chain. F(ab)'$_2$ antibody fragments comprise a pair of Fab fragments that are generally covalently linked near their carboxy termini by hinge cysteines. Other chemical couplings of antibody fragments are also known.

"Fv" is the minimum antibody fragment which contains a complete antigen-recognition and binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, NJ, 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, MD. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat   | Chothia | Contact |
|------|---------|---------|---------|
| L1   | L24-L34 | L26-L34 | L30-L36 |
| L2   | L50-L56 | L50-L56 | L46-L55 |
| L3   | L89-L97 | L91-L96 | L89-L96 |

-continued

| Loop | Kabat | Chothia | Contact |
|------|-------|---------|---------|
| H1 | H31-H35B | H26-H32 | H30-H35B (Kabat Numbering) |
| H1 | H31-H35 | H26-H32 | H30-H35 (Chothia Numbering) |
| H2 | H50-H65 | H53-H56 | H47-H58 |
| H3 | H95-H102 | H95-H102 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH.

Unless otherwise indicated, the variable-domain residues (HVR residues and framework region residues) are numbered according to Kabat et al., supra.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-hypusine antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In some embodiments, the host cell is isolated (i.e., separated from a component of its natural environment).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "package insert" is used to refer to instructions customarily included in commercial packages of reagent products that contain information about the usage of such reagent products.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "sample" or "biological sample", as used herein, refers to a composition that is obtained or derived from a subject, cell or tissue of interest. Samples include, but are not limited to, tissue, whole blood, serum, or plasma from an individual. Samples also include, but are not limited to tissue, a cell, or a fluid obtained from a tissue or cell.

As used herein, method for "aiding assessment" refers to methods that assist in making a clinical determination (e.g., risk of anaphylaxis), and may or may not be conclusive with respect to the definitive assessment.

As used herein, a "reference value" can be an absolute value; a relative value; a value that has an upper and/or lower limit; a range of values; an average value; a median value; a mean value; or a value as compared to a particular control or baseline value.

The term "detecting" or "detection" is used in the broadest sense to include both qualitative and quantitative measurements of a specific molecule, herein measurements of a specific analyte molecule such as hypusine in a hypusine-containing polypeptide or deoxyhypusine in a deoxyhypusine-containing polypeptide. In one aspect, a detection method described herein is used to identify the mere presence of an analyte molecule of interest in a sample. In another aspect, a detection method can be used to quantify an amount of analyte molecule in a sample. In still another aspect, the method can be used to determine the relative binding affinity of an analyte molecule of interest for a target molecule.

The term "detecting agent", "detection agent", "detecting reagent", and "detection reagent" are used interchangeably to refer to an agent that detects an anti-hypusine antibody, either directly via a label, such as a magnetic, chromophore, dye, fluorescent, enzymatic, radioactive, or chemiluminescent label, that can be linked to the anti-hypusine antibody, or indirectly via a labeled a secondary agent, such as an antibody or receptor that specifically binds the anti-hypusine antibody. Examples of secondary agents include, but are not limited to, an antibody, antibody fragment, soluble receptor, receptor fragment, and the like.

The term "assay surface" or "surface" means a substrate on which a capture agent may be immobilized for use in an immunoassay. Suitable assay surfaces include polymeric assay plate, chips, fluidity cards, magnetic beads, resins, cellulose polymer sponge, and the like.

The term "capture agent" or "capture reagent" refers to an agent (e.g., an anti-hypusine antibody) capable of binding and capturing a target molecule or analyte molecule (e.g., a polypeptide containing a hypusine and/or deoxyhypusine) in a sample. A capture agent or reagent can be immobilized, for example, on a solid substrate, such as a microparticle or bead, microtiter plate, column resin, chip, fluidity card, magnetic bead, cellulose polymer sponge, and the like.

The term "label" when used herein refers to a compound or composition which is conjugated or fused directly or indirectly to a reagent such as a nucleic acid probe, a polypeptide or an antibody and facilitates detection or capture of the reagent to which it is conjugated or fused. The label may itself be detectable (e.g., radioisotope, fluorescent, photoluminescent, chemiluminescent, or electrochemiluminescent labels), detectable after binding to another molecule, or in the case of an enzymatic label, may catalyze chemical alteration of a substrate compound or composition which is detectable.

The term "target molecule" refers to a specific binding target of the antibody described herein. In one embodiment, the target molecule is a hypusine in a hypusine-containing polypeptide or a hypusine-containing polypeptide. In one embodiment, the target molecule is a deoxyhypusine in a deoxyhypusine-containing polypeptide or a deoxyhypusine-containing polypeptide.

"Analyte" and "analyte molecule," as used herein, refer to a molecule that is analyzed by the methods of the invention, and includes, but is not limited to, a polypeptide containing hypusine and/or deoxyhypusine.

The terms, "protein," "peptide," and "polypeptide" are used interchangeably to denote an amino acid polymer or a set of two or more interacting or bound amino acid polymers.

"Polypeptide" refers to a peptide or protein containing two or more amino acids linked by peptide bonds, and includes peptides, oligomers, proteins, and the like. Polypeptides can contain natural, modified, or synthetic amino acids. Polypeptides can also be modified naturally, such as by post-translational processing, or chemically, such as amidation acylation, cross-linking, and the like.

II. Anti-Hypusine Antibodies

In one aspect, the invention provides isolated antibodies that bind to a hypusine in a polypeptide. In some embodiments, the anti-hypusine antibody described herein has one or more of the following characteristics: (1) binds to hypusine in a polypeptide; (2) does not bind to deoxyhypusine in a polypeptide; (3) binds to deoxyhypusine in a polypeptide; (4) binds to hypusine in hypusine-containing polypeptides with different amino acids flanking hypusine; (5) binds to deoxyhypusine in deoxyhypusine-containing polypeptides with different amino acids flanking deoxyhypusine; (6) binds to hypusine in a hypusine-containing polypeptide with a binding affinity of 900 nM or less; and (7) binds to hypusine in a hypusine-containing polypeptide with a binding affinity of 300 nM or less and to deoxyhypusine in a deoxyhypusine-containing polypeptide with a binding affinity of 200 nM or less.

In one aspect, the invention provides isolated antibodies that bind to hypusine in a polypeptide, wherein the antibody binds to hypusine-containing polypeptides with different amino acid sequences flanking hypusine. In some embodiments, the antibody does not bind to deoxyhypusine in a polypeptide. In some embodiments, the antibody binds to deoxyhypusine in a polypeptide. In some embodiments, the antibody binds to a peptide shown in Table 1 (e.g., one or more selected from the group of SEQ ID NOs:56-69).

In one aspect, an anti-hypusine antibody described herein is a monoclonal antibody. In one aspect, an anti-hypusine antibody described herein is an antibody fragment (including antigen-binding fragment), e.g., a Fab, Fab'-SH, Fv, scFv, or (Fab')$_2$ fragment. In one aspect, any of the anti-hypusine antibodies described herein are purified.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:9, (ii) HVR-H2 comprising the amino acid sequence of SEQ ID NO:13 or 14, and (iii) HVR-H3 comprising the amino acid sequence of SEQ ID NO:17; and/or wherein the light chain variable region comprises (i) HVR-L1 comprising the amino acid sequence of SEQ ID NO:1 or 2, (ii) HVR-L2 comprising the amino acid sequence of SEQ ID NO:4 or 5, and (iii) HVR-L3 comprising the amino acid sequence of SEQ ID NO:7.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:11 or 12, (ii) HVR-H2 comprising the amino acid sequence of SEQ ID NO:16, and (iii) HVR-H3 comprising the amino acid sequence of SEQ ID NO:19; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:8.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:10, (ii) HVR-H2 comprising the amino acid sequence of SEQ ID NO:15, and (iii) HVR-H3 comprising the amino acid sequence of SEQ ID NO:18; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:72.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:9, (ii) HVR-H2 comprising the amino acid sequence of SEQ ID NO:13, and (iii) HVR-H3 comprising the amino acid sequence of SEQ ID NO:17; and/or wherein the light chain variable region comprises (i) HVR-L1 comprising the amino acid sequence of SEQ ID NO:1, (ii) HVR-L2 comprising the amino acid sequence of SEQ ID NO:4, and (iii) HVR-L3 comprising the amino acid sequence of SEQ ID NO:7.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:9, (ii) HVR-H2 comprising the amino acid sequence of SEQ ID NO:14, and (iii) HVR-H3 comprising the amino acid sequence of SEQ ID NO:17; and/or wherein the light chain variable region comprises (i) HVR-L1 comprising the amino acid sequence of SEQ ID NO:2, (ii) HVR-L2 comprising the amino acid sequence of SEQ ID NO:5, and (iii) HVR-L3 comprising the amino acid sequence of SEQ ID NO:7.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:11, (ii) HVR-H2 comprising the amino acid sequence of SEQ ID NO:16, and (iii) HVR-H3 comprising the amino acid sequence of SEQ ID NO:19; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:8.

In one aspect, provided herein is an anti-hypusine antibody comprising a heavy chain variable region and a light chain variable region, wherein the heavy chain variable region comprises (i) HVR-H1 comprising the amino acid sequence of SEQ ID NO:12, (ii) HVR-H2 comprising the amino acid sequence of SEQ ID NO:16, and (iii) HVR-H3 comprising the amino acid sequence of SEQ ID NO:19; and/or wherein the light chain variable region comprises (i) HVR-L1 comprising the amino acid sequence of SEQ ID NO:3, (ii) HVR-L2 comprising the amino acid sequence of SEQ ID NO:6, and (iii) HVR-L3 comprising the amino acid sequence of SEQ ID NO:8.

An anti-hypusine antibody described herein may comprise any suitable framework variable domain sequence, provided that the antibody retains the ability to bind hypusine in a polypeptide. In some embodiments, the antibody retains the ability to bind hypusine and deoxyhypusine in a polypeptide. As used herein, heavy chain framework regions are designated "HC-FR1-FR4," and light chain framework regions are designated "LC-FR1-FR4." In some embodiments, the anti-hypusine antibody comprises a heavy chain variable domain framework sequence of SEQ ID NO:46, 50, 51, and 53 (HC-FR1, HC-FR2, HC-FR3, and HC-FR4, respectively). In some embodiments, the anti-hypusine antibody comprises a heavy chain variable domain framework sequence of SEQ ID NO:47, 50, 52, and 53 (HC-FR1, HC-FR2, HC-FR3, and HC-FR4, respectively). In some embodiments, the anti-hypusine antibody comprises a heavy chain variable domain framework sequence of SEQ ID NO:48, 50, 52, and 53 (HC-FR1, HC-FR2, HC-FR3, and HC-FR4, respectively). In some embodiments, the anti-hypusine antibody comprises a heavy chain variable domain framework sequence of SEQ ID NO:49, 50, 52, and 53 (HC-FR1, HC-FR2, HC-FR3, and HC-FR4, respectively). In some embodiments, the anti-hypusine antibody comprises a light chain variable domain framework sequence of SEQ ID NO:38, 40, 42, and 45 (LC-FR1, LC-FR2, LC-FR3, and LC-FR4, respectively). In some embodiments, the anti-hypusine antibody comprises a light chain variable domain framework sequence of SEQ ID NO:39, 41, 43, and 45 (LC-FR1, LC-FR2, LC-FR3, and LC-FR4, respectively). In some embodiments, the anti-hypusine antibody comprises a light chain variable domain framework sequence of SEQ ID NO:39, 41, 44, and 45 (LC-FR1, LC-FR2, LC-FR3, and LC-FR4, respectively).

In one embodiment, an anti-hypusine antibody comprises a heavy chain variable domain comprising a framework sequence and hypervariable regions, wherein the framework sequence comprises the HC-FR1-HC-FR4 sequences SEQ ID NOs:46-49 (HC-FR1), SEQ ID NO:50 (HC-FR2), SEQ ID NOs:51 or 52 (HC-FR3), and SEQ ID NO:53 (HC-FR4), respectively; the HVR-H1 comprises the amino acid sequence of SEQ ID NO:9; the HVR-H2 comprises the amino acid sequence of SEQ ID NO:13 or 14; and the HVR-H3 comprises an amino acid sequence of SEQ ID NO:17. In one embodiment, an anti-hypusine antibody comprises a heavy chain variable domain comprising a framework sequence and hypervariable regions, wherein the framework sequence comprises the HC-FR1-HC-FR4 sequences SEQ ID NOs:46-49 (HC-FR1), SEQ ID NO:50 (HC-FR2), SEQ ID NOs:51 or 52 (HC-FR3), and SEQ ID NO:53 (HC-FR4), respectively; the HVR-H1 comprises the amino acid sequence of SEQ ID NO:10; the HVR-H2 comprises the amino acid sequence of SEQ ID NO:15; and the HVR-H3 comprises an amino acid sequence of SEQ ID NO:18. In one embodiment, an anti-hypusine antibody comprises a heavy chain variable domain comprising a framework sequence and hypervariable regions, wherein the framework sequence comprises the HC-FR1-HC-FR4 sequences SEQ ID NOs:46-49 (HC-FR1), SEQ ID NO:50 (HC-FR2), SEQ ID NOs:51 or 52 (HC-FR3), and SEQ ID NO:53 (HC-FR4), respectively; the HVR-H1 comprises the amino acid sequence of SEQ ID NO:11 or 12; the HVR-H2 comprises the amino acid sequence of SEQ ID NO:16; and the HVR-H3 comprises an amino acid sequence of SEQ ID NO:19. In one embodiment, an anti-hypusine antibody comprises a light chain variable domain comprising a framework sequence and hypervariable regions, wherein the framework sequence comprises the LC-FR1-LC-FR4 sequences SEQ ID NOs:38 or 39 (LC-FR1), SEQ ID NOs:40 or 41 (LC-FR2), SEQ ID NOs:42-44 (LC-FR3), and SEQ ID NO:45 (LC-FR4), respectively; the HVR-L1 comprises the amino acid sequence of SEQ ID NO:1 or 2; the HVR-L2 comprises the amino acid sequence of SEQ ID NO:4 or 5; and the HVR-L3 comprises an amino acid sequence of SEQ ID NO:7. In one embodiment, an anti-hypusine antibody comprises a light chain variable domain comprising a framework sequence and hypervariable regions, wherein the framework sequence comprises the LC-FR1-LC-FR4 sequences SEQ ID NOs:38 or 39 (LC-FR1), SEQ ID NOs:40 or 41 (LC-FR2), SEQ ID NOs:42-44 (LC-FR3), and SEQ ID NO:45 (LC-FR4), respectively; the HVR-L1 comprises the amino acid sequence of SEQ ID NO:3; the HVR-L2 comprises the amino acid sequence of SEQ ID NO:6; and the HVR-L3 comprises an amino acid sequence of SEQ ID NO:8. In one embodiment, an anti-hypusine antibody comprises a light chain variable domain comprising a framework sequence and hypervariable regions, wherein the framework sequence comprises the LC-FR1-LC-FR4 sequences SEQ ID NOs:38 or 39 (LC-FR1), SEQ ID NOs:40 or 41 (LC-FR2), SEQ ID NOs:42-44 (LC-FR3), and SEQ ID NO:45 (LC-FR4), respectively; the HVR-L1 comprises the amino acid sequence of SEQ ID NO:3; the HVR-L2 comprises the amino acid sequence of SEQ ID NO:6; and the HVR-L3 comprises an amino acid sequence of SEQ ID NO:72. In one embodiment of these antibodies, the heavy chain variable domain comprises an amino acid sequence of SEQ ID NO:24 or 25 and the light chain variable domain comprises an amino acid sequence of SEQ ID NOs:20 or 21. In one embodiment of these antibodies, the heavy chain variable domain comprises an amino acid sequence of SEQ ID NO:27 or 28 and the light chain variable domain comprises an amino acid sequence of SEQ ID NO:23. In one embodiment of these antibodies, the heavy chain variable domain comprises an amino acid sequence of SEQ ID NO:26 and the light chain variable domain comprises an amino acid sequence of SEQ ID NO:22. In one embodiment of these antibodies, the heavy chain variable domain comprises an amino acid sequence of SEQ ID NO:24 and the light chain variable domain comprises an amino acid sequence of SEQ ID NO:20. In one embodiment of these antibodies, the heavy chain variable domain comprises an amino acid sequence of SEQ ID NO:25 and the light chain variable domain comprises an amino acid sequence of SEQ ID NO:21. In one embodiment of these antibodies, the heavy chain variable domain comprises an amino acid sequence of SEQ ID NO:27 and the light chain variable domain comprises an amino acid sequence of SEQ ID NO:23. In one embodiment of these antibodies, the heavy chain variable domain comprises an amino acid sequence of SEQ ID NO:28 and the light chain variable domain comprises an amino acid sequence of SEQ ID NO:23.

In some embodiments, the heavy chain HVR sequences comprise the following:

```
a) HVR-H1 (DYAMI (SEQ ID NO: 9));

b) HVR-H2 (IIYGGSNKLAYAKWA (SEQ ID NO: 13)
or

IIYGVINDLAYAKWA (SEQ ID NO: 14));
and c) HVR-H3 (GYGSMDGYDRLNL (SEQ ID NO: 17)).
```

In some embodiments, the heavy chain HVR sequences comprise the following:

```
a) HVR-H1 (TYTIN (SEQ ID NO: 10));

b) HVR-H2 (DIWSDGNTYYANWA (SEQ ID NO: 15));
and c) HVR-H3 (DSWDTSIYYGLDL (SEQ ID NO: 18)).
```

In some embodiments, the heavy chain HVR sequences comprise the following:

```
a) HVR-H1 (TYTMN (SEQ ID NO: 11);
or

HCTMN (SEQ ID NO: 12);

b) HVR-H2 (DIYTDGNTYYANWA (SEQ ID NO: 16));
and c) HVR-H3 (DSWDASSYYGLDL (SEQ ID NO: 19)).
```

In some embodiments, the heavy chain FR sequences comprise the following:

```
a) HC-FR1 (QEQLKESGGRLVAPGTPLTLTCTVSGFDIS (SEQ ID NO: 46);

QSVEESGGRLVTPGTPLTLTCTVSAFSLS (SEQ ID NO: 47);

QSVEESGGRLVTPGTPLTLTCTVSGFSLS (SEQ ID NO :48);
or

QSVEESGGRLVTPGTPLTLTCTVSACSLY (SEQ ID NO: 49));

b) HC-FR2 (WVRQAPGKGLEWIG (SEQ ID NO: 50);

c) HC-FR3 (KGRFTISRTSTTVDLKITSPTTEDTATYFCAR (SEQ ID NO: 51);
or

KGRFTISKTSTTVDLKITSPTTEDTATYFCAR (SEQ ID NO: 52));
and d) HC-FR4 (WGQGTLVTVSS (SEQ ID NO: 53)).
```

In some embodiments, the light chain HVR sequences comprise the following:

```
a) HVR-L1 (QSSETVYRGDWLS (SEQ ID NO: 1);
or

RSRQRVYLGDWLS (SEQ ID NO: 2));

b) HVR-L2 (DASYLAS (SEQ ID NO: 4);
or

DASFRGD (SEQ ID NO: 5));
and c) HVR-L3 (LGGYYDDADDT (SEQ ID NO: 7)).
```

In some embodiments, the light chain HVR sequences comprise the following:

```
a) HVR-L1 (QASEDIKRYLA (SEQ ID NO: 3));

b) HVR-L2 (AASKLAS (SEQ ID NO: 6));
and c) HVR-L3 (QQGYTSSNVNNA (SEQ ID NO: 8);
or

QQGYTSTNVNNA (SEQ ID NO: 72)).
```

In some embodiments, the light chain FR sequences comprise the following:

```
a) LC-FR1 (AAVLTQTPSPVSAAVGGTVTISC (SEQ ID NO: 38);
or

AIKMTQTPSSVSAAVGGTVTINC (SEQ ID NO: 39));

b) LC-FR2 (WFQKKPGQPPKLLIY (SEQ ID NO: 40);
or

WYQQKPGQPPKLLIY (SEQ ID NO: 41));

c) LC-FR3 (GVSSRFSGSGSGTHFTLTISGVQCDDAATYYC (SEQ ID NO: 42);

GVSSRFTGSGSGTEYTLTISGVQCDDAATYYC (SEQ ID NO: 43);
or

GVSSRFKGSGSGTEYTLTISGVQCDDAATYYC (SEQ ID NO: 44));
and d) LC-FR4 (FGGGTEVVVK (SEQ ID NO: 45)).
```

In some embodiments, provided herein is an anti-hypusine antibody that binds to hypusine in a polypeptide, wherein the antibody comprises a heavy chain variable region and a light chain variable region, wherein the antibody comprises:

(a) heavy chain variable domain comprising:

(1) an HC-FR1 comprising the amino acid sequence selected from SEQ ID NOs:46-49;

(2) an HVR-H1 comprising the amino acid sequence of SEQ ID NO:9;

(3) an HC-FR2 comprising the amino acid sequence of SEQ ID NO:50;
(4) an HVR-H2 comprising the amino acid sequence of SEQ ID NO:13;
(5) an HC-FR3 comprising the amino acid sequence of SEQ ID NO:51 or 52;
(6) an HVR-H3 comprising the amino acid sequence of SEQ ID NO:17; and
(7) an HC-FR4 comprising the amino add sequence of SEQ ID NO:53,
and/or
(b) a light chain variable domain comprising:
(1) an LC-FR1 comprising the amino acid sequence of SEQ ID NO:38 or 39;
(2) an HVR-L1 comprising the amino acid sequence of SEQ ID NO:1;
(3) an LC-FR2 comprising the amino acid sequence of SEQ ID NO:40 or 41;
(4) an HVR-L2 comprising the amino acid sequence of SEQ ID NO:4;
(5) an LC-FR3 comprising the amino acid sequence selected from SEQ ID NOs:42-44;
(6) an HVR-L3 comprising the amino acid sequence of SEQ ID NO:7; and
(7) an LC-FR4 comprising the amino acid sequence of SEQ ID NO:45.

In some embodiments, provided herein is an anti-hypusine antibody that binds to hypusine in a polypeptide, wherein the antibody comprises a heavy chain variable region and a light chain variable region, wherein the antibody comprises:
(a) heavy chain variable domain comprising:
(1) an HC-FR1 comprising the amino add sequence selected from SEQ ID NOs:46-49;
(2) an HVR-H1 comprising the amino acid sequence of SEQ ID NO:9;
(3) an HC-FR2 comprising the amino acid sequence of SEQ ID NO:50;
(4) an HVR-H2 comprising the amino acid sequence of SEQ ID NO:14;
(5) an HC-FR3 comprising the amino acid sequence of SEQ ID NO:51 or 52;
(6) an HVR-H3 comprising the amino acid sequence of SEQ tD NO:17; and
(7) an HC-FR4 comprising the amino acid sequence of SEQ ID NO:53,
and/or
(b) a light chain variable domain comprising:
(1) an LC-FR1 comprising the amino acid sequence of SEQ ID NO:38 or 39;
(2) an HVR-L1 comprising the amino acid sequence of SEQ ID NO:2;
(3) an LC-FR2 comprising the amino acid sequence of SEQ ID NO:40 or 41;
(4) an HVR-L2 comprising the amino acid sequence of SEQ ID NO:5;
(5) an LC-FR3 comprising the amino acid sequence selected from SEQ ID NOs:42-44;
(6) an HVR-L3 comprising the amino acid sequence of SEQ ID NO:7; and
(7) an LC-FR4 comprising the amino acid sequence of SEQ ID NO:45.

In some embodiments, provided herein is an anti-hypusine antibody that binds to hypusine in a polypeptide, wherein the antibody comprises a heavy chain variable region and a light chain variable region, wherein the antibody comprises:
(a) heavy chain variable domain comprising:
(1) an HC-FR1 comprising the amino acid sequence selected from SEQ ID NOs:46-49;
(2) an HVR-H1 comprising the amino acid sequence of SEQ ID NO:10;
(3) an HC-FR2 comprising the amino acid sequence of SEQ ID NO:50;
(4) an HVR-H2 comprising the amino acid sequence of SEQ ID NO:15;
(5) an HC-FR3 comprising the amino acid sequence of SEQ ID NO:51 or 52;
(6) an HVR-H3 comprising the amino acid sequence of SEQ ID NO:18; and
(7) an HC-FR4 comprising the amino acid sequence of SEQ ID NO:53,
and/or
(b) a light chain variable domain comprising:
(1) an LC-FR1 comprising the amino acid sequence of SEQ ID NO:38 or 39;
(2) an HVR-L1 comprising the amino acid sequence of SEQ ID NO:3;
(3) an LC-FR2 comprising the amino acid sequence of SEQ ID NO:40 or 41;
(4) an HVR-L2 compri sing the amino acid sequence of SEQ ID NO:6;
(5) an LC-FR3 comprising the amino acid sequence selected from SEQ ID NOs:42-44;
(6) an HVR-L3 comprising the amino acid sequence of SEQ ID NO:72; and
(7) an LC-FR4 comprising the amino acid sequence of SEQ ID NO:45.

In some embodiments, provided herein is an anti-hypusine antibody that binds to hypusine in a polypeptide, wherein the antibody comprises a heavy chain variable region and a light chain variable region, wherein the antibody comprises:
(a) heavy chain variable domain comprising:
(1) an HC-FR1 comprising the amino acid sequence selected from SEQ ID NOs:46-49;
(2) an HVR-H1 comprising the amino acid sequence of SEQ ID NO:11;
(3) an HC-FR2 comprising the amino acid sequence of SEQ ID NO:50;
(4) an HVR-H2 comprising the amino acid sequence of SEQ ID NO:16;
(5) an HC-FR3 comprising the amino acid sequence of SEQ :ID NO:51 or 52;
(6) an HVR-H3 comprising the amino acid sequence of SEQ ID NO:19; and
(7) an HC-FR4 comprising the amino acid sequence of SEQ ID NO:53,
and/or
(b) a light chain variable domain comprising
(1) an LC-FR1 comprising the amino acid sequence of SEQ ID NO:38 or 39;
(2) an HVR-L1 comprising the amino acid sequence of SEQ ID NO:3;
(3) an LC-FR2 comprising the amino acid sequence of SEQ ID NO:40 or 41;
(4) an HVR-H2 comprising the amino acid sequence of SEQ ID NO:6;
(5) an LC-FR3 comprising the amino acid sequence selected from SEQ NOs:42-44;
(6) an HVR-L3 comprising the amino acid sequence of SEQ ID NO:8; and (7) an LC-FR4 comprising the amino acid sequence of SEQ ID NO:45.

In some embodiments, provided herein is an anti-hypusine antibody that binds to hypusine in a polypeptide, wherein the antibody comprises a heavy chain variable region and a light chain variable region, wherein the antibody comprises:

(a) heavy chain variable domain comprising:

(1) an HC-FR1 comprising the amino acid sequence selected from SEQ D NOs:46-49;

(2) an HVR-H1 comprising the amino acid sequence of SEQ ID NO:12;

(3) an HC-FR2 comprising the amino acid sequence of SEQ ID NO:50;

(4) an HVR-H2 comprising the amino acid sequence of SEQ ID NO:16;

(5) an HC-FR3 comprising the amino acid sequence of SEQ ID NO:51 or 52;

(6) an HVR-H3 comprising the amino acid sequence of SEQ ID NO:19; and (7) an HC-FR4 comprising the amino acid sequence of SEQ NO:53, and/or (b) a light chain variable domain comprising:

(1) an LC-FR1 comprising the amino acid sequence of SEQ ID NO:38 or 39;

(2) an HVR-L1 comprising the amino acid sequence of SEQ ID NO:3;

(3) an LC-FR2 comprising the amino acid sequence of SEQ NO:40 or 41;

(4) an HVR-L2 comprising the amino acid sequence of SEQ ID NO:6;

(5) an LC-FR3 comprising the amino acid sequence selected from SEQ ID NOs:42-44;

(6) an HVR-L3 comprising the amino acid sequence of SEQ ID NO:8; and (7) an LC-FR4 comprising the amino acid sequence of SEQ ID NO:45.

In one aspect, provided herein is an anti-hypusine antibody comprising a heavy chain variable domain comprising the amino acid sequence of SEQ ID NO:24 or 25 and/or comprising a light chain variable domain comprising the amino acid sequence of SEQ ID NO:20 or 21, including post-translational modifications of those sequences. In one aspect, provided herein is an anti-hypusine antibody comprising a heavy chain variable domain comprising the amino acid sequence of SEQ ID NO:27 or 28 and/or comprising a light chain variable domain comprising the amino acid sequence of SEQ ID NO:23, including post-translational modifications of those sequences. In one aspect, provided herein is an anti-hypusine antibody comprising a heavy chain variable domain comprising the amino acid sequence of SEQ ID NO:26 and/or comprising a light chain variable domain comprising the amino acid sequence of SEQ ID NO:22, including post-translational modifications of those sequences.

In one aspect, provided herein is an anti-hypusine antibody comprising a heavy chain variable domain comprising the amino acid sequence of SEQ ID NO:24 and/or comprising a light chain variable domain comprising the amino acid sequence of SEQ ID NO:20, including post-translational modifications of those sequences. In one aspect, provided herein is an anti-hypusine antibody comprising a heavy chain variable domain comprising the amino acid sequence of SEQ ID NO:25 and/or comprising a light chain variable domain comprising the amino acid sequence of SEQ ID NO:21, including post-translational modifications of those sequences. In one aspect, provided herein is an anti-hypusine antibody comprising a heavy chain variable domain comprising the amino acid sequence of SEQ ID NO:27 and/or comprising a light chain variable domain comprising the amino acid sequence of SEQ ID NO:23, including post-translational modifications of those sequences. In one aspect, provided herein is an anti-hypusine antibody comprising a heavy chain variable domain comprising the amino acid sequence of SEQ ID NO:28 and/or comprising a light chain variable domain comprising the amino acid sequence of SEQ ID NO:23, including post-translational modifications of those sequences. In one aspect, provided herein is an anti-hypusine antibody comprising a heavy chain variable domain comprising the amino acid sequence of SEQ ID NO:26 and/or comprising a light chain variable domain comprising the amino acid sequence of SEQ ID NO:22, including post-translational modifications of those sequences.

In some embodiments, provided herein is an anti-hypusine antibody comprising a heavy chain variable domain comprising an amino acid sequence having at least 90%, 91%, 92%, 93%, 94%, 95%, 96%, 97%, 98%, or 99% sequence identity to an amino acid sequence of SEQ ID NO:24 or 25. In some embodiments, provided herein is an anti-hypusine antibody comprising a heavy chain variable domain comprising an amino acid sequence having at least 90%, 91%, 92%, 93%, 94%, 95%, 96%, 97%, 98%, or 99% sequence identity to an amino acid sequence of SEQ ID NO:26. In some embodiments, provided herein is an anti-hypusine antibody comprising a heavy chain variable domain comprising an amino acid sequence having at least 90%, 91%, 92%, 93%, 94%, 95%, 96%, 97%, 98%, or 99% sequence identity to an amino acid sequence of SEQ ID NO:27 or 28. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to hypusine in a polypeptide. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to hypusine and deoxyhypusine in a polypeptide. In some embodiments, the substitutions, insertions, or deletions (e.g., 1, 2, 3, 4, or 5 amino acids) occur in regions outside the HVRs (i.e., in the FRs).

In some embodiments, provided herein is an anti-hypusine antibody comprising a light chain variable domain comprising an amino acid sequence having at least 90%, 91%, 92%, 93%, 94%, 95%, 96%, 97%, 98%, or 99% sequence identity to an amino acid sequence of SEQ ID NO:20 or 21. In some embodiments, provided herein is an anti-hypusine antibody comprising a light chain variable domain comprising an amino acid sequence having at least 90%, 91%, 92%, 93%, 94%, 95%, 96%, 97%, 98%, or 99% sequence identity to an amino acid sequence of SEQ ID NO:22. In some embodiments, provided herein is an anti-hypusine antibody comprising a light chain variable domain comprising an amino acid sequence having at least 90%, 91%, 92%, 93%, 94%, 95%, 96%, 97%, 98%, or 99% sequence identity to an amino acid sequence of SEQ ID NO:23. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to hypusine in a polypeptide. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to hypusine and deoxyhypusine in a polypeptide. In some embodiments, the substitutions, insertions, or deletions (e.g., 1, 2, 3, 4, or 5 amino acids) occur in regions outside the HVRs (i.e., in the FRs).

In some embodiments, provided herein is an anti-hypusine antibody comprising a heavy chain variable domain as depicted in FIG. 1B or FIG. 1D. For example, provided herein is an anti-hypusine antibody comprising a heavy chain variable domain of antibody Hpu24 as shown in FIG. 1B. In some embodiments, provided herein is an anti-hypusine antibody comprising a heavy chain variable domain of antibody Hpu24.B as shown in FIG. 1B. In some embodiments, provided herein is an anti-hypusine antibody comprising a heavy chain variable domain of antibody Hpu98 as shown in FIG. 1D. In some embodiments, provided herein is an anti-hypusine antibody comprising a heavy chain variable domain of antibody Hpu98.61 as shown in FIG. 1D. In some embodiments, provided herein is an anti-hypusine antibody comprising a heavy chain variable domain of antibody Hpu91 as shown in FIG. 1D.

In some embodiments, provided herein is an anti-hypusine antibody comprising a light chain variable domain as depicted in FIG. 1A or FIG. 1C. For example, provided herein is an anti-hypusine antibody comprising a light chain variable domain of antibody Hpu24 as shown in FIG. 1A. In some embodiments, provided herein is an anti-hypusine antibody comprising a light chain variable domain of antibody Hpu24.B as shown in FIG. 1A. In some embodiments, provided herein is an anti-hypusine antibody comprising a light chain variable domain of antibody Hpu98 as shown in FIG. 1C. In some embodiments, provided herein is an anti-hypusine antibody comprising a light chain variable domain of antibody Hpu98.61 as shown in FIG. 1C. In some embodiments, provided herein is an anti-hypusine antibody comprising a light chain variable domain of antibody Hpu91 as shown in FIG. 1C.

In one aspect, the invention provides an anti-hypusine antibody comprising a heavy chain variable domain selected from those shown in FIG. 1B or FIG. 1D and a light chain variable domain selected from those shown in FIG. 1A or FIG. 1C. For example, provided herein is an anti-hypusine antibody comprising a heavy chain variable domain of an antibody Hpu24 as shown in FIG. 1B, an antibody Hpu24.B as shown in FIG. 1B, an antibody Hpu91 as shown in FIG. 1D, an antibody Hpu98 as shown in FIG. 1D, or an antibody Hpu98.61 as shown in FIG. 1D and a light chain variable domain of an antibody Hpu24 as shown in FIG. 1A, an antibody Hpu24.B as shown in FIG. 1A, an antibody Hpu91 as shown in FIG. 1C, an antibody Hpu98 as shown in FIG. 1C, or an antibody Hpu98.61 as shown in FIG. 1C.

In one aspect, the invention provides an anti-hypusine antibody comprising (a) one, two, or three VH HVRs selected from those shown in FIG. 1B or FIG. 1D and/or (b) one, two, or three VL HVRs selected from those shown in FIG. 1A or FIG. 1C. For example, an anti-hypusine antibody provided herein comprises (a) one, two, or three Chothia VH HVRs from Hpu24 as shown in FIG. 1B and/or (b) one, two, or three Chothia VL HVRs from Hpu24 as shown in FIG. 1A. In some embodiments, an anti-hypusine antibody provided herein comprises (a) one, two, or three Chothia VH HVRs from Hpu24.B as shown in FIG. 1B and/or (b) one, two, or three Chothia VL HVRs from Hpu24.B as shown in FIG. 1A. In some embodiments, an anti-hypusine antibody provided herein comprises (a) one, two, or three Chothia VH HVRs from Hpu91 as shown in FIG. 1D and/or (b) one, two, or three Chothia VL HVRs from Hpu91 as shown in FIG. 1C. In some embodiments, an anti-hypusine antibody provided herein comprises (a) one, two, or three Chothia VH HVRs from Hpu98 as shown in FIG. 1D and/or (b) one, two, or three Chothia VL HVRs from Hpu98 as shown in FIG. 1C. In some embodiments, an anti-hypusine antibody provided herein comprises (a) one, two, or three Chothia VH HVRs from Hpu98.61 as shown in FIG. 1D and/or (b) one, two, or three Chothia VL HVRs from Hpu98.61 as shown in FIG. 1C. In some embodiments, an anti-hypusine antibody provided herein comprises (a) one, two, or three Kabat VH HVRs from Hpu24 as shown in FIG. 1B and/or (b) one, two, or three Kabat VL HVRs from Hpu24 as shown in FIG. 1A. In some embodiments, an anti-hypusine antibody provided herein comprises (a) one, two, or three Kabat VH HVRs from Hpu24.B as shown in FIG. 1B and/or (b) one, two, or three Kabat VL HVRs from Hpu24.B as shown in FIG. 1A. In some embodiments, an anti-hypusine antibody provided herein comprises (a) one, two, or three Kabat VH HVRs from Hpu91 as shown in FIG. 1D and/or (b) one, two, or three Kabat VL HVRs from Hpu91 as shown in FIG. 1C. In some embodiments, an anti-hypusine antibody provided herein comprises (a) one, two, or three Kabat VH HVRs from Hpu98 as shown in FIG. 1D and/or (b) one, two, or three Kabat VL HVRs from Hpu98 as shown in FIG. 1C. In some embodiments, an anti-hypusine antibody provided herein comprises (a) one, two, or three Kabat VH HVRs from Hpu98.61 as shown in FIG. 1D and/or (b) one, two, or three Kabat VL HVRs from Hpu98.61 as shown in FIG. 1C. In some embodiments, an anti-hypusine antibody provided herein comprises (a) one, two, or three Contact VH HVRs from Hpu24 as shown in FIG. 1B and/or (b) one, two, or three Contact VL HVRs from Hpu24 as shown in FIG. 1A. In some embodiments, an anti-hypusine antibody provided herein comprises (a) one, two, or three Contact VH HVRs from Hpu24.B as shown in FIG. 1B and/or (b) one, two, or three Contact VL HVRs from Hpu24.B as shown in FIG. 1A. In some embodiments, an anti-hypusine antibody provided herein comprises (a) one, two, or three Contact VH HVRs from Hpu91 as shown in FIG. 1D and/or (b) one, two, or three Contact VL HVRs from Hpu91 as shown in FIG. 1C. In some embodiments, an anti-hypusine antibody provided herein comprises (a) one, two, or three Contact VH HVRs from Hpu98 as shown in FIG. 1D and/or (b) one, two, or three Contact VL HVRs from Hpu98 as shown in FIG. 1C. In some embodiments, an anti-hypusine antibody provided herein comprises (a) one, two, or three Contact VH HVRs from Hpu98.61 as shown in FIG. 1D and/or (b) one, two, or three Contact VL HVRs from Hpu98.61 as shown in FIG. 1C.

In some embodiments, provided herein is an anti-hypusine antibody comprising a heavy chain comprising the amino acid sequence of SEQ ID NO:33 or 34; and/or a light chain comprising the amino acid sequence of SEQ ID NO:29 or 30. In some embodiments, provided herein is an anti-hypusine antibody comprising a heavy chain comprising the amino acid sequence of SEQ ID NO:35; and/or a light chain comprising the amino acid sequence of SEQ ID NO:31. In some embodiments, provided herein is an anti-hypusine antibody comprising a heavy chain comprising the amino acid sequence of SEQ ID NO:36 or 37; and/or a light chain comprising the amino acid sequence of SEQ ID NO:32. In some embodiments, the anti-hypusine antibody binds to hypusine in a polypeptide.

In some embodiments, provided herein is an anti-hypusine antibody comprising a heavy chain comprising the amino acid sequence of SEQ ID NO:33 and/or a light chain comprising the amino acid sequence of SEQ ID NO:29. In some embodiments, provided herein is an anti-hypusine antibody comprising a heavy chain comprising the amino acid sequence of SEQ ID NO:34 and/or a light chain comprising the amino acid sequence of SEQ ID NO:30. In some embodiments, provided herein is an anti-hypusine antibody comprising a heavy chain comprising the amino acid sequence of SEQ ID NO:35 and/or a light chain comprising the amino acid sequence of SEQ ID NO:31. In some embodiments, provided herein is an anti-hypusine antibody comprising a heavy chain comprising the amino acid sequence of SEQ ID NO:36 and/or a light chain comprising the amino acid sequence of SEQ ID NO:32. In some embodiments, provided herein is an anti-hypusine antibody comprising a heavy chain comprising the amino acid sequence of SEQ ID NO:37 and/or a light chain comprising the amino acid sequence of SEQ ID NO:32. In some embodiments, the anti-hypusine antibody binds to hypusine in a polypeptide.

In some embodiments herein, the anti-hypusine antibody binds to hypusine and deoxyhypusine in a polypeptide. In some embodiments herein, the anti-hypusine antibody does not bind to deoxyhypusine in a polypeptide.

Anti-hypusine antibodies provided herein may be identified, screened for, or characterized for their physical/chemical properties and/or biological activities by various assays known in the art and described in the Examples herein. Antibodies having such properties (e.g., physical property) or activity (e.g., biological activity) in vivo and/or in vitro are provided. In certain embodiments, an antibody of the invention is tested for such a property (e.g., physical property) or activity (e.g., biological activity).

1. Antibody Affinity

In certain embodiments, an anti-hypusine antibody provided herein that binds to a hypusine in a polypeptide has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In some embodiments, an anti-hypusine antibody provided herein that binds to a hypusine in a polypeptide has a dissociation constant ($K_D$) of 1 nM or less, 10 nM or less, 20 nM or less, 40 nM or less, 60 nM or less, 80 nM or less, 100 nM or less, 150 nM or less, 200 nM or less, 250 nM or less, 300 nM or less, 350 nM or less, 400 nM or less, 450 nM or less, 500 nM or less, 550 nM or less, 600 nM or less, 650 nM or less, 700 nM or less, 750 nM or less, 800 nM or less, or 900 nM or less. In some embodiments, an anti-hypusine antibody provided herein that binds to a hypusine in a polypeptide has a dissociation constant ($K_D$) of 1 mM or less, 5 mM or less, 10 mM or less, 15 mM or less, 20 mM or less, 25 mM or less, 30 mM or less, 35 mM or less, 40 mM or less, 45 mM or less, 50 mM or less, 55 mM or less, 60 mM or less, 65 mM or less, 70 mM or less, 75 mM or less, 80 mM or less, 85 mM or less, 90 mM or less, 95 mM or less, or 100 mM or less. In certain embodiments, an anti-hypusine antibody provided herein that binds to a hypusine in a polypeptide has a $K_D$ as shown in Table 2 herein. In certain embodiments, an anti-hypusine antibody described herein does not bind to deoxyhypusine in a polypeptide. In a further embodiment, the anti-hypusine antibody that does not bind to deoxyhypusine in a polypeptide exhibits a binding affinity ($K_D$) at least 900 nM or less against the polypeptide containing hypusine. In certain embodiments, an anti-hypusine antibody described herein binds to deoxyhypusine in a polypeptide. In a further embodiment, an anti-hypusine antibody that binds to deoxyhypusine exhibits (i) a binding affinity ($K_D$) of 300 nM or less against the polypeptide containing hypusine and (ii) a binding affinity ($K_D$) of 200 nM or less against the polypeptide containing deoxyhypusine. In certain embodiments, an anti-hypusine antibody provided herein that binds to a deoxyhypusine in a polypeptide has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In some embodiments, an anti-hypusine antibody provided herein that binds to a deoxyhypusine in a polypeptide has a dissociation constant ($K_D$) of 1 nM or less, 5 nM or less, 10 nM or less, 15 nM or less, 20 nM or less, 30 nM or less, 40 nM or less, 50 nM or less, 60 nM or less, 70 nM or less, 80 nM or less, 90 nM or less, 100 nM or less, 110 nM or less, 120 nM or less, 130 nM or less, 140 nM or less, 150 nM or less, 160 nM or less, 170 nM or less, 180 nM or less, 190 nM or less, or 200 nM or less. In some embodiments, an anti-hypusine antibody provided herein that binds to a deoxyhypusine in a polypeptide has a dissociation constant ($K_D$) of 1 mM or less, 5 mM or less, 10 mM or less, 15 mM or less, 20 mM or less, 25 mM or less, 30 mM or less, 35 mM or less, 40 mM or less, 45 mM or less, 50 mM or less, 55 mM or less, 60 mM or less, 65 mM or less, 70 mM or less, 75 mM or less, 80 mM or less, 85 mM or less, 90 mM or less, 95 mM or less, or 100 mM or less. In certain embodiments, an anti-hypusine antibody provided herein that binds to a deoxyhypusine in a polypeptide has a $K_D$ as shown in Table 2 herein. In some embodiments herein, the anti-hypusine antibody comprises a heavy chain variable region comprising a sequence having at least 90% sequence identity to the amino acid sequence of SEQ ID NO:24 or 25; and/or a light chain variable region comprising a sequence having at least 90% sequence identity to the amino acid sequence of SEQ ID NO:20 or 21. In some embodiments herein, the anti-hypusine antibody comprises a heavy chain variable region comprising a sequence having at least 95% sequence identity to the amino acid sequence of SEQ ID NO:26; and/or a light chain variable region comprising a sequence having at least 95% sequence identity to the amino acid sequence of SEQ ID NO:22. In some embodiments herein, the anti-hypusine antibody comprises a heavy chain variable region comprising a sequence having at least 95% sequence identity to the amino acid sequence of SEQ ID NO:27 or 28; and/or a light chain variable region comprising a sequence having at least 95% sequence identity to the amino acid sequence of SEQ ID NO:23. In some embodiments, the antibody is a monoclonal antibody. In some embodiments, the antibody is an antigen-binding fragment.

In one embodiment, $K_D$ is measured using a BIACORE® surface plasmon resonance assay. For example, an assay using a BIACORE® T200 (Biacore, Uppsala, Sweden) is performed with CM5 chips coated with NeutrAvidin at approximately 300 response units (RU) and capturing biotinylated antigen (e.g., polypeptide containing hypusine) at <10 RU. In one embodiment, an anti-hypusine antibody described herein (e.g., anti-hypusine Fab fragment) is serially diluted in 10 mM HEPES, pH 7.4, 0.15 M NaCl and 0.005% Surfactant P20 before injection to flow over immobilized peptides (e.g., peptide containing hypusine). Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams.

The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-hypusine antibody (Fab form) in PBS, pH 7.2, in the presence of increasing concentrations of antigen (e.g., polypeptide containing hypusine) as measured in a spectrometer, such as a stop-flow equipped spectrophotometer (Aviv Instruments) or a 8000-series SLM-AMINCO™ spectrophotometer (ThermoSpectronic) with a stirred cuvette.

2. Binding Assays and Other Assays

In one aspect, an anti-hypusine antibody of the invention is tested for its antigen binding activity, e.g., by known methods such as enzyme-linked immunosorbent assay (ELISA), Western blot, radioimmunoassay, surface plasmon resonance, chromatography, immunoprecipitation, immunofluorescence, fluorescence-activated cell sorting, etc.

In another aspect, competition assays may be used to identify an antibody that competes with an antibody described herein (e.g., Hpu98) for binding to hypusine and/or deoxyhypusine in a polypeptide. In certain embodiments, such a competing antibody binds to the same epitope (e.g., a linear or a conformational epitope) that is bound by an anti-hypusine antibody described herein (e.g., Hpu98). Detailed exemplary methods for mapping an epitope to which an antibody binds are provided in Morris (1996) "Epitope Mapping Protocols," in Methods in Molecular Biology vol. 66 (Humana Press, Totowa, NJ).

In an exemplary competition assay, immobilized polypeptide containing hypusine is incubated in a solution comprising a first labeled antibody that binds to hypusine in a polypeptide (e.g., Hpu24) and a second unlabeled antibody that is being tested for its ability to compete with the first antibody for binding to a hypusine in a polypeptide. The second antibody may be present in a hybridoma supernatant. As a control, immobilized polypeptide containing hyspusine is incubated in a solution comprising the first labeled antibody but not the second unlabeled antibody. After incubation under conditions permissive for binding of the first antibody to a polypeptide containing hypusine, excess unbound antibody is removed, and the amount of label associated with immobilized polypeptide containing hypusine is measured. If the amount of label associated with immobilized polypeptide containing hypusine is substantially reduced in the test sample relative to the control sample, then that indicates that the second antibody is competing with the first antibody for binding to hypusine in a polypeptide. See Harlow and Lane (1988) *Antibodies: A Laboratory Manual* ch. 14 (Cold Spring Harbor Laboratory, Cold Spring Harbor, NY). In some embodiments, the polypeptide contains deoxyhypusine. In some embodiments, the first antibody binds to deoxyhypusine in a polypeptide. In some embodiments, the second antibody binds to hypusine in a polypeptide.

In another aspect, an assay may be used to identify anti-hypusine antibodies described herein such as the binding assay described in Example 1. In some embodiments, a sample containing a candidate anti-hypusine antibody is screened using a method described herein, such as by ELISA. In some embodiments, the sample containing the candidate anti-hypusine antibody is placed in contact with a hypusinated peptide, wherein binding of the candidate anti-hypusine antibody to the hypusinated peptide is detected using standard techniques in the art (e.g., ELISA). In some embodiments, the sample containing the candidate anti-hypusine antibody is placed in contact with a deoxyhypusinated peptide, wherein binding of the candidate anti-hypusine antibody to the deoxyhypusinated peptide is detected using standard techniques in the art (e.g., ELISA). In some embodiments, binding of the candidate anti-hypusine antibody to the hypusinated peptide and/or deoxyhypusinated peptide is compared to binding of the candidate anti-hypusine antibody to a non-hypusinated peptide. In some embodiments, the hypusinated peptide is a hypusinated peptide as shown in Table 1. In some embodiments, the hypusinated peptide is one or more selected from the group consisting of: P1-Hpu (SEQ ID NO:56), P2-Hpu (SEQ ID NO:59), P3-Hpu (SEQ ID NO:62), P4-Hpu (SEQ ID NO:64), P5-Hpu (SEQ ID NO:66) and P6-Hpu (SEQ ID NO:68). In some embodiments, the deoxyhypusinated peptide is a deoxyhypusinated peptide as shown in Table 1. In some embodiments, the deoxyhypusinated peptide is one or more selected from the group consisting of: P1-deoxy (SEQ ID NO:57) and P2-deoxy (SEQ ID NO:60). In some embodiments, the non-hypusinated peptide is a hypusinated peptide as shown in Table 1. In some embodiments, the non-hypusinated peptide is one or more selected from the group consisting of: P1 (SEQ ID NO:58), P2 (SEQ ID NO:61), P3 (SEQ ID NO:63), P4 (SEQ ID NO:65), P5 (SEQ ID NO:67) and P6 (SEQ ID NO:69).

In another aspect, provided herein are assays and methods for selecting pan anti-hypusine antibodies that bind to two or more hypusinated peptides and/or a deoxyhypusinated peptides. In some embodiments, a method for selecting a pan anti-hypusine antibody that binds to two or more hypusinated peptides comprises the steps of a) contacting a candidate antibody with two or more hypusinated peptides selected from the group consisting of: P1-Hpu (SEQ ID NO:56), P2-Hpu (SEQ ID NO:59), P3-Hpu (SEQ ID NO:62), P4-Hpu (SEQ ID NO:64), P5-Hpu (SEQ ID NO:66) and P6-Hpu (SEQ ID NO:68); b) determining if the candidate antibody binds to the two or more hypusinated peptides, wherein binding to the two or more hypusinated peptides indicates that the candidate antibody is a pan anti-hypusine antibody; and c) selecting the pan anti-hypusine antibody. In some embodiments, the method further comprises the step of contacting the selected pan anti-hypusine antibody with one or more deoxyhypusinated peptides selected from the group consisting of: P1-deoxy (SEQ ID NO:57) and P2-deoxy (SEQ ID NO:60) and determining if the pan anti-hypusine antibody binds to the one or more deoxyhypusinated peptides. In some embodiments, the method further comprises the steps of contacting the selected pan anti-hypusine antibody with one or more non-hypusinated peptides selected from the group consisting of: P1 (SEQ ID NO:58), P2 (SEQ ID NO:61), P3 (SEQ ID NO:63), P4 (SEQ ID NO:65), P5 (SEQ ID NO:67) and P6 (SEQ ID NO:69) and determining if the pan anti-hypusine antibody binds to the one or more non-hypusinated peptide. In some embodiments, a method for selecting a pan anti-hypusine antibody that binds to two or more deoxyhypusinated peptides comprises the steps of a) contacting a candidate antibody with two or more deoxyhypusinated peptides selected from the group consisting of: P1-deoxy (SEQ ID NO:57) and P2-deoxy (SEQ ID NO:60); b) determining if the candidate antibody binds to the two or more deoxyhypusinated peptides, wherein binding to the two or more deoxyhypusinated peptides indicates that the candidate antibody is a pan anti-hypusine antibody; and c) selecting the pan anti-hypusine antibody. In some embodiments, the method further comprises the step of contacting the selected pan anti-hypusine antibody with one or more hypusinated peptides selected from the group consisting of: P1-Hpu (SEQ ID NO:56), P2-Hpu (SEQ ID NO:59), P3-Hpu (SEQ ID NO:62), P4-Hpu (SEQ ID NO:64), P5-Hpu (SEQ ID NO:66) and P6-Hpu (SEQ ID NO:68) and determining if the pan anti-hypusine antibody binds to the one or more hypusinated peptides. In some embodiments, the method further comprises the step of contacting the selected pan anti-hypusine antibody with one or more non-hypusinated peptides selected from the group consisting of: P1 (SEQ ID NO:58), P2 (SEQ ID NO:61), P3 (SEQ ID NO:63), P4 (SEQ ID NO:65), P5 (SEQ ID NO:67) and P6 (SEQ ID NO:69) and determining if the pan anti-hypusine antibody binds to the one or more non-hypusinated peptides. In some embodiments, a method for selecting a pan anti-hypusine antibody that binds to one or more deoxyhypusinated peptides and one or more hypusinated peptides comprises the steps of a) contacting a candidate antibody with one or more deoxyhypusinated peptides selected from the group consisting of: P1-deoxy (SEQ ID NO:57) and P2-deoxy (SEQ ID NO:60) and one or more hypusinated peptides selected from the group consisting of: P1-Hpu (SEQ ID NO:56), P2-Hpu (SEQ ID NO:59), P3-Hpu (SEQ ID NO:62), P4-Hpu (SEQ ID NO:64), P5-Hpu (SEQ ID NO:66) and P6-Hpu (SEQ ID NO:68); b) determining if the candidate antibody binds to the one or more deoxyhypusinated peptides and one or more hypusinated peptides, wherein binding to the one or more deoxyhypusinated peptides and one or more hypusinated peptides indicates that the candidate antibody is a pan anti-hypusine antibody; and c) selecting the pan anti-hypusine antibody. In some embodiments, the method further comprises the step of contacting the pan anti-hypusine antibody with one or more non-hypusinated peptides selected from the group consisting of: P1 (SEQ ID NO:58), P2 (SEQ ID NO:61), P3 (SEQ ID NO:63), P4 (SEQ ID NO:65), P5 (SEQ ID NO:67) and P6 (SEQ ID NO:69) and determining if the pan anti-hypusine antibody binds to the one or more non-hypusinated peptides. In some embodiments, a selected pan anti-hypusine antibody binds to hypusine and deoxyhypusine. In some embodiments, a selected pan anti-hypusine antibody binds to hypusine but do not bind to deoxyhypusine.

In some embodiments of the methods for selecting a pan anti-hypusine antibody, step a) comprises testing a single candidate antibody for binding to a hypusinated peptide and/or a deoxyhypusinated peptide. In some embodiments of the methods for selected a pan anti-hypusine antibody, step a) comprises testing a plurality of candidate antibodies for binding to a hypusinated peptide and/or a deoxyhypusinated peptide. In some embodiments of the methods for selected a pan anti-hypusine antibody, step c) comprises selecting one or more pan anti-hypusine antibodies from the plurality of candidate antibodies tested. For example, selecting 1, 2, 3, 4, 5, 6, 7, 8, 9, 10, 15, 20, 25, 30, 35, 40, 45, 50, 55, 60, 65, 70, 75, 80, 85, 90, 95, or 100 but no more than 500 pan anti-hypusine antibodies that bind to a hypusinated peptide and/or a deoxyhypusinated peptide. The plurality of antibodies to be tested in a method of selecting a pan anti-hypusine antibody provided herein can be obtained using any of the numerous approaches in combinatorial antibody library methods known in the art including, but not limited to, a hybridoma library, a phage display library, such as a scFv phage display library prepared using light chain variable domain and heavy chain variable domain cDNAs prepared from mRNA derived from mammalian cells (e.g., human cells, mouse cells, rat cell, rabbit cells, etc.), solution phase libraries, solid phase libraries, and synthetic library methods such as those using affinity chromatography selection. Methodologies for preparing and screening such libraries are known in the art. In addition to commercially available kits for generating hybridoma libraries and phage display libraries (e.g., the Pharmacia *Recombinant Phage Antibody System,* catalog no. 27-9400-01; and the Stratagene SurfZAP™ phage display kit, catalog no. 240612), examples of methods and reagents particularly amenable for use in generating and screening antibody libraries can be found in, for example, Ladner et al. U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; and PCT Publication No. WO 92/09690.

In another aspect, provided herein is a method of producing an anti-hypusine antibody (e.g., pan anti-hypusine antibody) wherein the anti-hypusine antibody binds to a hypusinated peptide. In some embodiments, a method of producing an anti-hypusine antibody that binds to a hypusinated peptide comprises culturing a host cell (e.g., a host cell described herein) comprising a nucleic acid described herein under a condition that produces the anti-hypusine antibody. In some embodiments, the method further comprises recovering the anti-hypusine antibody produced by the host cell. In another aspect, provided herein is a method of producing an anti-hypusine antibody (e.g., a pan anti-hypusine antibody) wherein the anti-hypusine antibody binds to a deoxyhypusinated peptide. In some embodiments, a method of producing an anti-hypusine antibody that binds to a deoxyhypusinated peptide comprises culturing a host cell (e.g., a host cell described herein) comprising a nucleic acid described herein under a condition that produces the anti-hypusine antibody. In some embodiments, the method further comprises recovering the anti-hypusine antibody produced by the host cell. In another aspect, provided herein is a method of producing a pan anti-hypusine antibody that binds to a hypusinated peptide but does not bind to a deoxyhypusinated peptide. In some embodiments, a method of producing a pan anti-hypusine antibody that binds to a hypusinated peptide but does not bind to deoxyhypusinated peptide comprises culturing a host cell (e.g., a host cell described herein) comprising a nucleic acid described herein under a condition that produces the pan anti-hypusine antibody. In some embodiments, the method further comprises recovering the pan anti-hypusine antibody produced by the host cell.

III. Antibody Preparation

The antibody described herein is prepared using techniques available in the art for generating antibodies, exemplary methods of which are described in more detail in the following sections.

1. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthiln, in *The Pharmacology of Monoclonal Antibodies,* vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

2. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

3. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody. Generally, the resulting variant(s) selected for further study will have modifications (e.g., improvements) in certain biological properties (e.g., increased affinity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M.S. et al., Blood 101:1045-1052 (2003); and Cragg, M.S. and M.J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as a detection agent, to create an antibody conjugate as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

4. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:
a) Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC 31,446), E. coli B, E. coliλ 1776 (ATCC 31,537) and E. coli RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for E. coli growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for E. coli, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose. Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

c) Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureus* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NSO, CHOK1 or derivatives, including cell lines deficient in glutamine synthetase (GS). Methods for the use of GS as a selectable marker for mammalian cells are described in U.S. Pat. Nos. 5,122,464 and 5,891,693.

d) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the mouse cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TM cells (Mather et al., Annals N.Y. Acad. Sci. 383:44-68 (1982)); MRC 5 cells; FS4 cells; CHOK1 cells or derivatives and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

IV. Compositions

Compositions or formulations of an anti-hypusine antibody as described herein are prepared by mixing such antibody having the desired degree of purity with one or more optional acceptable carriers (*Remington's Pharmaceutical Sciences* 16th edition, Osol, A. Ed. (1980)), in the form of lyophilized formulations or aqueous solutions. Acceptable carriers are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary acceptable carriers herein further include dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The composition herein may also contain more than one active ingredients (e.g., detection agent, secondary agent, etc.) as necessary. Such active ingredients are suitably present in combination in amounts that are effective for the purpose intended.

Anti-hypusine antibodies may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

V. Methods and Compositions for Diagnostics and Detection

In certain embodiments, any of the anti-hypusine antibodies provided herein are useful for detecting the presence of a hypusine-containing polypeptide in a sample. The term "detecting" as used herein encompasses quantitative or qualitative detection. In certain embodiments, a sample in a biological sample. In the embodiments, the biological sample comprises a cell or tissue, such as tissue from an organ. In some embodiments, the tissue is, but is not limited to, breast tissue, skin tissue, brain tissue, liver tissue, renal tissue, ovarian tissue, uterine tissue, cervical tissue, heart tissue, lung tissue, or lymphoid tissue. In some embodiments, the cell is, but not limited to, a circulating tumor cell, a cell isolated from tissue, a cell line. In some embodiments, the biological sample is a fluid, such as a lavage, cell lysate, plasma, blood, or serum. The samples described herein are processed using routine methods in the art in order to allow detection of polypeptides in the sample.

In one embodiment, an anti-hypusine antibody for use in a method of diagnosis or detection is provided. In a further aspect, a method of detecting the presence of a hypusine-containing polypeptide in a sample is provided. In certain embodiments, the method comprises contacting the sample with an anti-hypusine antibody as described herein under conditions permissive for binding of the anti-hypusine antibody to the hypusine-containing polypeptide, and detecting whether a complex is formed between the anti-hypusine antibody and the hypusine-containing polypeptide. In a further aspect, a method of detecting the presence of a deoxyhypusine-containing polypeptide in a sample is provided. In certain embodiments, the method comprises contacting the sample with an anti-hypusine antibody as described herein under conditions permissive for binding of the anti-hypusine antibody to the deoxyhypusine-containing polypeptide, and detecting whether a complex is formed between the anti-hypusine antibody and the deoxyhypusine-containing polypeptide. Such methods may be an in vitro or in vivo method. In one embodiment, an anti-hypusine antibody is used to select subjects eligible for therapy with a therapeutic agent, e.g. where hypusine and/or deoxyhypusine in a polypeptide is a biomarker for selection of patients.

In certain embodiments, anti-hypusine antibodies comprising a detection agent or linked (also referred to herein as "conjugated") to a detection agent are provided. Detection agents (also referred to as "labels" herein) include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, digoxigenin, and the like. In some embodiments, the detection agent is a chemiluminescent substrate, a chromophore, a fluorophore, a magnetic particle, a dye, a radiolabel, or an enzyme.

Conjugation of the anti-hypusine antibody or secondary agent (e.g., an antibody) to the detecting agent is a standard manipulative procedure in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Conventional methods are available to bind the label moiety covalently to proteins or polypeptides. For example, coupling agents such as dialdehydes, carbodiimides, dimaleimides, bis-imidates, bis-diazotized benzidine, and the like can be used to label antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., 1962, Nature, 144:945; David et al., 1974, Biochemistry, 13:1014-1021; Pain et al., 1981, J. Immunol Methods, 40:219-230; and Nygren J., 1982, Histochem. and Cytochem., 30:407-412.

In some embodiments, an anti-hypusine antibody that is bound to a polypeptide containing hypusine and/or deoxyhypusine is detected using a secondary agent. A secondary agent can be any agent routinely used the art for detection of antibodies. In some embodiments, the secondary agent is an antibody. In some embodiments, the secondary agent is linked to a detection agent described herein.

In one aspect, the invention provides methods for detecting a hypusine-containing polypeptide in a sample comprising the steps of: (a) contacting the sample with an anti-hypusine antibody described herein; and (b) detecting the anti-hypusine antibody bound to the polypeptide in the sample. In some embodiments, the anti-hypusine antibody is linked to a detection agent described herein. In some embodiments, the anti-hypusine antibody bound to the polypeptide is detected using a secondary agent described herein. In some embodiments, the detection agent is a chemiluminescent substrate, a chromophore, a fluorophore, a magnetic particle, a dye, a radiolabel, or an enzyme. In some embodiments, the detection is by one or more assays described herein such as, but not limited to, one or more assays selected from the group consisting of enzyme-linked immunosorbent assay, radioimmunoassay, immunoprecipitation, chromatography, immunohistochemistry, immunofluorescence, surface plasmon resonance, fluorescence-activated cell sorting and mass spectrometry. In some embodiments, the sample is a biological sample as described herein. In some embodiments, the biological sample comprises a cell or tissue. In some embodiments, the biological sample is a fluid.

In one aspect, the invention provides methods for detecting a deoxyhypusine-containing polypeptide in a sample comprising the steps of: (a) contacting the sample with an anti-hypusine antibody described herein; and (b) detecting the anti-hypusine antibody bound to the polypeptide in the sample. In some embodiments, the anti-hypusine antibody is linked to a detection agent described herein. In some embodiments, the anti-hypusine antibody bound to the polypeptide is detected using a secondary agent described herein. In some embodiments, the detection agent is a chemiluminescent substrate, a chromophore, a fluorophore, a magnetic particle, a dye, a radiolabel, or an enzyme. In some embodiments, the detection is by one or more assays described herein such as, but not limited to, one or more assays selected from the group consisting of enzyme-linked immunosorbent assay, radioimmunoassay, immunoprecipitation, chromatography, immunohistochemistry, immunofluorescence, surface plasmon resonance, fluorescence-activated cell sorting and mass spectrometry. In some embodiments, the sample is a biological sample as described herein. In some embodiments, the biological sample comprises a cell or tissue. In some embodiments, the biological sample is a fluid.

Methods known in the art may be used to detect binding between the anti-hypusine antibodies and the hypusine and/or deoxyhypusine-containing polypeptide. ELISA, surface plasmon resonance (e.g., BIAcore®), Immunocap®, RIA (RadioImmunoAssay), immunoprecipitation, chromatography, immunohistochemistry, immunofluorescence, fluorescence-activated cell sorting, and mass spectrometry assays may be used. The assays may be homogeneous, semi-homogeneous, or non-homogeneous. For example, most ELISAs utilize antibodies and/or ligands for capture and detection of a target protein. These ELISAs can utilize either homogeneous, semi-homogeneous, or non-homogeneous assay formats to maximize sensitivity or reduce matrix interference.

Homogeneous assays utilize a format where both the capture agent (e.g., anti-hypusine antibodies) and detection agent (e.g., detection agent, secondary agent, etc.) are pre-incubated simultaneously with the matrix sample containing the target protein (e.g., a hypusine and/or deoxyhypusine-containing polypeptide) in a liquid-phase reaction. The capture agent-target protein-detection agent complex is then captured on a solid-phase (such as a streptavidin-coated ELISA plate), washed, and quantitated by detecting the amount of the detection agent captured to the surface (e.g., by the addition of an appropriate substrate solution if the detection agent is an enzyme). Semi-homogeneous assays utilize a format where the capture agent alone is pre-incubated with the matrix sample in a liquid-phase reaction. This capture agent-target protein complex is then captured on a solid phase, washed, then incubated with a detection agent, washed, and quantitated. Non-homogeneous assays do not utilize any liquid-phase pre-incubation step, but instead utilize sequential steps. The capture agent is captured to the solid-phase, washed, the matrix sample containing the target protein is then added and bound by the capture agent, washed, bound by the detection reagent, washed, and finally quantitated.

A capture reagent (e.g., an anti-hypusine antibody) can be immobilized to a solid phase by insolubilizing the capture reagent either before the assay procedure, as by adsorption to a water-insoluble matrix or surface (U.S. Pat. No. 3,720,760) or non-covalent or covalent coupling, for example, using glutaraldehyde or carbodiimide cross-linking, with or without prior activation of the support with, for example, nitric acid and a reducing agent as described in U.S. Pat. No. 3,645,852 or in Rotmans et al., 1983, J. Immunol. Methods, 57:87-98, or after the assay procedure. In some embodiments, the capture reagent (e.g., an anti-hypusine antibody) after immobilization is available to bind a target molecule (e.g., a hypusine and/or deoxyhypusine-containing polypeptide) from a sample.

Any solid phase or surface (such as small sheets, Sephadex, polyvinyl chloride, plastic beads, microparticles, assay plates, or test tubes manufactured from polyethylene, and polystyrene) described herein may be used in some embodiments of the methods herein. The solid phase or surface used for immobilization can be any inert support or carrier that is essentially water insoluble and useful in immunoassays, including supports in the form of, for example, surfaces, particles, porous matrices, cellulose polymer sponge (ImmunoCAP®, Phadia), and the like. Examples of commonly used supports include small sheets, Sephadex, polyvinyl chloride, plastic beads, microparticles, assay plates, or test tubes manufactured from polyethylene, polypropylene, polystyrene, and the like. Such supports include 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. In an embodiment the immobilized capture reagent is coated on a microtiter plate, preferably a multi-well microtiter plate that can be used to analyze several samples at one time.

The solid phase is coated with the capture reagent (e.g., an anti-hypusine antibody) that can be linked by a non-covalent or covalent interaction or physical linkage, as desired. Techniques for attachment include those described in U.S. Pat. No. 4,376,110 and the references cited therein. If covalent attachment of the capture reagent to the plate is utilized, the plate or other solid phase can be incubated with a cross-linking agent together with the capture reagent. Commonly used cross-linking agents for attaching the capture reagent to the solid phase substrate include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates capable of forming cross-links in the presence of light. Coated solid phase materials are typically treated with a blocking agent that binds non-specifically to, and saturates, the binding sites to prevent unwanted binding of free analyte molecules to excess binding sites on the wells of the plate. Examples of appropriate blocking agents include, for example, gelatin, bovine serum albumin, egg albumin, casein, and non-fat milk. The blocking treatment typically takes place under conditions of ambient temperatures for about 1-4 hours, preferably about 1.5 to 3 hours.

A sample described herein to be analyzed is diluted as necessary and can be added to the immobilized phase. Buffers that can be used for dilution include for example (a) phosphate buffered saline (PBS) containing 0.5% BSA, 0.05% TWEEN 20™, detergent (P20), 5 mM EDTA, 0.25% Chaps surfactant, 0.2% beta-gamma globulin, and 0.35M NaCl, pH 7.0; (b) PBS containing 0.5% BSA and 0.05% P20; (c) PBS containing 0.5% BSA, 0.05% P20, 5 mM EDTA, and 0.35 M NaCl, pH 6.35; (d) PBS containing 0.5% BSA, 0.05% P20, 5 mM EDTA, 0.2% beta-gamma globulin, and 0.35 M NaCl; (e) PBS containing 0.5% BSA, 0.05% P20, 5 mM EDTA, 0.25% Chaps, and 0.35 M NaCl; and (f) PBS containing 0.5% P20.

Conditions for incubation of sample described herein and capture reagent (e.g., a hypusine antibody) are selected to maximize sensitivity of the assay and to minimize dissociation. Incubation time depends primarily on the temperature.

The pH of incubation buffer used in the methods described herein is chosen to maintain a significant level of specific binding of the capture reagent (e.g., an anti-hypusine antibody) to the analyte (e.g., a polypeptide containing hypusine) being captured. In some embodiments, the pH of the incubation buffer is about 6-9.5 (including pH about 6-7). In some embodiments, the pH of the incubation buffer is about 7.2. Various buffers can be employed to achieve and maintain the desired pH during this step, including borate, phosphate, carbonate, Tris-HCl or Tns-phosphate, acetate, barbital, and the like. The particular buffer employed is usually not critical, however, and in individual assays one buffer may be preferred over another.

The sample can be separated from the immobilized capture reagent (e.g., an anti-hypusine antibody) with a wash solution to remove non-specific molecules, such as polypeptides that do not contain a hypusine and/or deoxyhypusine, from the system. The wash solution is generally a buffer. The incubation buffers described above are suitable wash solutions. The pH of the wash solution is determined as described above for the incubation buffer. In an embodiment, the pH of the wash solution is about 6-9, more preferably about 6-7. Washes can be done one or more times. The temperature of the wash solution is can be from about 0-40° C., more preferably about 4-30° C. An automated plate washer can be utilized.

Following removal of non-specific molecules from the system, such as polypeptides that do not contain a hypusine and/or deoxyhypusine, the captured analyte molecules (e.g., hypusine and/or deoxyhypusine-containing polypeptides) can be contacted with a detecting agent. The temperature and time for contacting the analyte molecule with the detecting agent is dependent primarily on the detection means employed. For example, when horseradish peroxidase (HRP) conjugated to streptavidin (SA-HRP) is used as the means for detection, the detecting agent is preferably incubated with the captured analyte for about 0.5-2 hours, more preferably about 1 hour. The system is washed as described above to remove unbound detecting agent from the system and developed by adding peroxidase substrate and incubating the plate for about 15 minutes at room temperature or until good color is visible. In an embodiment, a molar excess of the detecting agent is added to the system after the unbound analyte has been washed from the system.

The amount of (e.g., a hypusine and/or deoxyhypusine-containing polypeptide) bound to the capture reagent (e.g., anti-hypusine antibody) is determined by washing away unbound detecting agent from the immobilized phase and measuring the amount of detecting agent bound to the analyte using a detection method appropriate to the label. In an embodiment, the label moiety is an enzyme. In the case of enzyme moieties, the amount of developed color is a direct measurement of the amount of captured analyte. For example, when HRP is the label moiety, color is detected by quantifying the optical density (O.D.) absorbance (e.g., at 450 nm). In another embodiment, the quantity of analyte bound to the capture reagent is determined in-directly. The signal of an unlabeled detecting agent can be amplified for detection with an anti-detecting agent antibody conjugated to a label moiety. For example, the signal of an unlabeled mouse antibody that binds the target molecule can be amplified with a sheep anti-mouse IgG antibody labeled with HRP. The label moiety is detected using a detection method appropriate to the label. For example, HRP can be detected by reacting HRP with a calorimetric substrate and measuring the optical density of the reacted substrate at 450 nm absorbance.

The pH and/or temperature of the system can be varied to identify molecules that bind the target molecule.

A positive control may be used to develop the assay, to evaluate assay sensitivity, and/or used a control for the assay. A positive control may be used in any of the methods described herein. In some embodiments, the assay includes testing a positive control anti-hypusine antibody that does not bind to deoxyhypusine. In some embodiments, the assay includes testing a positive control anti-hypusine antibody that binds to hypusine. In some embodiments, binding of the anti-hypusine antibodies to a hypusine and/or deoxyhypusine-containing polypeptide in a sample and binding of the positive control antibody to the hypusine and/or deoxyhypusine-containing polypeptide are detected and compared.

A negative control may be used to develop the assay, to evaluate assay sensitivity, and/or used a control for the assay. A negative control may be used in any of the methods described herein. In some embodiments, the assay includes testing a negative control anti-hypusine antibody that does not bind to deoxyhypusine. In some embodiments, binding of the anti-hypusine antibodies to a hypusine and/or deoxyhypusine-containing polypeptide in a sample and binding of the negative control antibody to the hypusine and/or deoxyhypusine-containing polypeptide are detected and compared.

In one aspect, the invention provides methods for isolating a hypusine-containing polypeptide in a sample comprising the steps of: (a) contacting the sample with an anti-hypusine antibody described herein; and (b) isolating the polypeptide bound to the antibody. In some embodiments, the anti-hypusine antibody is linked to a detection agent described herein. In some embodiments, the anti-hypusine antibody bound to the polypeptide is detected using a secondary agent described herein. In some embodiments, the detection agent is a chemiluminescent substrate, a chromophore, a fluorophore, a magnetic particle, a dye, a radiolabel, or an enzyme. In some embodiments, the detection is by one or more assays described herein such as, but not limited to, one or more assays selected from the group consisting of enzyme-linked immunosorbent assay, radioimmunoassay, immunoprecipitation, chromatography, immunohistochemistry, immunofluorescence, surface plasmon resonance, fluorescence-activated cell sorting and mass spectrometry. In some embodiments, the antibody is immobilized to a solid surface as described herein. In some embodiments, the sample is a biological sample as described herein. In some embodiments, the biological sample comprises a cell or tissue. In some embodiments, the biological sample is a fluid.

In one aspect, the invention provides methods for isolating a deoxyhypusine-containing polypeptide in a sample comprising the steps of: (a) contacting the sample with an anti-hypusine antibody described herein; and (b) isolating the polypeptide bound to the antibody. In some embodiments, the anti-hypusine antibody is linked to a detection agent described herein. In some embodiments, the anti-hypusine antibody bound to the polypeptide is detected using a secondary agent described herein. In some embodiments, the detection agent is a chemiluminescent substrate, a chromophore, a fluorophore, a magnetic particle, a dye, a radiolabel, or an enzyme. In some embodiments, the detection is by one or more assays described herein such as, but not limited to, one or more assays selected from the group consisting of enzyme-linked immunosorbent assay, radioimmunoassay, immunoprecipitation, chromatography, immunohistochemistry, immunofluorescence, surface plasmon resonance, fluorescence-activated cell sorting and mass spectrometry. In some embodiments, the antibody is immobilized to a solid surface as described herein. In some embodiments, the sample is a biological sample as described herein. In some embodiments, the biological sample comprises a cell or tissue. In some embodiments, the biological sample is a fluid.

Hypusine-containing polypeptide and deoxyhypusine-containing polypeptides can be isolated using standard techniques in the art such as those described herein. For example, hypusine-containing polypeptide and deoxyhypusine-containing polypeptides can be isolated by immunoaffinity or ion-exchange columns, ethanol precipitation, reverse phase HPLC, chromatography on silica or on a cation-exchange resin, chromatofocusing, SDS-PAGE, ammonium sulfate precipitation, and gel filtration.

Isolated hypusine-containing polypeptides and deoxyhypusine-containing polypeptides can be identified using standard techniques in the art. For example, the amino acid sequence of the isolated polypeptide can be obtained by standard sequencing methods. As another example, physical properties of the isolated polypeptides can also be determined by using mass spectrometry.

VI. Articles of Manufacture or Kits

The invention also provides kits for use in the methods described herein.

In one aspect, the invention provides kits comprising an anti-hypusine antibody described herein or compositions thereof. In some embodiments, the kit further comprises one or more agents for the use of the anti-hypusine antibody in a method for detecting a hypusine-containing polypeptide in a sample. In some embodiments, the kit further comprises one or more agents for the use of the anti-hypusine antibody in a method for detecting a deoxyhypusine-containing polypeptide in a sample. In some embodiments, the one or more agents is a buffer, solid surface, detection agent, a secondary agent, positive control or negative control described herein. In some embodiments, the positive control comprises a hypusine-containing polypeptide. In some embodiments herein, the negative control comprises a nonhypusine-containing polypeptide. In some embodiments herein, the positive control is a deoxyhypusine-containing polypeptide. In some embodiments herein, the negative control is a nondeoxyhypusine-containing polypeptide. In some embodiments, the sample is a biological sample. In some embodiments, the biological sample contains a cell or tissue. In some embodiments, the biological sample is a fluid.

In one aspect, the invention provides kits comprising an anti-hypusine antibody described herein or compositions thereof. In some embodiments, the kit further comprises one or more agents for the use of the anti-hypusine antibody in a method for isolating a hypusine-containing polypeptide in a sample. In some embodiments, the kit further comprises one or more agents for the use of the anti-hypusine antibody in a method for isolating a deoxyhypusine-containing polypeptide in a sample. In some embodiments, the one or more agents is a buffer, solid surface, detection agent, a secondary agent, positive control or negative control described herein. In some embodiments, the positive control comprises a hypusine-containing polypeptide. In some embodiments herein, the negative control comprises a nonhypusine-containing polypeptide. In some embodiments herein, the positive control is a deoxyhypusine-containing polypeptide. In some embodiments herein, the negative control is a nondeoxyhypusine-containing polypeptide. In some embodiments, the sample is a biological sample. In some embodiments, the biological sample contains a cell or tissue. In some embodiments, the biological sample is a fluid.

In some of the embodiments herein, the kit comprises an anti-hypusine antibody linked to a detection agent described herein. In some embodiments, the detection agent is a chemiluminescent substrate, a chromophore, a fluorophore, a magnetic particle, a dye, a radiolabel, or an enzyme.

The kits of the invention may further comprise any instructions for use in accordance with any of the methods described herein. In some embodiments, the instructions comprise a description of detecting a hypusine-containing polypeptide in a sample with an anti-hypusine antibody according to any methods described herein. In some embodiments, the instructions comprise a description of isolating a hypusine-containing polypeptide in a sample with an anti-hypusine antibody according to any methods described herein. In some embodiments, the instructions comprise a description of detecting a deoxyhypusine-containing polypeptide in a sample with an anti-hypusine antibody according to any methods described herein. In some embodiments, the instructions comprise a description of isolating a deoxyhypusine-containing polypeptide in a sample with an anti-hypusine antibody according to any methods described herein. The instructions may be provided on a label or package insert. Kits may optionally comprise additional components such as buffers and reagents for carrying out the methods described herein.

The reagents of the kits (such as an anti-hypusine antibody) may be in a container. The kits of the invention are in suitable packaging. Suitable packaging includes, but is not limited to, vials, bottles, jars, flexible packaging (e.g., sealed Mylar or plastic bags), and the like. Also contemplated are packages for use in combination with a specific device, such as a device for signal detection in an ELISA assay.

The following are examples of the methods and compositions of the invention. It is understood that various other embodiments may be practiced, given the general description provided above.

EXAMPLES

Example 1

Anti-Hypusine Antibody Identification and Characterization

Anti-hypusine antibodies that bind to hypusine in a polypeptide with minimal dependence on the surrounding amino acid sequences were generated. Such anti-hypusine antibodies are also referred to herein as "pan anti-hypusine antibodies."

Materials and Methods

Fab Production and Purification

An orthogonally protected hypusine reagent for automated solid-phase synthesis of hypusinated peptides with dramatically improved yield and >95% purity was previously developed (Song et al., *J. Org. Chem.*, 80:3677-3681, 2015). To generate pan-hypusine antibodies, 10 rabbits were immunized with a cocktail of keyhole limpet hemocyanin or thyroglobulin-conjugated I1 and I2 peptides (YenZym Antibodies, South San Francisco, CA). After 3 rounds of immunization with 3 weeks between boosts, rabbits were screened by ELISA for their selectivity of binding to hypusine-containing peptides over corresponding non-hypusinated peptides. Four rabbits with the highest selectivity of binding were subjected to one additional round of immunization. Rabbit monoclonal antibodies were then generated (Abeam, Burlingame, CA) (Chen et al., J. Virol., 87:10232-10243, 2013). Supernatants from hybridoma wells were screened by ELISA for binding to hypusinated and matched non-hypusinated peptides (Table 1). Five hybridoma clones, which were able to bind all the hypusinated peptides with flanking sequences, for example hypusinated eIF5A peptide, were selected for further characterization.

TABLE 1

Summary of Hypusinated Peptides[1]

| Application and peptide name | Peptide Sequence | SEQ ID NO: |
|---|---|---|
| Immunization | | |
| I1 | Hpu-peg$_6$-C | SEQ ID NO: 54 |
| I2 | GSG-Hpu-GSG-peg$_6$-C | SEQ ID NO: 55 |
| Screening | | |
| P1-Hpu | biotin-peg$_6$-GSG-Hpu-GSG | SEQ ID NO: 56 |
| P1-deoxy | biotin-peg$_6$-GSG-deoxyHpu-GSG | SEQ ID NO: 57 |
| P1 | biotin-peg$_6$-GSG-K-GSG | SEQ ID NO: 58 |
| P2-Hpu | biotin-peg$_6$-STSKTG-Hpu-HGHAK | SEQ ID NO: 59 |
| P2-deoxy | biotin-peg$_6$-STSKTG-deoxyHpu-HGHAK | SEQ ID NO: 60 |
| P2 | biotin-peg$_6$-STSKTG-K-HGHAK | SEQ ID NO: 61 |
| P3-Hpu | biotin-GG-DEEAL-Hpu-QLAEWVS | SEQ ID NO: 62 |
| P3 | biotin-GG-DEEAL-K-QLAEWVS | SEQ ID NO: 63 |
| P4-Hpu | biotin-GG-AAAA-Hpu-AAAA-Hpu-AAAA-Hpu-A | SEQ ID NO: 64 |
| P4 | biotin-GG-AAAA-Hpu-AAAA-K-AAAA-Hpu-A | SEQ ID NO: 65 |
| P5-Hpu | GW-Hpu-PMSRSSGRVYYFNGG-biotin | SEQ ID NO: 66 |
| P5 | GW-K-PMSRSSGRVYYFNGG-biotin | SEQ ID NO: 67 |
| P6-Hpu | biotin-GGLLELD-Hpu-WASLW | SEQ ID NO: 68 |
| P6 | biotin-GGLLELD-K-WASLW | SEQ ID NO: 69 |
| Crystallization | | |
| C1 | GSG-Hpu-GSG | SEQ ID NO: 70 |
| C2 | GSG-deoxyHpu-GSG | SEQ ID NO: 71 |

[1] peg6 indicates polyethylene glycol; Hpu indicates hypusine; deoxyHpu indicates deoxyhypusine. The amino terminus of the peptides are blocked by biotin or by an acetyl group. The carboxy terminus of the peptides are capped by an amide group.

The antibody sequences were obtained by extracting RNA using RNeasy Mini Kit, reverse transcription using SuperScript III RT-PCR system, amplification using a SMARTer RACER 5' kit (Clontech Laboratories) and TA cloning. CHO cells were transfected with plasmid and cultured for two weeks. IgGs were purified by protein A affinity chromatography (5 ml HiTrap Mab Select SuRe column, GE Healthcare). The Fab fragments were prepared by papain digestion. The IgG molecules were incubated with papain at a 20:1 molar ratio in 20 mM phosphate pH 6.5, 150 mM NaCl, 20 mM cysteine hydrochloride and 4 mM EDTA. After 4 hours at 37° C. the reaction was quenched by adding 30 mM iodoacetamide. The Fab fragments were separated from the Fc fragments and the undigested IgG by Mab Select SuRe chromatography and harvesting the flow through. The Fab fragments were further purified on a SuperDex D75 column (GE Healthcare) in 10 mM Tris-HCl 8.0 and 100 mM NaCl.

Specificity of Anti-Hypusine Antibodies to eIF5A

Flag-tagged human WT or K50A eIF5A was expressed in human embryonic kidney 293T cells together with Myc-tagged DHS and HA-tagged DOHH. Transfected 293T cells were lysed in lysis buffer (50 mM Tris-HCl, 150 mM NaCl, 2 mM EDTA, 1% Triton-X100 and Protease inhibitor cocktail, pH 7.4). The supernatant were collected after centrifugation (30 min, 16,000 g and 4° C.). Samples were then analyzed by western blotting to determine the specificity of each anti-hypusine monoclonal antibody.

Results

Hypusine was made as previously described (Song et al., J. Org. Chem., 80:3677-3681, 2015) and used to synthesize a panel of different hypusinated peptides (Table 1). 10 rabbits were immunized alternately with acetyl-hypusine-peg6-C-amide (SEQ ID NO: 54) and acetyl-GSG-hypusine-GSG-peg6-C-amide (SEQ ID NO: 55) peptides conjugated to either keyhole limpet hemocyanin or to thyroglobulin. After 3 rounds of immunization, 4 of 10 rabbits were pursued for monoclonal antibody generation, as they showed a slightly higher response to the hypusine-containing peptides than their non-hypusinated counterparts by ELISA. Unpurified rabbit hybridoma supernatants were screened by ELISA for selective binding to the hypusinated peptides used for immunization and positive wells further screened for binding to a panel of different hypusinated peptides (Table 1). 146 out of 7,680 hybridoma supernatants were found to bind selectively to the hypusinated peptides used for immunization, but not to corresponding non-hypusinated peptides. Five of these 146 hybridoma supernatants bound to all the hypusinated peptides with minimal binding to corresponding non-hypusinated peptides. These 5 rabbit monoclonal antibodies were molecularly cloned, recombinantly expressed, purified and characterized. Three out of these 5 rabbit monoclonal antibodies, mAbHpu24, mAbHpu91 and mAbHpu98, were confirmed to recognize all of the different hypusinated peptides, but not the corresponding non-modified peptides (FIG. 1A-D and FIG. 2A). These results suggest that these anti-hypusine antibodies have the potential to interact with many different hypusinated proteins, independent of the primary sequence and the secondary structure environment of the hypusine, i.e., pan anti-hypusine antibodies.

The anti-hypusine antibodies were characterized for their ability to bind to hypusine in the native intact eIF5A protein. Human embryonic kidney 293 cells were co-transfected with plasmids encoding flag-tagged wild-type (or K50A variant) eIF5A and myc-tagged DHS fused to HA-tagged DOHH via a self-cleaving T2A peptide linker (Ryan et al., J. Gen. Virol., 72:2727-2732, 1991) (FIG. 2B). Whole cell lysates were subjected to SDS-PAGE and Western blot analysis using anti-flag or anti-hypusine antibodies. Wild type and K50A mutant eIF5A proteins were expressed in similar amounts as shown by blotting with anti-flag antibody (FIG. 2C). The 3 anti-hypusine antibodies detected transfected wild-type eIF5A, but not the K50A variant lacking the lysine required for hypusination. The anti-hypusine antibodies also recognized endogenous eIF5A, the majority of which is hypusinated (Park et al., PNAS, 103:51-56, 2006).

The pan-hypusine antibodies were subsequently screened for binding to the biosynthetic intermediate, deoxyhypusine (FIG. 3A). Only FabHpu98 bound deoxyhypusine, although FabHpu91 differs from FabHpu98 by only 8 amino acids in the variable domains (FIG. 1C-D and FIG. 3B). Single amino acid residues from FabHpu91 were introduced at equivalent positions in FabHpu98 to understand the basis for the deoxyhypusine specificity. The FabHpu98 Y52W variant preferred hypusine to deoxyhypusine like FabHpu91, as judged by biolayer interferometry (Octet) (FIG. 3C). The FabHpu91 counterpart was made and found to have improved ability to bind to deoxyhypusine and attenuated ability to bind hypusine (FIG. 3C). Thus, $V_H$ Y52 can function as a switch that determines binding specificity for hypusine and deoxyhypusine.

Example 2

Affinity Maturation of Anti-Hypusine Antibodies

Phage display technology was used to further enhance the affinity of the pan anti-hypusine antibodies.
Materials and Methods
Phage Display for Affinity Maturation To improve phage display of rabbit FabHpu24 and FabHpu98 in *E. coli*, the bacteria codon optimized rabbit FabHpu24 and FabHpu98 sequences were synthesized (Genewiz) and cloned into phage display vector. Phage display libraries were generated by Kunkel mutagenesis (Kunkel et al., *PNAS*, 82:488-492, 1985). In each library, mutations were introduced at every position on the same CDR loop, using degenerate oligonucleotides synthesized with 70-10-10-10 mixtures of nucleotide bases with the wild-type nucleotide in excess. Consequently, the resulting library favors wild-type residues with a frequency of approximately 50%. All phage preparation was done according to standard protocols (Bostrom et al., *Methods Mol. Biol.*, 525:353-376, 2009). Briefly, 96-well Maxisorp plates were coated with 5 µg/ml NeutrAvidin overnight at 4° C. and subsequently blocked with Superblock™ T20 (PBS) blocking buffer for 1 hr at 20° C. For round 1, P1-Hpu peptide was captured on the plate after 10 min shaking in 500 nM concentration. After removing excess peptide, 100 µl library phage ($3 \times 10^{12}$ particles/ml in blocking buffer) was added to each well and the plates were incubated for 1 hr at room temperature. The plates were then washed 10 times with 0.05% (v/v) Tween 20 in PBS. Bound phage were eluted from the plates with 0.1 M HCl and 0.5 M KCl for 20 min, neutralized with an equal volume of 1 M Tris-HCl pH 7.5 and amplified for subsequent rounds. From round 2 onwards, Fab displaying phage were mixed first with a decreasing concentration of biotinylated peptide and captured on the NeutrAvidin-coated wells for 15 min. After several rounds, selected clones were reformatted as IgG and transiently transfected into Expi293 cells (Life Technologies, Grand Island, NY).
Bio-Layer Interferometry Detection of the interaction between peptides and Fabs was conducted with Octet RED 96 system (ForteBio, Menlo Park, CA) by biolayer interferometry. The peptides were immobilized on streptavidin-coated sensor tips (ForteBio). Prior to use, the sensor tips were soaked for 1 min 1× kinetics buffer. The Fabs were adjusted to a concentration of 200 nM. The microplates used in the Octet were filled with 200 µl of buffer or samples per well. Data were generated automatically by the Octet Data Acquisition 7.0 software.
Surface Plasmon Resonance Analysis Surface plasmon resonance data were measured on a Biacore model T200 (Biacore, Uppsala, Sweden). A Biacore CM5 chip was coated with NeutrAvidin at ~300 RU and biotinylated antigens were captured <10 RU. Serial dilutions of the Fab fragments in 10 mM HEPES pH 7.4, 0.15 M NaCl and 0.005% Surfactant P20 were flowed over the immobilized peptides and 1:1 Langmuir binding models were used to calculate the $k_{on}$, $k_{off}$ and $K_D$ for each Fab:antigen pair.
Immunoprecipitation of eIF5A 4 plates (150 mm) of sub-confluent 293T cells were harvested and lysed in 5 ml ice-cold lysis buffer (50 mM Tris-HCl, 150 mM NaCl, 2 mM EDTA, 1% Triton-X100 and protease inhibitor cocktail, pH 7.4). The supernatant was collected after centrifugation (30 min, $5 \times 10^4$ g, 4° C.), and diluted 1, 2, 4 or 8-fold. Samples (500 µl) from each dilution were added to 50 µl protein A dynabeads (Invitrogen) preloaded with 5 µg purified mAbHpu24, mAbHpu24.B, mAbHpu98 or mAbHpu98.61, and incubated at 4° C. for 4 hr. The beads were then washed 3 times with lysis buffer and incubated with 50 µl 1× NuPAGE LDS Sample Buffer at 70° C. for 10 min. After electrophoresis proteins were visualized by Coomassie blue staining.
Results The binding affinity ($K_D$) of FabHpu98 and FabHpu24 to the P1 hypusinated peptide (Table 2) are ~113 nM and ~192 nM, respectively. Previous studies have shown that the eIF5A is an abundant hypusinated protein in many different cells types (Cooper et al., *Cell*, 29:791-797, 1982). High affinities of antibodies to hypusine are desirable to increase the likelihood of identifying low abundance hypusinated proteins.

To potentially better support the core hydrogen bond network for anchoring hypusine, engineering was focused on peripheral CDR residues. Based on the structures of complexes (see Example 3), CDRs L1, L2, H2 of FabHpu24 and CDRs H1, H2, L3 of FabHpu98 were diversified. After several rounds of phage library selection using biotin-peg6-GSG-hypusine-GSG (P1) peptide and sequence analysis, clones of interest were expressed in Expi293 cells as Fab fragments, purified and tested by SPR for binding to hypusine. Combination of the improved $V_L$ and $V_H$ sequences (L1, L2, H2) resulted in the FabHpu24.B variant, which had 32-fold higher binding affinity than its parental clone for the hypusinated peptide, P1 (FIG. 1A-B). FabHpu24.B maintained specificity to hypusine with a $K_D$ of 6 nM with only very weak binding to deoxyhypusine (Table 2). By contrast, affinity maturation of FabHpu98 to yield FabHpu98.61 gave high affinity binding to both hypusine (18 nM $K_D$) and deoxyhypusine (20 nM $K_D$) (FIG. 1C-D and Table 2).

TABLE 2

Binding Constants for Pan Anti-Hypusine Fab Fragments[1]

| Peptide | FabHpu-24 $K_D$ (nM) | FabHpu-24.B $K_D$ (nM) | Fold | FabHpu-98 $K_D$ (nM) | FabHpu-98.61 $K_D$ (nM) | Fold |
|---|---|---|---|---|---|---|
| P1-Hpu | 192 ± 35 | 6 ± 2 | 32 | 119 ± 60 | 15 ± 3 | 7.9 |
| P1-deoxyHpu | >1000 | >1000 | | 118 ± 61 | 17 ± 4 | 6.9 |
| P1 | >1000 | >1000 | | >1000 | >1000 | |
| P2-Hpu | 157 ± 12 | 13 ± 5 | 12 | 204 ± 40 | 78 ± 14 | 2.6 |
| P2-deoxyHpu | >1000 | >1000 | | 158 ± 13 | 86 ± 22 | 1.8 |
| P2 | >1000 | >1000 | | >1000 | >1000 | |
| P3-Hpu | >1000 | 186 ± 60 | >5 | >1000 | >1000 | |
| P3 | >1000 | >1000 | | >1000 | >1000 | |

TABLE 2-continued

Binding Constants for Pan Anti-Hypusine Fab Fragments[1]

| Peptide | FabHpu-24 K$_D$ (nM) | FabHpu-24.B K$_D$ (nM) | Fold | FabHpu-98 K$_D$ (nM) | FabHpu-98.61 K$_D$ (nM) | Fold |
|---|---|---|---|---|---|---|
| P4-Hpu | 541 ± 331 | 32 ± 15 | 17 | 228 ± 43 | 91 ± 16 | 2.5 |
| P4 | >1000 | >1000 | | >1000 | >1000 | |
| P5-Hpu | 96 ± 19 | 7 ± 3 | 13 | 176 ± 33 | 70 ± 21 | 2.5 |
| P5 | >1000 | >1000 | | >1000 | >1000 | |
| P6-Hpu | 176 ± 55 | 61 ± 11 | 2.9 | >1000 | 229 ± 40 | >4.4 |
| P6 | >1000 | >1000 | | >1000 | >1000 | |

[1]Hpu indicates hypusine; deoxyHyu indicates deoxyhypusine. Affinity measurements (mean ± SD) were made by surface plasmon resonance. Fold improvement (shown as "Fold") in binding affinity was calculated as the ratio of K$_D$ values of the parent and corresponding affinity-matured antibodies.

Based on the structures, the mutations are located at the peripheral CDR loops and are not anticipated to contact other residues in the peptides. To assess whether increased affinity was due to improved interaction with hypusine or flanking sequences the selected Fab were evaluated against 6 pairs of hypusinated or non-hypusinated peptides (FIG. 4A-B, FIG. 5A-E and FIG. 6A-F). The affinity-matured IgGs can bind to all hypusinated peptides with higher maximal binding (Rmax) than their parental clones, but not the matched non-hypusinated peptides (Table 2). The anti-hypusine antibodies have a slight sequence preference, e.g., FabHpu98.61 binds weakly to P3 hypusine-containing peptide, whereas it has much better response to other peptides (FIG. 6A-F). Thirdly, FabHpu24.B has the best binding to the hypusinated peptides, while FabHpu98.61 retains the ability to bind deoxyhypusine-containing peptides. Hence, the combination of FabHpu24.B and FabHpu98.61 appear suitable for the discovery of different potential hypusine-modified and deoxyhypusine-modified proteins.

To study whether affinity-matured antibodies would result in increased efficiency in pulling down potential hypusinated proteins, mAbHpu24, mAbHpu24.B, mAbHpu98 and mAbHpu98.61 were used to immunoprecipitate endogenous eIF5A protein from a series of 293T cell lysate dilutions. The parental mAbHpu24 immunoprecipitated eIF5A in all the lysate dilutions, while mAbHpu24.B with a 12-fold improvement in affinity dramatically enhanced the recovery of eIF5A (FIG. 7A-B). Furthermore, mAbHpu98.61 also greatly outperformed mAbHpu98 in recovering eIF5A, even though mAbHpu98.61 only had 2-folds affinity improvement in binding to P2-Hpu peptide (FIG. 7A-B, Table 2). Therefore, affinity matured pan-hypusine antibodies may be more efficient to enrich potential novel low abundance hypusinated proteins.

Example 3

Structural Analysis of Antibodies Complexed with Hyspusinated Peptides or Deoxyhypusinated Peptides Pan anti-hypusine antibodies in complex with hypusinated or deoxyhypusinated peptides were characterized by structural analysis.

Materials and Methods

X-Ray Crystallographic Structural Analysis

Purified FabHpu24 was concentrated to 10 mg/ml and mixed with acetyl-GSG-hypusine-GSG-amide peptide (SEQ ID NO: 70) at 1:2 molar ratio before crystallization by the sitting-drop method. The optimized crystallization condition for complexes of FabHpu24 is 20% polyethylene glycol (peg) 3350, 0.1 M bis-tris propane pH 7.0 and 0.2 M potassium/sodium phosphate at 4° C. For data collection, crystals were soaked briefly in the cryoprotectant solution (25% glycerol, 20% peg 3350, 0.1 M bis-tris propane pH 7.0 and 0.2 M potassium/sodium phosphate) before flash freezing in liquid nitrogen, and the data set was collected at beam line ALS 5.0.2.

Purified FabHpu24.B was concentrated to 10 mg/ml and mixed with acetyl-GSG-hypusine-GSG-amide peptide (C1) (SEQ ID NO: 70) at 1:4 molar ratio before crystallization by the sitting-drop method. The optimized crystallization condition for complexes of FabHpu24.B is 14% peg 6000, 0.5 M NaCl at 19° C. For data collection, crystals were soaked briefly in the cryoprotectant solution (35% ethylene glycol, 14% peg 6000, 0.5 M NaCl and 1 mM C1 peptide), before flash freezing in liquid nitrogen, and the data set was collected at beam line ALS 5.0.2.

Purified FabHpu98 was concentrated to 15 mg/ml and mixed with acetyl-GSG-hypusine-GSG-amide peptide (C1) (SEQ ID NO: 70) or acetyl-GSG-deoxyhypusine-GSG peptide (C2) (SEQ ID NO: 71) at 1:4 molar ratio before crystallization by the sitting-drop method. The optimized crystallization condition for complexes of FabHpu98 is 20% peg 8000 and 0.5 M Li$_2$SO$_4$ at 4° C. For data collection, crystals were soaked briefly in the cryoprotectant solution (30% ethylene glycol, 5% peg 8000, 0.4 M Li$_2$SO$_4$, 30% ethylene glycol and 1 mM of the corresponding peptide), before flash freezing in liquid nitrogen, and the data set was collected at beamline 22-IDG at the Advanced Photon Source (APS).

All X-ray diffraction data sets were processed with the HKL2000 software package (Otwinowski et al., Processing of X-ray Diffraction Data Collected in Oscillation Mode. In Macromolecular Crystallography, Academic Press, pp. 307-326, 1997). The structures were determined by molecular replacement with Phaser in the Phenix software package with a starting model built on a homologous Fab (Protein Data Bank [PDB] 4HBC) (Adams et al., *Acta Crystallogr. D Biol. Crystallogr.*, 66:213-221, 2010 and McCoy et al., *J. Appl. Crystallogr.* 40:658-674, 2007).

Results

FabHpu24-Hypusinated Peptide Complex

Figures 8A, 8B:
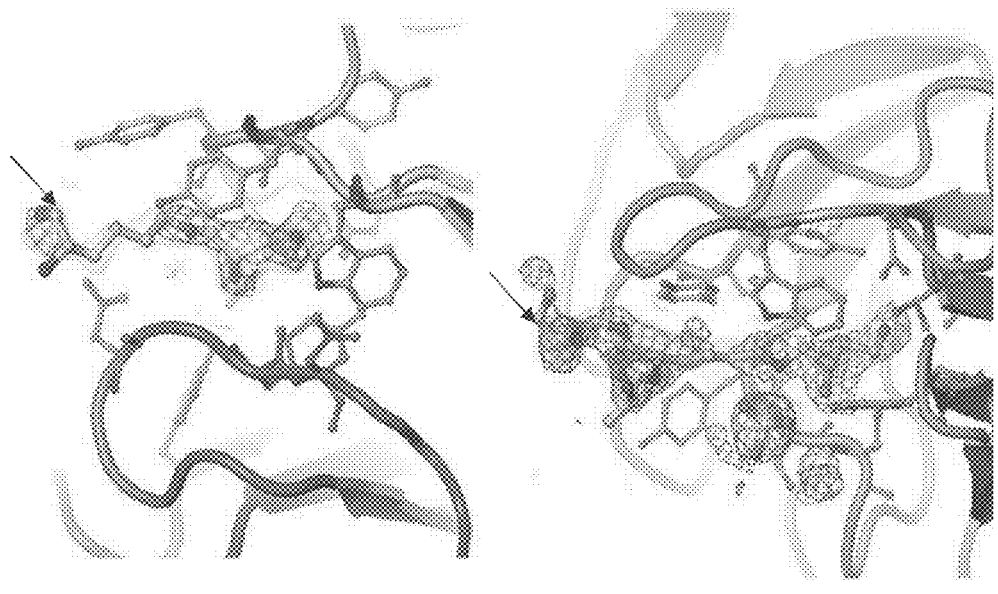
FIGS. 8A-8B is an electron density map of the hypusine-containing peptides bound to Fab fragments.
Figures 9A, 9B:
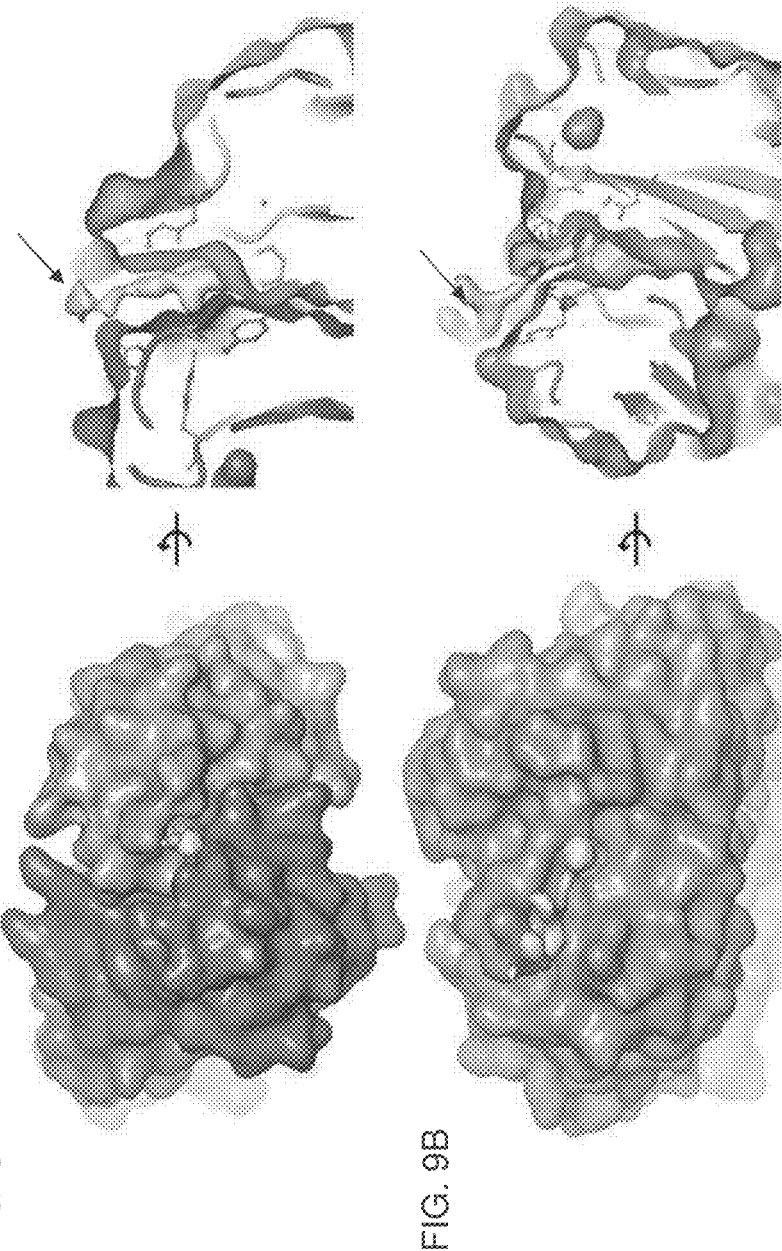
FIGS. 9A-9B is a series of diagrams showing alternative binding modes of FabHpu24 and FabHpu98 with hypusine.

An X-ray crystallographic structure of FabHpu24-hypusinated C1 peptide complex was determined at 2.0 Å resolution to gain molecular insight into antibody binding to hypusine (Table 3). The complex crystallized in P21 space group with two every similar FabHpu24-hypusine complexes in the asymmetric unit (rmsd of 0.15 Å). The 4-amino-2-hydroxybutyl group of the hypusine was clearly visible in the simulated annealing mFo-dFc omit electron density map (FIG. 8A), but not the rest of hypusine. These observations suggested that FabHpu24 bound only to hypusine and not to flanking amino acid residues. Indeed, hypusine was inserted into a deep pocket formed by the heavy chain and the light chain variable domains of FabHpu24 (FIG. 9A). The hypusine-binding pocket buried a total solvent-exposed surface area of ~301 Å$^2$ with 112 Å$^2$ and 189 Å$^2$ contributed by V$_H$ and V$_L$ chains, respectively.

TABLE 3

Structure data summary and Refinement Statistics[1]

| | Hypusine-FabHpu24 | Hypusine-FabHpu24.B | Hypusine-FabHpu98 | DeoxyHypusine-FabHpu98 | Hypusine-FabHpu98.61 |
|---|---|---|---|---|---|
| Data Collection | | | | | |
| Space group | P21 | P21 | C222 | C222 | C2 |
| Cell dimensions | | | | | |
| a, b, c (Å) | 42.4, 167.3, 68.3 | 69.1, 168.0, 84.9 | 106.0, 294.1, 68.7 | 105.6, 294.0, 68.8 | 130.1, 75.8, 120.6 |
| α, β, γ (°) | 90, 98.9, 90 | 90, 99.7, 90 | 90, 90, 90 | 90, 90, 90 | 90, 120.7, 90 |
| Resolution (Å) | 50-1.85 (1.92-1.85) | 50-2.40 (2.49-2.40) | 50.0-1.95 (2.0-1.95) | 50.0-2.0 (2.07-2.00) | 40.0-1.9 (2.0-1.9) |
| Rsym (%) | 6.6 (54.5) | 7.4 (52.9) | 7.5 (78.5) | 7.5 (88.4) | 9.0 (55.2) |
| $CC_{1/2}$ in the highest shell | 0.719 | 0.776 | 0.615 | 0.605 | 0.808 |
| $<I>/<\sigma(I)>$ | 30.7 (2.0) | 15.4 (2.3) | 22.0 (2.2) | 16.0 (2.2) | 9.9 (2.1) |
| Completeness (%) | 99.9 (99.9) | 100 (99.9) | 99.8 (99.0) | 99.9 (99.8) | 97.7 (95.3) |
| Redundancy | 3.8 (3.6) | 1.9 (1.9) | 7.4 (6.5) | 7.1 (5.6) | 3.4 (3.3) |
| Refinement | | | | | |
| Resolution (Å) | 43.0-2.0 | 49.0-2.4 | 41.2-1.95 | 42.9-1.98 | 37.2-1.9 |
| No. of unique reflections | 79689 | 74274 | 78403 | 74438 | 77821 |
| No. Fabs | 2 | 4 | 2 | 2 | 2 |
| No. bound peptides | 2 | 4 | 1 | 1 | 2 |
| Rwork/Rfree (%) | 19.2/22.5 | 20.1/24.8 | 17.7/21.8 | 17.9/22.3 | 21.2/24.9 |
| No. atoms | | | | | |
| Protein | 6392 | 12730 | 6423 | 6429 | 6289 |
| Solvent | 266 | 277 | 262 | 155 | 254 |
| r.m.s deviations | | | | | |
| Bond lengths (Å) | 0.006 | 0.004 | 0.013 | 0.013 | 0.005 |
| Bond angles (°) | 1.02 | 0.882 | 1.48 | 1.48 | 1.083 |
| Ramachandran | | | | | |
| Favored (%) | 96.2 | 96.3 | 97.5 | 96.7 | 97.2 |
| Allowed (%) | 3.8 | 3.5 | 2.4 | 3.0 | 2.54 |
| Outliers (%) | 0.0 | 0.2 | 0.1 | 0.4 | 0.24 |

[1]Values in parentheses are for the highest resolution shell.

Figure 10A:
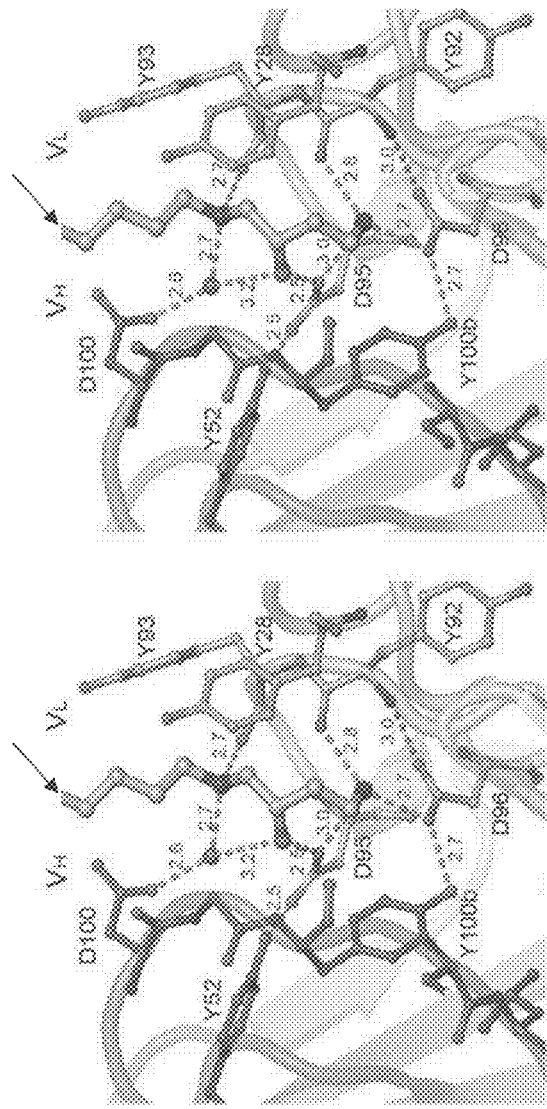
FIGS. 10A-10B is a series of diagrams showing a hydrogen bond network for the hypusine interaction.

The hypusine-binding pocket was comprised primarily of residues in complementarity determining regions (CDR) L1, L3 and H3. There were only 3 heteroatoms on the side chain of hypusine available for polar interactions (FIG. 3A). Inspection of the hypusine-FabHpu24 interface revealed a network of interactions at the distal end of hypusine—the 4-amino-2-hydroxybutyl group—including hydrogen bond and salt bridge interactions (FIG. 10A). Specifically, the first heteroatom (11-N) in the terminal amino group of hypusine was likely positively charged in the crystallization conditions, because its predicted pKa was 9.8 by analytic continuum electrostatics (ACE) (Schaefer et al., *The Journal of Physical Chemistry*, 100:1578:1599, 1996). The heteroatom (11-N) was anchored by a salt bridge with $V_L$ D96 at the bottom of the pocket and 2 additional hydrogen bonds to the side chain of $V_L$ D95 and the main chain carbonyl group of $V_H$ Y92. Additionally, $V_L$ D96 is stabilized by $V_H$ Y100b and $V_L$ Y92 through hydrogen bonds. The second heteroatom, the 9-hydroxyl group of hypusine, formed hydrogen bonds to $V_L$ D95, $V_H$ Y100b and a water molecule. Furthermore, the water molecule, coordinated by $V_H$ D100, also interacted with the third heteroatom (7-N), whose predicted pKa was 10.2 and which also formed a hydrogen bond to the carbonyl group of $V_L$ Y93. By contrast the proximal end of hypusine may be more flexible as suggested by sparse electron density. This was not surprising because the aliphatic chain can only be confined by hydrophobic interactions. Nevertheless, the proximal portion of hypusine functions as a spacer allowing the distal end to reach the bottom of the binding pocket.

FabHpu98 Hypusine and Deoxyhypusine Complex

FabHpu98 had dual specificity in that it bound to both hypusine and deoxyhypusine. The FabHpu98-hypusine and FabHpu98-deoxyhypusine complex crystals grew under the same conditions, and their X-ray crystallography structures were determined at 2.0 Å resolution. The complexes crystallized in C222 space group with two every similar FabHpu98 in the asymmetric unit (rmsd of 0.764 Å). One FabHpu98 molecule formed a complex with hypusine or deoxyhypusine while the other FabHpu98 molecule was in the uncomplexed form, since its paratope was blocked by intermolecular contacts.

In the FabHpu98 complex hypusine or deoxyhypusine also bound in a deep pocket constituted by the $V_H$ and $V_L$ interface, with 148 Å$^2$ and 156 Å$^2$ of buried surface area $V_H$ and $V_L$ chains, respectively (FIG. 9B). Hypusine was tilted to slide down into the binding pocket of FabHpu98, but was nearly vertical to project between the variable domains of FabHpu24. The 2 hypusine moieties projected at an angle of 46° with respect to each other.

Figure 10B:
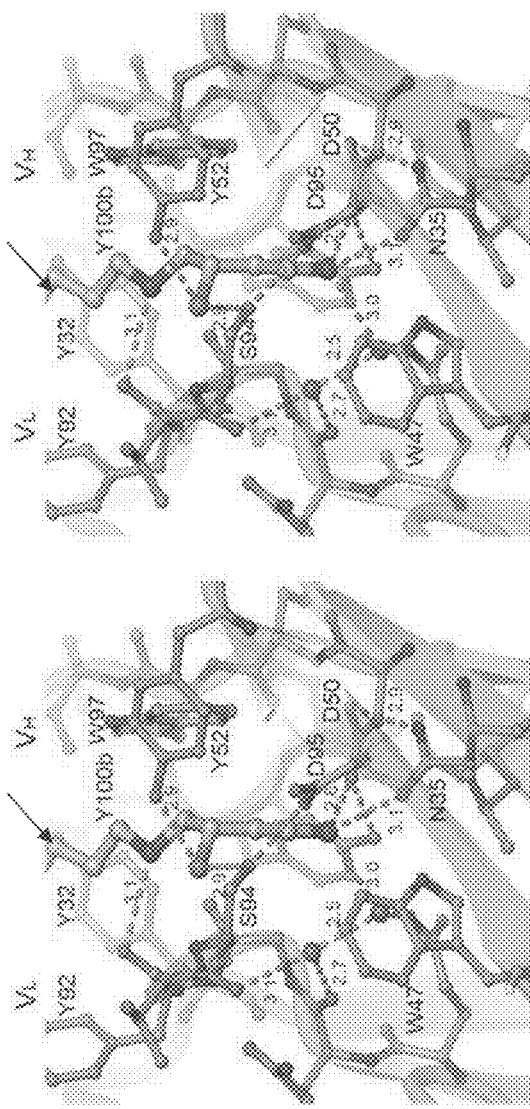

In the FabHpu98-hypusine complex, the 4-amino-2-hydroxybutyl group was also completely buried and coordinated by electrostatic interaction and hydrogen bonds, while the rest of hypusine was semi-buried. At the bottom of the pocket, the terminal amino group (11-N) of hypusine formed hydrogen bonds with $V_H$ framework residue N35, D95 and an ordered water molecule. The terminal amino group also interacted with $V_H$ D50 through an electrostatic interaction. All of these contacting residues were further positioned through a hydrogen bond network with neighboring residues (FIG. 10B). The heteroatom (7-N) formed hydrogen bonds with the carbonyl group of $V_L$ Y92 and a sulfate ion. The latter was indispensable in specificity and affinity, since surface plasmon resonance (SPR) experiments using HEPES and Tris buffers showed that FabHpu98 bound to hypusine or deoxyhypusine with similar affinities.

Aromatic residues apparently provided a favorable hydrophobic environment for the aliphatic portion of hypusine or deoxyhypusine. Unlike FabHpu24 hypusine complex, the nearby residues were also revealed in the simulated annealing mFo-dFc omit electro density map (FIG. 8B). The model showed that only peptide backbone atoms made contact with FabHpu98.

Comparison of Deoxyhypusine and Hypusine Interactions

Figure 11A:
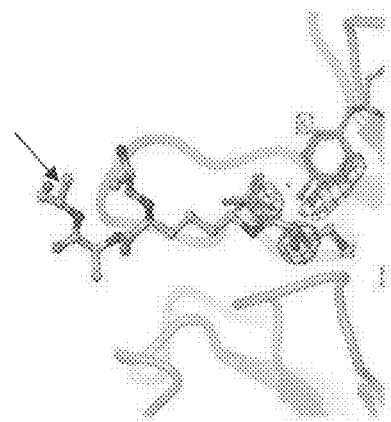
FIGS. 11A-11C is a series of diagrams showing comparison of hypusine and deoxyhypusine binding to FabHpu98.
Figure 11B:
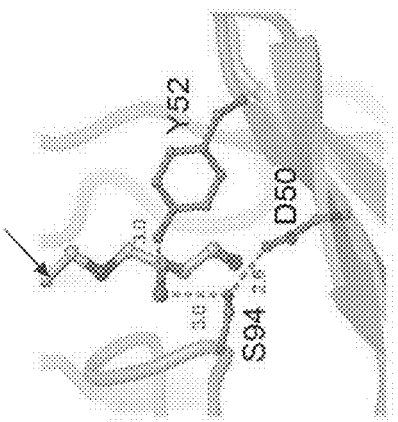

Hypusine and deoxyhypusine adopted similar conformations to insert into the deep pocket constituted by FabHpu98. However, there were differences in deoxyhypusine and hypusine interaction. Firstly, the hydroxyl group of hypusine were unambiguously revealed in the Fo(hypusine)-Fo(deoxyhypusine) difference map, which was calculated by using phases from the FabHpu98:hypusine model (FIG. 11A). The hydroxyl group of hypusine formed a hydrogen network with $V_L$ S94, $V_H$ Y52 and a sulfate ion (FIG. 11B).

Figure 11C:
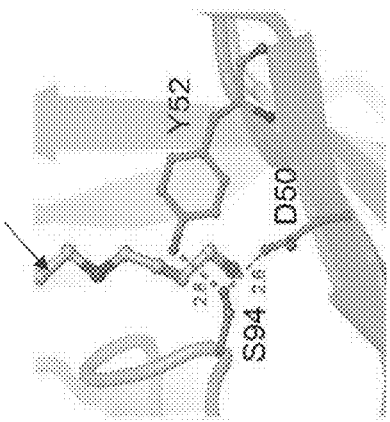
Figure 13:
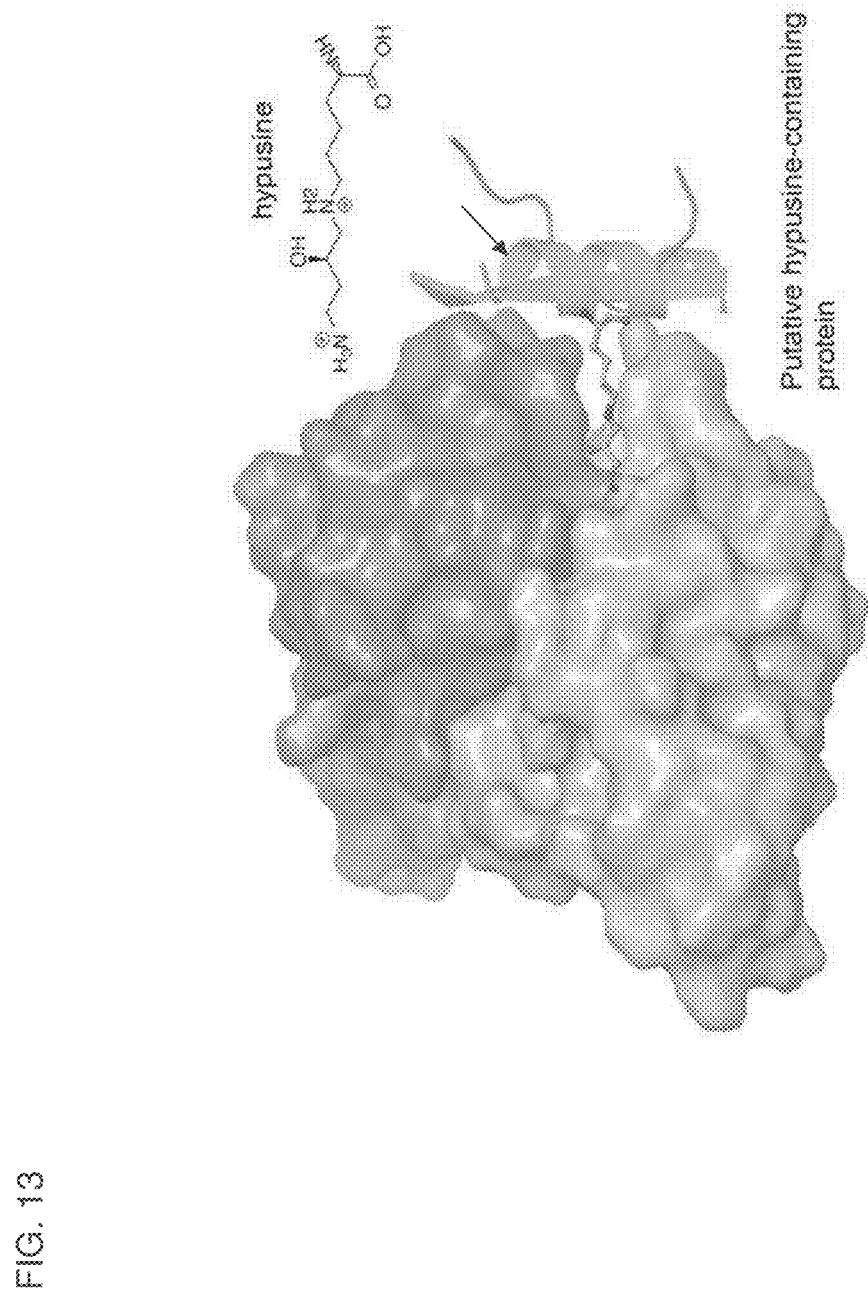
FIG. 13 is a diagram showing a simulated model of any anti-hypusine antibody described herein binding to hypusine on a putative hypusine-containing polypeptide with minimal dependence on the amino acid sequences surrounding hypusine. Arrow indicates hypusine containing protein.

As previous described, $V_H$ Y52 function was indispensable for deoxyhypusine interaction. The hydroxyl group of the hypusine formed 2 relatively long hydrogen bonds with $V_L$ S94 (3.0 Å) and $V_H$ Y52 side chains (3.0 Å) (FIG. 11B). While in in the FabHpu98-deoxyhypusine complex, the 2 hydrogen bonds to the hydroxyl group no longer existed. Instead, $V_H$ Y52 displayed side-chain movement and projected toward $V_L$ S94, and apparently formed a (2.8 Å) hydrogen bond (FIG. 11C). These observations were consistent with the mutagenesis and SPR studies. The $V_H$ Y52F mutant displayed weaker binding affinity to hypusine-containing peptides, compared to wild-type FabHpu98 (FIG. 3C), likely due to loss of a hydrogen bond. Furthermore, the $V_H$ Y52F mutation abolished detectable interaction with deoxyhypusine likely because of its inability to form a hydrogen bond with $V_L$ S94. Thus, $V_H$ residue Y52 played a pivotal role in interaction with deoxyhypusine.

FabHpu24.B Hypusinated Peptide Complex

The crystal structure of FabHpu24.B-hypusinated C1 peptide complex was determined at 2.4 Å resolution to better understand the molecular basis for the 30-fold affinity improvement of FabHpu24.B. The crystals of FabHpu24.B were isomorphous to FabHpu24, although the unit cell is twice big as that of FabHpu24. Although the primary sequences of FabHpu24.B differed from its parental FabHpu24 in CDR L1, L2 and H2, the backbone conformational change was only observed in CDR H2, which further pushed CDR H3 towards the hypusine moiety (FIG. 12A). Consequently, a hydrogen bond between FabHpu24.B $V_H$ D100 and $V_L$ Y28 created a larger contact area to embrace hypusine. Hypusine was apparently anchored in the deep pocket with the same hydrogen network, except that the third heteroatom (7-N) directly formed a hydrogen bond with the carbonyl group of $V_H$ G100a in FabHpu24.B, instead of the coordinated water (FIG. 12B). Furthermore, the flanking residues adjacent to hypusine were also involved in the interaction with FabHpu24.B. The carbonyl group of $V_H$ M99 and the $V_H$ D56 side chain formed hydrogen bonds with backbone of the C1 peptide. Additionally, $V_H$ residue D56 also interacted with the side chain of the flanking residue in peptide S6. These results may account for the difference in binding affinities between FabHpu24.B and hypusine with different flanking sequences varying from 6 nM to 186 nM. Although only hypusine was observed in the FabHpu24-hypusine complex, the flanking sequences also impacted the interaction between FabHpu24 and hypusine. Nevertheless, FabHpu24.B was able to bind to all 6 synthesized hypusinated peptides.

FabHpu98.61 Hypusinated Peptide Complex

An X-ray crystallographic structure of FabHpu98.61-hypusinated C1 peptide complex was determined at 2.2 Å resolution to gain molecular insight into antibody binding to hypusine. The complex crystallized in C2 space group with two every similar FabHpu98.61-hypusine complexes in the asymmetric unit (rmsd of 0.14 Å). FabHpu98.61 and FabHpu98 bound to the hypusinated C1 peptide in a very similar manner, except the CDR H1 loop, within which C27 and C32 formed a disulfide (FIG. 12C). As a result, FabHpu98.61 CDR H1 leaned towards $V_H$ W9 and may improve its packing against hypusine. In addition, VH T33 moved closer and formed an additional H-bond with 11-N of hypusine, whose other interactions remained the same.

```
SEQUENCES
Amino acid sequence of Hpu24
light chain CDR1 (Kabat)
                                            (SEQ ID NO: 1)
QSSETVYRGDWLS Amino acid sequence of Hpu24.B
light chain CDR1 (Kabat)
                                            (SEQ ID NO: 2)
RSRQRVYLGDWLS Amino acid sequence of Hpu91, Hpu98 and
Hpu98.61 light chain CDR1 (Kabat)
                                            (SEQ ID NO: 3)
QASEDIKRYLA Amino acid sequence of Hpu24 light chain
CDR2 (Kabat)
                                            (SEQ ID NO: 4)
DASYLAS Amino acid sequence of Hpu24.B light chain
CDR2 (Kabat)
                                            (SEQ ID NO: 5)
DASFRGD Amino acid sequence of Hpu91, Hpu98 and
Hpu98.61 light chain CDR2 (Kabat)
                                            (SEQ ID NO: 6)
AASKLAS Amino acid sequence of Hpu24 andHpu24.B
light chain CDR3 (Kabat)
                                            (SEQ ID NO: 7)
LGGYYDDADDT Amino acid sequence of Hpu98 and Hpu98.61
light chain CDR3 (Kabat)
                                            (SEQ ID NO: 8)
QQGYTSSNVNNA Amino acid sequence of Hpu24 andHpu24.B
heavy chain CDR1 (Kabat)
                                            (SEQ ID NO: 9)
DYAMI
```

Amino acid sequence of Hpu91 heavy chain CDR1 (Kabat)
(SEQ ID NO: 10)
TYTIN

Amino acid sequence of Hpu98 heavy chain CDR1 (Kabat)
(SEQ ID NO: 11)
TYTMN

Amino acid sequence of Hpu98.61 heavy chain CDR1 (Kabat)
(SEQ ID NO: 12)
HCTMN

Amino acid sequence of Hpu24 heavy chain CDR2 (Kabat)
(SEQ ID NO: 13)
IIYGGSNKLAYAKWA Amino acid sequence of Hpu24.B heavy chain CDR2 (Kabat)
(SEQ ID NO: 14)
IIYGVINDLAYAKWA Amino acid sequence of Hpu91 heavy chain CDR2 (Kabat)
(SEQ ID NO: 15)
DIWSDGNTYYANWA Amino acid sequence of Hpu98 and Hpu98.61 heavy chain CDR2 (Kabat)
(SEQ ID NO: 16)
DIYTDGNTYYANWA Amino acid sequence of Hpu24 and Hpu24.B heavy chain CDR3 (Kabat)
(SEQ ID NO: 17)
GYGSMDGYDRLNL Amino acid sequence of Hpu91 heavy chain CDR3 (Kabat)
(SEQ ID NO: 18)
DSWDTSIYYGLDL Amino acid sequence of Hpu98 and Hpu98.61 heavy chain CDR3 (Kabat)
(SEQ ID NO: 19)
DSWDASSYYGLDL Amino acid sequence of Hpu24 light chain variable region
(SEQ ID NO: 20)
AAVLTQTPSPVSAAVGGTVTISCQSSETVYRGDWLSWFQKKPGQPPKLLI
YDASYLASGVSSRFSGSGSGTHFTLTISGVQCDDAATYYCLGGYYDDADD
TFGGGTEVVVK Amino acid sequence of Hpu24.B light chain variable region
(SEQ ID NO: 21)
AAVLTQTPSPVSAAVGGTVTISCRSRQRVYLGDWLSWFQKKPGQPPKLLI
YDASFRGDGVSSRFSGSGSGTHFTLTISGVQCDDAATYYCLGGYYDDADD
TFGGGTEVVVK Amino acid sequence of Hpu91 light chain variable region
(SEQ ID NO: 22)
AIKMTQTPSSVSAAVGGTVTINCQASEDIKRYLAWYQQKPGQPPKLLIYA
ASKLASGVSSRFTGSGSGTEYTLTISGVQCDDAATYYCQQGYTSTNVNNA
FGGGTEVVVK Amino acid sequence of Hpu98 and Hpu98.61 light chain variable region
(SEQ ID NO: 23)
AIKMTQTPSSVSAAVGGTVTINCQASEDIKRYLAWYQQKPGQPPKLLIYA
ASKLASGVSSRFKGSGSGTEYTLTISGVQCDDAATYYCQQGYTSSNVNNA
FGGGTEVVVK Amino acid sequence of Hpu24 heavy chain variable region
(SEQ ID NO: 24)
QEQLKESGGRLVAPGTPLTLTCTVSGFDISDYAMIWVRQAPGKGLEWIGI
IYGGSNKLAYAKWAKGRFTISRTSTTVDLKITSPTTEDTATYFCARGYGS
MDGYDRLNLWGQGTLVTVSS Amino acid sequence of Hpu24.B heavy chain variable region
(SEQ ID NO: 25)
QEQLKESGGRLVAPGTPLTLTCTVSGFDISDYAMIWVRQAPGKGLEWIGI
IYGVINDLAYAKWAKGRFTISRTSTTVDLKITSPTTEDTATYFCARGYGS
MDGYDRLNLWGQGTLVTVSS Amino acid sequence of Hpu91 heavy chain variable region
(SEQ ID NO: 26)
QSVEESGGRLVTPGTPLTLTCTVSAFSLSTYTINWVRQAPGKGLEWIGDI
WSDGNTYYANWAKGRFTISKTSTTVDLKITSPTTEDTATYFCARDSWDTS
IYYGLDLWGQGTLVTVSS Amino acid sequence of Hpu98 heavy chain variable region
(SEQ ID NO: 27)
QSVEESGGRLVTPGTPLTLTCTVSGFSLSTYTMNWVRQAPGKGLEWIGDI
YTDGNTYYANWAKGRFTISKTSTTVDLKITSPTTEDTATYFCARDSWDAS
SYYGLDLWGQGTLVTVSS Amino acid sequence of Hpu98.61 heavy chain variable region
(SEQ ID NO: 28)
QSVEESGGRLVTPGTPLTLTCTVSACSLYHCTMNWVRQAPGKGLEWIGDI
YTDGNTYYANWAKGRFTISKTSTTVDLKITSPTTEDTATYFCARDSWDAS
SYYGLDLWGQGTLVTVSS Amino acid sequence of Hpu24 light chain
(SEQ ID NO: 29)
AAVLTQTPSPVSAAVGGTVTISCQSSETVYRGDWLSWFQKKPGQPPKLLI
YDASYLASGVSSRFSGSGSGTHFTLTISGVQCDDAATYYCLGGYYDDADD
TFGGGTEVVVKGDPVAPTVLIFPPAADQVATGTVTIVCVANKYFPDVTVT
WEVDGTTQTTGIENSKTPQNSADCTYNLSSTLTLTSTQYNSHKEYTCKVT
QGTTSVVQSFNRGDC Amino acid sequence of Hpu24.B light chain
(SEQ ID NO: 30)
AAVLTQTPSPVSAAVGGTVTISCRSRQRVYLGDWLSWFQKKPGQPPKLLI
YDASFRGDGVSSRFSGSGSGTHFTLTISGVQCDDAATYYCLGGYYDDADD
TFGGGTEVVVKGDPVAPTVLIFPPAADQVATGTVTIVCVANKYFPDVTVT
WEVDGTTQTTGIENSKTPQNSADCTYNLSSTLTLTSTQYNSHKEYTCKVT
QGTTSVVQSFNRGDC -continued Amino acid sequence of Hpu91 light chain
(SEQ ID NO: 31)
AIKMTQTPSSVSAAVGGTVTINCQASEDIKRYLAWYQQKPGQPPKLLIYA
ASKLASGVSSRFTGSGSGTEYTLTISGVQCDDAATYYCQQGYTSTNVNNA
FGGGTEVVVKGDPVAPTVLIFPPAADQVATGTVTIVCVANKYFPDVTVTW
EVDGTTQTTGIENSKTPQNSADCTYNLSSTLTLTSTQYNSHKEYTCKVTQ
GTTSVVQSFNRGDC Amino acid sequence of Hpu98 and Hpu98.61
light chain
(SEQ ID NO: 32)
AIKMTQTPSSVSAAVGGTVTINCQASEDIKRYLAWYQQKPGQPPKLLIYA
ASKLASGVSSRFKGSGSGTEYTLTISGVQCDDAATYYCQQGYTSSNVNNA
FGGGTEVVVKGDPVAPTVLIFPPAADQVATGTVTIVCVANKYFPDVTVTW
EVDGTTQTTGIENSKTPQNSADCTYNLSSTLTLTSTQYNSHKEYTCKVTQ
GTTSVVQSFNRGDC Amino acid sequence of Hpu24 heavy chain
(SEQ ID NO: 33)
QEQLKESGGRLVAPGTPLTLTCTVSGFDISDYAMIWVRQAPGKGLEWIGI
IYGGSNKLAYAKWAKGRFTISRTSTTVDLKITSPTTEDTATYFCARGYGS
MDGYDRLNLWGQGTLVTVSSGQPKGPSVFPLAPCCGDTPSSTVTLGCLVK
GYLPEPVTVTWNSGTLTNGVRTFPSVRQSSGLYSLSSVVSVTSSSQPVTC
NVAHPATNTKVDKTVAPSTCSKPT Amino acid sequence of Hpu24.B heavy chain
(SEQ ID NO: 34)
QEQLKESGGRLVAPGTPLTLTCTVSGFDISDYAMIWVRQAPGKGLEWIGI
IYGVINDLAYAKWAKGRFTISRTSTTVDLKITSPTTEDTATYFCARGYGS
MDGYDRLNLWGQGTLVTVSSGQPKGPSVFPLAPCCGDTPSSTVTLGCLVK
GYLPEPVTVTWNSGTLTNGVRTFPSVRQSSGLYSLSSVVSVTSSSQPVTC
NVAHPATNTKVDKTVAPSTCSKPT Amino acid sequence of Hpu91 heavy chain
(SEQ ID NO: 35)
QSVEESGGRLVTPGTPLTLTCTVSAFSLSTYTINWVRQAPGKGLEWIGDI
WSDGNTYYANWAKGRFTISKTSTTVDLKITSPTTEDTATYFCARDSWDTS
IYYGLDLWGQGTLVTVSSGQPKGPSVFPLAPCCGDTPSSTVTLGCLVKGY
LPEPVTVTWNSGTLTNGVRTFPSVRQSSGLYSLSSVVSVTSSSQPVTCNV
AHPATNTKVDKTVAPSTCSKPT Amino acid sequence of Hpu98 heavy chain
(SEQ ID NO: 36)
QSVEESGGRLVTPGTPLTLTCTVSGFSLSTYTMNWVRQAPGKGLEWIGDI
YTDGNTYYANWAKGRFTISKTSTTVDLKITSPTTEDTATYFCARDSWDAS
SYYGLDLWGQGTLVTVSSGQPKGPSVFPLAPCCGDTPSSTVTLGCLVKGY
LPEPVTVTWNSGTLTNGVRTFPSVRQSSGLYSLSSVVSVTSSSQPVTCNV
AHPATNTKVDKTVAPSTCSKPT Amino acid sequence of Hpu98.61 heavy chain
(SEQ ID NO: 37)
QSVEESGGRLVTPGTPLTLTCTVSACSLYHCTMNWVRQAPGKGLEWIGDI
YTDGNTYYANWAKGRFTISKTSTTVDLKITSPTTEDTATYFCARDSWDAS
SYYGLDLWGQGTLVTVSSGQPKGPSVFPLAPCCGDTPSSTVTLGCLVKGY
LPEPVTVTWNSGTLTNGVRTFPSVRQSSGLYSLSSVVSVTSSSQPVTCNV
AHPATNTKVDKTVAPSTCSKPT Amino acid sequence of Hpu24 andHpu24.B light
chain FR1
(SEQ ID NO: 38)
AAVLTQTPSPVSAAVGGTVTISC Amino acid sequence of Hpu91, Hpu98 and Hpu98.61
light chain FR1
(SEQ ID NO: 39)
AIKMTQTPSSVSAAVGGTVTINC Amino acid sequence of Hpu24 andHpu24.B light
chain FR2
(SEQ ID NO: 40)
WFQKKPGQPPKLLIY Amino acid sequence of Hpu91, Hpu98 and Hpu98.61
light chain FR2
(SEQ ID NO: 41)
WYQQKPGQPPKLLIY Amino acid sequence of Hpu24 andHpu24.B light
chain FR3
(SEQ ID NO: 42)
GVSSRFSGSGSGTHFTLTISGVQCDDAATYYC Amino acid sequence of Hpu91 light chain FR3
(SEQ ID NO: 43)
GVSSRFTGSGSGTEYTLTISGVQCDDAATYYC Amino acid sequence of Hpu98 and Hpu98.61
light chain FR3
(SEQ ID NO: 44)
GVSSRFKGSGSGTEYTLTISGVQCDDAATYYC Amino acid sequence of Hpu24, Hpu24.B, Hpu91,
Hpu98 and Hpu98.61 light chain FR4
(SEQ ID NO: 45)
FGGGTEVVVK Amino acid sequence of Hpu24 andHpu24.B heavy
chain FR1
(SEQ ID NO: 46)
QEQLKESGGRLVAPGTPLTLTCTVSGFDIS Amino acid sequence of Hpu91 heavy chain FR1
(SEQ ID NO: 47)
QSVEESGGRLVTPGTPLTLTCTVSAFSLS Amino acid sequence of Hpu98 heavy chain FR1
(SEQ ID NO: 48)
QSVEESGGRLVTPGTPLTLTCTVSGFSLS Amino acid sequence of Hpu98.61 heavy chain FR1
(SEQ ID NO: 49)
QSVEESGGRLVTPGTPLTLTCTVSACSLY Amino acid sequence of Hpu24, Hpu24.B, Hpu91,
pu98 and Hpu98.61 heavy chain FR2
(SEQ ID NO: 50)
WVRQAPGKGLEWIG Amino acid sequence of Hpu24 andHpu24.B heavy
chain FR3
(SEQ ID NO: 51)
KGRFTISRTSTTVDLKITSPTTEDTATYFCAR Amino acid sequence of Hpu91, Hpu98 and Hpu98.61
heavy chain FR3
(SEQ ID NO: 52)
KGRFTISKTSTTVDLKITSPTTEDTATYFCAR -continued Amino acid sequence of Hpu24,Hpu24.B,Hpu91,
Hpu98 and Hpu98.61 heavy chain FR4

(SEQ ID NO: 53)
WGQGTLVTVSS

Amino acid sequence of Hpu91 light chain CDR3
(Kabat)

(SEQ ID NO: 72)
QQGYTSTNVNNA

---

What is claimed is:

1. A method for detecting a hypusine-containing polypeptide in a sample comprising the steps of: (a) contacting the sample with an isolated antibody that specifically binds to hypusine in a polypeptide; and (b) detecting the antibody bound to the polypeptide in the sample, wherein the antibody comprises:
   (i) a heavy chain variable region comprising three heavy chain hypervariable regions (HVR-Hs), and a light chain variable region comprising three light chain hypervariable regions (HVR-Ls), wherein the HVR-H comprise HVR-H1 comprising the amino acid sequence of SEQ ID NO:11, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8; or
   (ii) a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO:12, HVR-H2 comprising the amino acid sequence of SEQ ID NO:16, and HVR-H3 comprising the amino acid sequence of SEQ ID NO: 19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8.

2. The method of claim 1, wherein the antibody is linked to a detection agent.

3. The method of claim 1, wherein the antibody bound to the polypeptide is detected by using a secondary agent.

4. The method of claim 2, wherein the detection agent is a chemiluminescent label, a chromophore, a fluorophore, a magnetic particle, a dye, a radiolabel, or an enzyme.

5. The method of claim 1, wherein the detection is by an assay selected from the group consisting of enzyme-linked immunosorbent assay, radioimmunoassay, immunoprecipitation, chromatography, immunohistochemistry, immunofluorescence, surface plasmon resonance, fluorescence-activated cell sorting and mass spectrometry.

6. The method of claim 1, wherein the sample is a biological sample.

7. The method of claim 6, wherein the biological sample comprises a cell or tissue.

8. The method of claim 6, wherein the biological sample is a fluid.

9. A method for isolating a hypusine-containing polypeptide in a sample comprising the steps of: (a) contacting the sample with an isolated antibody that specifically binds to hypusine in a polypeptide; and (b) isolating the polypeptide bound to the antibody, wherein the antibody comprises:
   (i) a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO:11, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8; or
   (ii) a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO: 12, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8.

10. The method of claim 9, wherein the antibody is immobilized to a solid surface.

11. The method of claim 9, wherein the sample is a biological sample.

12. The method of claim 11, wherein the biological sample comprises a cell or tissue.

13. The method of claim 11, wherein the biological sample is a fluid.

14. The method of claim 1, wherein the antibody comprises a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO:11, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8.

15. The method of claim 14, wherein the heavy chain variable region comprises a sequence having at least 95% sequence identity to SEQ ID NO:27, and the light chain variable region comprises a sequence having at least 95% sequence identity to SEQ ID NO:23.

16. The method of claim 1, wherein the antibody comprises a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO:12, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8.

17. The method of claim 16, wherein the heavy chain variable region comprises a sequence having at least 95% sequence identity to SEQ ID NO:28, and the light chain variable region comprises a sequence having at least 95% sequence identity to SEQ ID NO:23.

18. The method of claim 1, wherein the heavy chain variable region comprises the amino acid sequence of SEQ ID NO:27 or SEQ ID NO:28, and the light chain variable region comprises the amino acid sequence of SEQ ID NO:23.

19. The method of claim 9, wherein the antibody comprises a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO:11, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8.

20. The method of claim 19, wherein the heavy chain variable region comprises a sequence having at least 95% sequence identity to SEQ ID NO:27, and the light chain variable region comprises a sequence having at least 95% sequence identity to SEQ ID NO:23.

21. The method of claim 9, wherein the antibody comprises a heavy chain variable region comprising three heavy chain hypervariable regions (HVR-Hs), and a light chain variable region comprising three light chain hypervariable regions (HVR-Ls), wherein the HVR-Hs comprise HVR-H1 comprising the amino acid sequence of SEQ ID NO:12, HVR-H2 comprising the amino acid sequence of SEQ ID NO:16, and HVR-H3 comprising the amino acid sequence of SEQ ID NO:19; and the HVR-Ls comprise HVR-L1 comprising the amino acid sequence of SEQ ID NO:3, HVR-L2 comprising the amino acid sequence of SEQ ID NO:6, and HVR-L3 comprising the amino acid sequence of SEQ ID NO:8.

22. The method of claim 21, wherein the heavy chain variable region comprises a sequence having at least 95% sequence identity to SEQ ID NO:28, and the light chain variable region comprises a sequence having at least 95% sequence identity to SEQ ID NO:23.

23. The method of claim 9, wherein the heavy chain variable region comprises the amino acid sequence of SEQ ID NO:27 or SEQ ID NO:28, and the light chain variable region comprises the amino acid sequence of SEQ ID NO:23.

* * * * *